US006761733B2

(12) United States Patent
Chobotov et al.

(10) Patent No.: US 6,761,733 B2
(45) Date of Patent: Jul. 13, 2004

(54) DELIVERY SYSTEM AND METHOD FOR BIFURCATED ENDOVASCULAR GRAFT

(75) Inventors: Michael V. Chobotov, Santa Rosa, CA (US); Brian A. Glynn, Santa Rosa, CA (US)

(73) Assignee: TriVascular, Inc., Santa Rosa, CA (US)

(*) Notice: Subject to any disclaimer, the term of this patent is extended or adjusted under 35 U.S.C. 154(b) by 0 days.

(21) Appl. No.: 09/917,371

(22) Filed: Jul. 27, 2001

(65) Prior Publication Data

US 2002/0151953 A1 Oct. 17, 2002

Related U.S. Application Data

(63) Continuation-in-part of application No. 09/834,278, filed on Apr. 11, 2001.

(51) Int. Cl.$^{7}$ .................................................. A61F 2/06

(52) U.S. Cl. ...................................... 623/1.12; 606/108

(58) Field of Search .............................. 623/1.11, 1.12; 606/108

(56) References Cited

U.S. PATENT DOCUMENTS

| | | | | |
|---|---|---|---|---|
| 4,140,126 | A | 2/1979 | Choudhury | 128/325 |
| 4,562,596 | A | 1/1986 | Kornberg | 623/1 |
| 4,580,568 | A | 4/1986 | Gianturco | 128/345 |
| 4,787,899 | A | 11/1988 | Lazarus | 623/1 |
| 5,104,399 | A | 4/1992 | Lazarus | 623/1 |
| 5,151,105 | A | 9/1992 | Kwan-Gett | 623/1 |
| 5,156,620 | A | 10/1992 | Pigott | 623/1 |
| 5,360,443 | A | 11/1994 | Barone et al. | 623/1 |
| 5,387,235 | A | 2/1995 | Chuter | 623/1 |
| 5,397,345 | A | 3/1995 | Lazarus | 623/1 |
| 5,456,694 | A | 10/1995 | Marin et al. | 606/198 |
| 5,456,713 | A | 10/1995 | Chuter | 623/1 |
| 5,464,449 | A | 11/1995 | Ryan et al. | 623/1 |

(List continued on next page.)

FOREIGN PATENT DOCUMENTS

| | | |
|---|---|---|
| EP | 0 943 302 A2 | 9/1999 |
| EP | 1212988 | 6/2002 |
| EP | 1212989 | 6/2002 |
| WO | WO 98/06355 | 2/1998 |
| WO | WO 98/41167 | 9/1998 |
| WO | WO 00/33769 | 6/2000 |
| WO | WO 00/42947 | 7/2000 |
| WO | WO 00/42948 | 7/2000 |
| WO | 02/056798 | 7/2002 |
| WO | 02/060345 | 8/2002 |
| WO | 03/022181 | 3/2003 |

OTHER PUBLICATIONS

US 6,413,270, 7/2002, Thornton et al. (withdrawn)

AneuRX stent graft brochure, An Innovative Modular Approach For The Treatment Of Abdominal Aortic Aneurysms (AAA), *Medtronic*.

(List continued on next page.)

*Primary Examiner*—Corrine McDermott
*Assistant Examiner*—Thomas J Sweet
(74) *Attorney, Agent, or Firm*—Townsend and Townsend and Crew LLP

(57) ABSTRACT

A flexible low profile delivery system for delivery of an expandable intracorporeal device, specifically, an endovascular graft, which has at least one belt circumferentially disposed about the device in a constraining configuration. The belt is released by a release member, such as a release wire, by retracting the wire from looped ends of the belt. Multiple belts can be used and can be released sequentially so as to control the order of release and placement of the endovascular graft. An outer protective sheath may be disposed about the endovascular graft while in a constrained state which must first be retracted or otherwise removed prior to release of the graft from a constrained state. The delivery system can be configured for delivery over a guiding device such as a guidewire. The delivery system can also be configured for delivery of bifurcated intracorporeal devices.

75 Claims, 52 Drawing Sheets

U.S. PATENT DOCUMENTS 5,480,423 A 1/1996 Ravenscroft et al. .......... 623/1
5,489,295 A 2/1996 Piplani et al. ................ 623/1
5,522,880 A 6/1996 Barone et al.
5,522,883 A 6/1996 Slater et al.
5,562,724 A 10/1996 Vorwerk et al.
5,562,726 A 10/1996 Chuter .......................... 623/1
5,578,071 A 11/1996 Parodi .......................... 623/1
5,578,072 A 11/1996 Barone et al.
5,609,625 A 3/1997 Piplani et al.
5,628,783 A 5/1997 Quiachon et al. ............. 623/1
5,632,772 A 5/1997 Alcime et al. ................ 623/1
5,639,278 A 6/1997 Dereume et al. ............. 623/1
5,662,675 A 9/1997 Polanskyj Stockert et al.
5,662,700 A 9/1997 Lazarus ........................ 623/1
5,665,115 A 9/1997 Cragg .......................... 623/1
5,669,936 A 9/1997 Lazarus ........................ 623/1
5,676,671 A 10/1997 Inoue ......................... 606/108
5,676,696 A 10/1997 Marcade ........................ 623/1
5,676,697 A 10/1997 McDonald ..................... 623/1
5,683,449 A 11/1997 Marcade ........................ 623/1
5,683,451 A 11/1997 Lenker et al. ................ 623/1
5,693,083 A 12/1997 Baker et al. .................. 623/1
5,693,084 A 12/1997 Chuter .......................... 623/1
5,693,088 A 12/1997 Lazarus ........................ 623/1
5,709,701 A 1/1998 Parodi ........................ 606/194
5,709,703 A 1/1998 Lukic et al. ................ 606/198
5,720,776 A 2/1998 Chuter et al. ................. 623/1
5,723,004 A 3/1998 Dereume et al. ............. 623/1
5,733,325 A 3/1998 Robinson et al. ............. 623/1
5,749,920 A 5/1998 Quiachon et al. ............. 623/1
5,749,921 A 5/1998 Lenker et al. ................ 623/1
5,769,885 A 6/1998 Quiachon et al.
5,769,887 A 6/1998 Brown et al. ................. 623/1
5,782,909 A 7/1998 Quiachon et al.
5,800,518 A 9/1998 Piplani et al.
5,824,039 A 10/1998 Piplani et al.
5,824,041 A 10/1998 Lenker et al. ................ 623/1
5,824,058 A 10/1998 Ravenscroft et al. .......... 623/1
5,843,158 A 12/1998 Lenker et al. ................ 623/1
5,843,162 A * 12/1998 Inoue ........................ 623/1.13
5,843,167 A 12/1998 Dwyer et al. ................. 623/1
5,855,598 A 1/1999 Pinchuk ........................ 623/1
5,871,536 A 2/1999 Lazarus et al. ............... 623/1
5,873,906 A 2/1999 Lau et al.
5,906,619 A 5/1999 Olson et al. ................ 606/108
5,919,204 A 7/1999 Lukic et al. ................ 606/198
5,944,750 A 8/1999 Tanner et al. ................. 623/1
5,954,729 A 9/1999 Bachmann et al. ......... 606/108
5,957,973 A 9/1999 Quiachon et al.
5,968,068 A 10/1999 Dehdashtian et al. ....... 606/192
5,972,023 A 10/1999 Tanner et al. .............. 606/219
5,976,179 A 11/1999 Inoue ........................... 623/1
5,976,650 A 11/1999 Campbell et al.
5,984,964 A 11/1999 Roberts et al. ............... 623/12
5,993,481 A 11/1999 Marcade et al. .............. 623/1
6,001,123 A 12/1999 Lau
6,004,347 A 12/1999 McNamara et al. ........... 623/1
6,004,348 A 12/1999 Banas et al.
6,017,364 A 1/2000 Lazarus
6,019,778 A 2/2000 Wilson et al. ............. 606/198
6,024,763 A 2/2000 Lenker et al. ................ 623/1
6,030,414 A 2/2000 Taheri .......................... 623/1
6,036,413 A 3/2000 Chandrasekar ............. 409/231
6,036,723 A 3/2000 Anidjar et al. ................ 623/1
6,036,725 A 3/2000 Avellanet ...................... 623/1
6,039,758 A 3/2000 Quiachon et al. ............. 623/1
6,042,589 A 3/2000 Marianne ................... 606/108
6,042,605 A 3/2000 Martin et al. ................. 623/1
6,045,557 A 4/2000 White et al. ............... 606/108
6,051,020 A 4/2000 Goicoechea et al. ........... 623/1
6,059,821 A 5/2000 Anidjar et al. ................ 623/1
6,070,589 A 6/2000 Keith et al. ................ 128/898
6,077,297 A 6/2000 Robinson et al. .......... 623/1.11
6,098,630 A 8/2000 Papazoglou
6,110,198 A 8/2000 Fogarty et al. ............ 623/1.12
6,126,685 A 10/2000 Lenker et al. ................ 623/1
6,132,459 A 10/2000 Piplani et al. ............ 623/1.13
6,139,572 A 10/2000 Campbell et al.
6,146,389 A 11/2000 Geitz ........................ 606/108
6,156,063 A 12/2000 Douglas .................... 623/1.12
6,165,210 A 12/2000 Lau et al. .................. 623/1.12
6,165,213 A 12/2000 Goicoechea et al. ....... 623/1.34
6,168,610 B1 1/2001 Marin et al. ............... 606/198
6,168,616 B1 1/2001 Brown, III ................. 623/1.11
6,168,617 B1 1/2001 Blaeser et al. ............ 623/1.11
6,168,620 B1 1/2001 Kerr .......................... 623/1.13
6,183,481 B1 2/2001 Lee et al. .................. 606/108
6,183,504 B1 2/2001 Inoue ........................ 623/1.11
6,187,036 B1 2/2001 Shaolian et al.
6,193,745 B1 2/2001 Fogarty et al. ............ 623/1.12
6,197,046 B1 3/2001 Piplani et al.
6,197,049 B1 3/2001 Shaolian et al.
6,200,339 B1 3/2001 Leschinsky et al. ....... 623/1.35
6,203,550 B1 3/2001 Olson ......................... 606/108
6,203,568 B1 3/2001 Lombardi et al.
6,210,422 B1 4/2001 Douglas ..................... 606/194
6,210,434 B1 4/2001 Quiachon et al.
6,210,435 B1 4/2001 Piplani et al. ............ 623/1.35
6,214,038 B1 4/2001 Piplani et al. ............ 623/1.11
6,224,609 B1 5/2001 Ressemann et al.
6,235,050 B1 5/2001 Quiachon et al.
6,235,051 B1 5/2001 Murphy ..................... 623/1.12
6,241,759 B1 6/2001 Piplani et al.
6,261,316 B1 7/2001 Shaolian et al. ........... 623/1.11
6,261,317 B1 7/2001 Inoue
6,264,662 B1 7/2001 Lauterjung
6,280,466 B1 8/2001 Kugler et al. .............. 623/1.12
6,283,991 B1 9/2001 Cox et al. .................. 623/1.13
6,287,315 B1 9/2001 Wijeratne et al.
6,287,329 B1 9/2001 Duerig et al.
6,287,330 B1 9/2001 Johansson et al.
6,293,969 B1 9/2001 Chuter
6,302,906 B1 10/2001 Goicoechea et al.
6,302,908 B1 10/2001 Parodi ....................... 623/1.31
6,306,145 B1 10/2001 Leschinsky
6,312,462 B1 11/2001 McDermott et al. ....... 623/1.25
6,322,587 B1 11/2001 Quiachon et al.
6,325,819 B1 12/2001 Pavcnik et al.
6,325,825 B1 12/2001 Kula et al.
6,331,186 B1 12/2001 Wang et al.
6,331,190 B1 12/2001 Shokoohi et al.
6,344,044 B1 2/2002 Fulkerson et al.
6,344,054 B1 2/2002 Parodi
6,352,553 B1 3/2002 van der Burg et al. .... 623/1.23
6,352,561 B1 3/2002 Leopold et al. ............ 623/1.23
6,416,536 B1 7/2002 Yee
6,425,898 B1 7/2002 Wilson et al.
6,428,566 B1 8/2002 Holt
6,428,567 B2 8/2002 Wilson et al.
6,432,129 B2 8/2002 DiCaprio
6,432,131 B1 8/2002 Ravenscroft
6,436,104 B2 8/2002 Hojeibane
6,443,979 B1 9/2002 Stalker et al.
6,447,501 B1 9/2002 Solar et al.
6,447,522 B2 9/2002 Gambale et al.
6,451,053 B1 9/2002 Dehdashtian et al.
6,471,718 B1 10/2002 Staehle et al.
6,471,722 B1 10/2002 Inoue
6,475,166 B1 11/2002 Escano
6,475,208 B2 11/2002 Mauch
6,478,807 B1 11/2002 Foreman et al.

| | | | |
|---|---|---|---|
| 6,485,515 | B2 | 11/2002 | Strecker |
| 6,500,202 | B1 | 12/2002 | Shaolian et al. |
| 6,517,574 | B1 | 2/2003 | Chuter |
| 6,520,983 | B1 | 2/2003 | Colgan et al. |
| 6,520,984 | B1 | 2/2003 | Garrison et al. |
| 6,530,947 | B1 | 3/2003 | Euteneuer et al. |
| 6,533,806 | B1 | 3/2003 | Sullivan et al. |
| 6,533,807 | B2 | 3/2003 | Wolinsky et al. |
| 6,533,811 | B1 | 3/2003 | Ryan et al. |
| 6,540,778 | B1 | 4/2003 | Quiachon et al. |
| 6,554,858 | B2 | 4/2003 | Dereume et al. |
| 6,562,063 | B1 | 5/2003 | Euteneuer et al. |
| 2001/0020184 | A1 | 9/2001 | Dehdashtain et al. ...... 623/1.16 |
| 2001/0037142 | A1 | 11/2001 | Stelter et al. |
| 2001/0047150 | A1 | 11/2001 | Chobotov |
| 2002/0099405 | A1 | 7/2002 | Yurek et al. |
| 2002/0099431 | A1 | 7/2002 | Armstrong et al. |
| 2002/0099433 | A1 | 7/2002 | Fischell et al. |
| 2002/0099435 | A1 | 7/2002 | Stinson |
| 2002/0099437 | A1 | 7/2002 | Anson et al. |
| 2002/0103525 | A1 | 8/2002 | Cummings |
| 2002/0111633 | A1 | 8/2002 | Stolze et al. |
| 2002/0111666 | A1 | 8/2002 | Hart et al. |
| 2002/0111675 | A1 | 8/2002 | Wilson |
| 2002/0116046 | A1 | 8/2002 | DiCaprio et al. |
| 2002/0116047 | A1 | 8/2002 | Vardi et al. |
| 2002/0123032 | A1 | 8/2002 | Gunderson et al. |
| 2002/0123794 | A1 | 9/2002 | Ellis et al. |
| 2002/0138081 | A1 | 9/2002 | Blaeser et al. |
| 2002/0138127 | A1 | 9/2002 | Stiger et al. |
| 2002/0138128 | A1 | 9/2002 | Stiger et al. |
| 2002/0143381 | A1 | 10/2002 | Gilligan et al. |
| 2002/0143383 | A1 | 10/2002 | Parodi |
| 2002/0143387 | A1 | 10/2002 | Soetikno et al. |
| 2002/0156489 | A1 | 10/2002 | Gellman et al. |
| 2002/0165602 | A1 | 11/2002 | Douglas et al. |
| 2002/0177890 | A1 | 11/2002 | Lenker |
| 2002/0183832 | A1 | 12/2002 | Penn et al. |
| 2002/0188341 | A1 | 12/2002 | Elliott |
| 2002/0193867 | A1 | 12/2002 | Gladdish, Jr. et al. |
| 2002/0198588 | A1 | 12/2002 | Armstrong et al. |
| 2003/0009211 | A1 | 1/2003 | DiCarlo |
| 2003/0009212 | A1 | 1/2003 | Kerr |
| 2003/0014101 | A1 | 1/2003 | Harrison |
| 2003/0050684 | A1 | 3/2003 | Abrams et al. |
| 2003/0050686 | A1 | 3/2003 | Raeder-Devens et al. |
| 2003/0074048 | A1 | 4/2003 | Sherry |
| 2003/0074050 | A1 | 4/2003 | Kerr |

OTHER PUBLICATIONS

Lawrence, Jr. et al., "Percutaneous Endovascular Graft: Experimental Evaluation", *Radiology*, 163/2:357–360 (1987).

Mirich et al., "Percutaneously Placed Endovascular Grafts for Aortic Aneurysms: Feasibility Study", *Radiology*, 170/3:1033–1037 (1989).

*Surgical Treatment of Aortic Aneurysms*, Book: by Denton A. Cooley, M.D., published in 1986 by W.B. Saunders Company, West Washington Square, Philadelphia, PA(1986).

Haimovitch and Patterson, "Robust growth is forecast for endovascular repair of AAAs," *BBI Newsletter*, 26:5 (May, 2003).

* cited by examiner 10
13
15
207
258
265
206
53
52
263
261
262
267
268
266
225
226
227
42
12
45
47
46
18
38
37
16
44
51
48
5
32
21
27
22
4
33
30
52
272
17
35
3
11
53
28
14
26
31
23
24
25
2
216
211
76

431
452
454
442
438

442
453
455
438
402
454

472
431
452
411
438
485
471
462
484

404
454
464
476
442
431
465
408
474

453
455
455
438
442
431
454
454

DELIVERY SYSTEM AND METHOD FOR BIFURCATED ENDOVASCULAR GRAFT

RELATED APPLICATIONS

This application is a continuation-in-part of U.S. patent application Ser. No. 09/834,278, filed Apr. 11, 2001, by Michael V. Chobotov et al., entitled "Delivery System and Method for Endovascular Graft," which is incorporated by reference herein in its entirety.

BACKGROUND

The present invention relates generally to a system and method for the treatment of disorders of the vasculature. More specifically, the present invention relates to a system and method for treatment of thoracic or abdominal aortic aneurysm and the like, which is a condition manifested by expansion and weakening of the aorta. Prior methods of treating aneurysm have consisted of invasive surgical methods with graft placement within the affected vessel as a reinforcing member of the artery. However, such a procedure requires a surgical cut down to access the vessel, which in turn can result in a catastrophic rupture of the aneurysm due to the decreased external pressure from the surrounding organs and tissues, which are moved during the procedure to gain access to the vessel. Accordingly, surgical procedures can have a high mortality rate due to the possibility of the rupture discussed above in addition to other factors. Such other risk factors for surgical treatment of aortic aneurysms can include poor physical condition of the patient due to blood loss, anuria, and low blood pressure associated with the aortic abdominal aneurysm. An example of a surgical procedure is described in a book entitled *Surgical Treatment of Aortic Aneurysms* by Denton A. Cooley, M.D., published in 1986 by W. B. Saunders Company.

Due to the inherent risks and complexities of surgical intervention, various attempts have been made to develop alternative methods for deployment of grafts within aortic aneurysms. One such method is the non-invasive technique of percutaneous delivery by a catheter-based system. Such a method is described in Lawrence, Jr. et al. in "Percutaneous Endovascular Graft: Experimental Evaluation", *Radiology* (May 1987). Lawrence described therein the use of a Gianturco stent as disclosed in U.S. Pat. No. 4,580,568. The stent is used to position a Dacron fabric graft within the vessel. The Dacron graft is compressed within the catheter and then deployed within the vessel to be treated. A similar procedure has also been described by Mirich et al. in "Percutaneously Placed Endovascular Grafts for Aortic Aneurysms: Feasability Study", Radiology (March 1989). Mirich describes therein a self-expanding metallic structure covered by a nylon fabric, with said structure being anchored by barbs at the proximal and distal ends.

One of the primary deficiencies of the existing percutaneous devices and methods has been that the grafts and the delivery systems used to deliver the grafts are relatively large in profile, often up to 24 French, and stiff in longitudinal bending. The large profile and relatively high bending stiffness of existing delivery systems makes delivery through the vessels of a patient difficult and can pose the risk of dissection or other trauma to the patient's vessels. In particular, the iliac arteries of a patient are often too narrow or irregular for the passage of existing percutaneous devices. Because of this, non-invasive percutaneous graft delivery for treatment of aortic aneurysm is contraindicated for many patients who would otherwise benefit from it.

What is needed is an endovascular graft and delivery system having a small outer diameter relative to existing systems and high flexibility to facilitate percutaneous delivery in patients who require such treatment. What is also needed is a delivery system for an endovascular graft that is simple, reliable and that can accurately and safely deploy an endovascular graft within a patient's body, lumen or vessel.

SUMMARY

The invention is directed generally to a delivery system for delivery of an expandable intracorporeal device, specifically, an endovascular graft. Embodiments of the invention are directed to percutaneous non-invasive delivery of endovascular grafts which eliminate the need for a surgical cut-down in order to access the afflicted artery or other intracorporeal conduit of the patient being treated. Such a non-invasive delivery system and method result in shorter procedure duration, expedited recovery times and lower risk of complication. The flexible low profile properties of some embodiments of the invention also make percutaneous non-invasive procedures for delivery of endovascular grafts available to patient populations that may not otherwise have such treatment available. For example, patients with small anatomies or particularly tortuous vasculature may be contraindicated for procedures that involve the use of delivery systems that do not have the flexible or low profile characteristics of embodiments of the present invention.

In one embodiment, the delivery system has an elongate shaft with a proximal section and a distal section. The distal section of the elongate shaft includes a portion having an expandable intracorporeal device. An elongate belt support member is disposed adjacent a portion of the expandable intracorporeal device and a belt is secured to the belt support member and circumferentially disposed about the expandable intracorporeal device. The belt member constrains at least a portion of the expandable intracorporeal device. A release member releasably secures the belt in the constraining configuration.

Another embodiment of the invention is directed to a delivery system that has an elongate shaft with a proximal section and a distal section. The distal section of the elongate shaft has an elongate belt support member disposed adjacent a portion of the expandable intracorporeal device. A belt is secured to the belt support member and is circumferentially disposed about the expandable intracorporeal device. The belt has a configuration which constrains the expandable intracorporeal device and a release member releasably secures the belt in the constraining configuration. The belt may constrain any portion of the expandable intracorporeal device, such as a self-expanding portion of the expandable intracorporeal device. A self-expanding portion of the device may include a self-expanding member such as a tubular stent.

In a particular embodiment of the invention, a plurality of belts are secured to various axial positions on the belt support member, are circumferentially disposed about the expandable intracorporeal device and have a configuration which constrains the expandable intracorporeal device. At least one release member releasably secures the belts in the constraining configuration. Each belt can be released by a single separate release member which engages each belt separately, or multiple belts can be released by a single release member. The order in which the belts are released can be determined by the axial position of the belts and the direction of movement of the release member.

Another embodiment of the invention is directed to a delivery system for delivery of a self-expanding endovascular graft with a flexible tubular body portion and at least one self-expanding member secured to an end of the endovascular graft. The delivery system has an elongate shaft having a proximal section and a distal section. The distal section of the elongate shaft has an elongate belt support member disposed within the self-expanding member of the endovascular graft and a belt which is secured to the belt support member adjacent the self-expanding member. The belt is also circumferentially disposed about the self-expanding member and has a configuration which constrains the self-expanding member. A release wire releasably secures ends of the belt in the constraining configuration.

A further embodiment of the invention includes a delivery system for delivery of an endovascular graft with a flexible tubular body portion and a plurality of self-expanding members secured to ends of the endovascular graft. The delivery system has an elongate shaft with a proximal section and a distal section. The distal section of the elongate shaft has an elongate guidewire tube disposed within the endovascular graft in a constrained state. A plurality of shape memory thin wire belts are secured to the guidewire tube respectively adjacent the self-expanding members. The belts are circumferentially disposed about the respective self-expanding members and have a configuration which constrains the respective self-expanding members. A first release wire releasably secures ends of the belts disposed about the self-expanding members at the proximal end of the endovascular graft in a constraining configuration. A second release wire releasably secures ends of the belts disposed about the self-expanding members at a distal end of the endovascular graft in the constraining configuration.

The invention also is directed to a method for deploying an expandable intracorporeal device within a patient's body. The method includes providing a delivery system for delivery of an expandable intracorporeal device including an elongate shaft having a proximal section and a distal section. The distal section of the elongate shaft has an elongate belt support member disposed adjacent a portion of the expandable intracorporeal device and a belt which is secured to the belt support member. The belt is circumferentially disposed about the expandable intracorporeal device and has a configuration which constrains the expandable intracorporeal device. A release member releasably secures the belt in the constraining configuration.

Next, the distal end of the delivery system is introduced into the patient's body and advanced to a desired site within the patient's body. The release member is then activated, releasing the belt from the constraining configuration. Optionally, the delivery system may also have an outer protective sheath disposed about the endovascular graft in a constrained state, the belt in its constraining configuration and at least a portion of the release wire disposed at the belt. In such an embodiment, the method of deployment of an expandable intracorporeal device also includes retraction of the outer protective sheath from the endovascular graft prior to activation of the release member.

In an embodiment of the invention directed to delivery of bifurcated intracorporeal device, an elongate shaft has a proximal section and a distal section. The distal section of the shaft has an elongate primary belt support member and at least one primary belt disposed on the primary belt support member. The primary belt support member is configured to be circumferentially disposed about a bifurcated intracorporeal device and at least partially constrain the device. A primary release member is configured to engage and releasably secure the primary belt in a constraining configuration. At least one elongate secondary belt support member is disposed adjacent the elongate primary belt support member. At least one secondary belt is disposed on the secondary belt support member. This at least one secondary belt is configured to be circumferentially disposed about a bifurcated intracorporeal device and at least partially constrain the device. A secondary release member is configured to engage and releasably secure the secondary belt in a constraining configuration.

In a method for deploying a bifurcated intracorporeal device within a patient's body, a delivery system for delivery and deployment of a bifurcated intracorporeal device is provided. The delivery system includes an elongate shaft having a proximal section and a distal section. The bifurcated intracorporeal device is disposed on the distal section of the elongate shaft. The distal section of the elongate shaft also includes an elongate primary belt support member and at least one primary belt secured to the primary belt support member. The primary belt is configured to be circumferentially disposed about a bifurcated intracorporeal device and at least partially constrain the device. A primary release member engages and releasably secures the primary belt in the constraining configuration. The distal section of the elongate shaft also includes at least one elongate secondary belt support member disposed adjacent the elongate primary belt support member. At least one secondary belt is secured to the secondary belt support member and is configured to be circumferentially disposed about a bifurcated intracorporeal device to at least partially constrain the device. A secondary release member engages and releasably secures the secondary belt in a constraining configuration.

The distal end of the delivery system is introduced into the patient's body and advanced to a desired site within the patient's body. The release members are then activated to release the belts from the constraining configuration and the device is deployed. Thereafter, the delivery system can be removed from the patient's body. In some embodiments of the invention, the secondary belt support member is detached and removed from the delivery system prior to withdrawal of the delivery system from the patient. In another embodiment, the secondary belt support member is displaced laterally towards the primary belt support member so as to be substantially parallel to the primary belt support member and enable withdrawal of the delivery system through an ipsilateral side of the bifurcated intracorporeal device.

DETAILED DESCRIPTION

FIGS. 1–8 and 10 illustrate an embodiment of delivery system 10 for delivering a variety of expandable intracorporeal devices; specifically, an expandable endovascular graft 11. One such expandable endovascular graft 11 useful for delivery and deployment at a desired site within a patient is disclosed in co-pending U.S. patent application Ser. No. 09/133,978, filed Aug. 14, 1998, by M. Chobotov, which is hereby incorporated by reference in its entirety.

Figure 1:
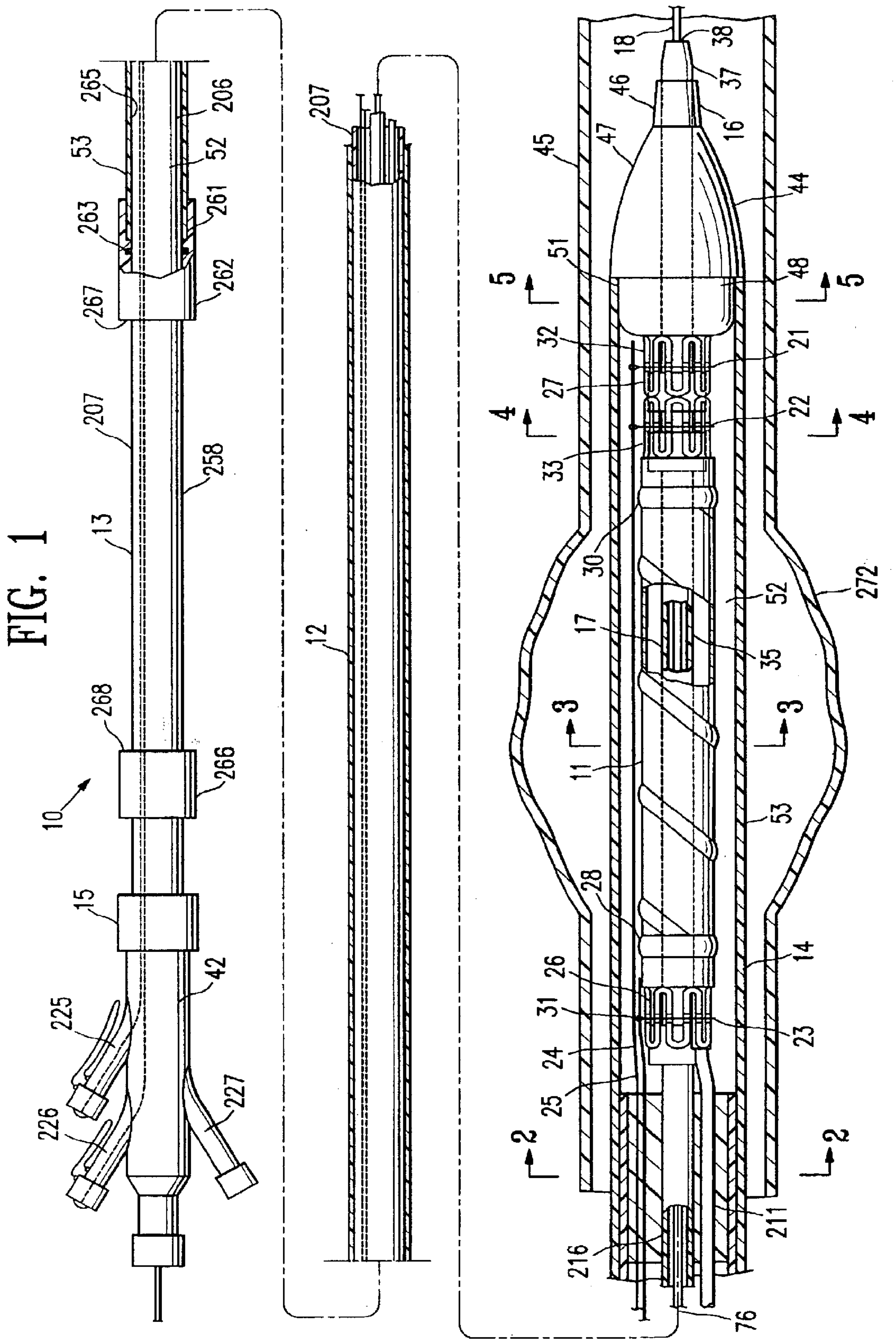
FIG. 1 is an elevational view in partial longitudinal section illustrating an embodiment of a delivery system for an expandable intracorporeal device having features of the invention.

Delivery system 10 in FIG. 1 has an elongate shaft 12 with a proximal section 13, a distal section 14, a proximal end 15 and a distal end 16. The distal section 14 has an elongate belt support member in the form of a guidewire tube 17 disposed adjacent a portion of the expandable endovascular graft 11. A guidewire 18 is disposed within guidewire tube 17. A plurality of belts 21, 22, and 23 are secured to the guidewire tube 17 and are circumferentially disposed about portions of the endovascular graft 11. FIG. 1 shows the belts in a configuration that constrains the endovascular graft 11. First and second release members 24 and 25 (such as release wires) releasably secure belts 21, 22, and 23 in a constraining configuration as shown.

The endovascular graft 11 has a proximal end 26, a distal end 27, a proximal inflatable cuff 28, a distal inflatable cuff 30, a proximal self-expanding member 31, a first distal self-expanding member 32 and a second distal self-expanding member 33. As defined herein, the proximal end of the elongate shaft is the end 15 proximal to an operator of the delivery system during use. The distal end of the elongate shaft is the end 16 that enters and extends into the patient's body. The proximal and distal directions for the delivery system 10 and endovascular graft 11 loaded within the delivery system 10 as used herein are the same. This convention is used throughout the specification for the purposes of clarity, although other conventions are commonly used. For example, another useful convention defines the proximal end of an endovascular graft as that end of the graft that is proximal to the source of blood flow going into the graft. Such a convention is used in the previously discussed co-pending patent application Ser. No. 09/133,978, although that convention is not adopted herein.

Figure 2:
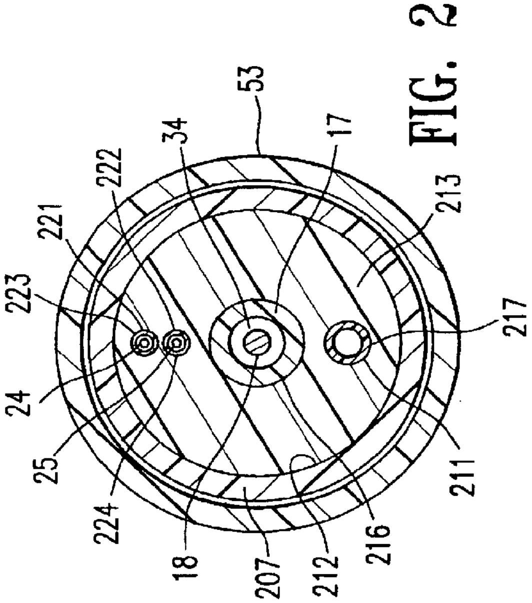
FIG. 2 is a transverse cross sectional view of the delivery system of FIG. 1 taken along lines 2—2 of FIG. 1.
Figure 8:
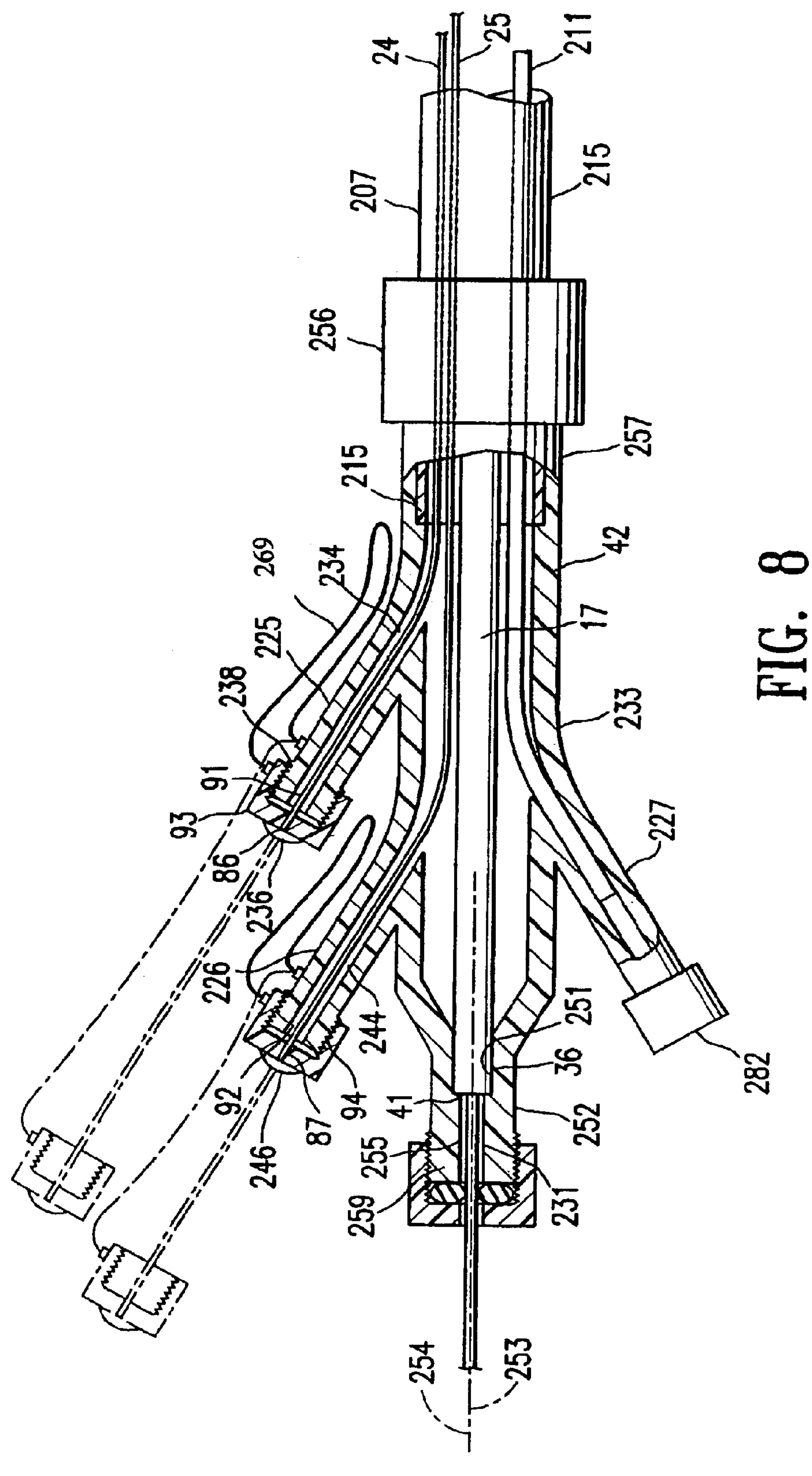
FIG. 8 is an elevational view in partial section of the proximal adapter shown in FIG. 1.
Figure 10:
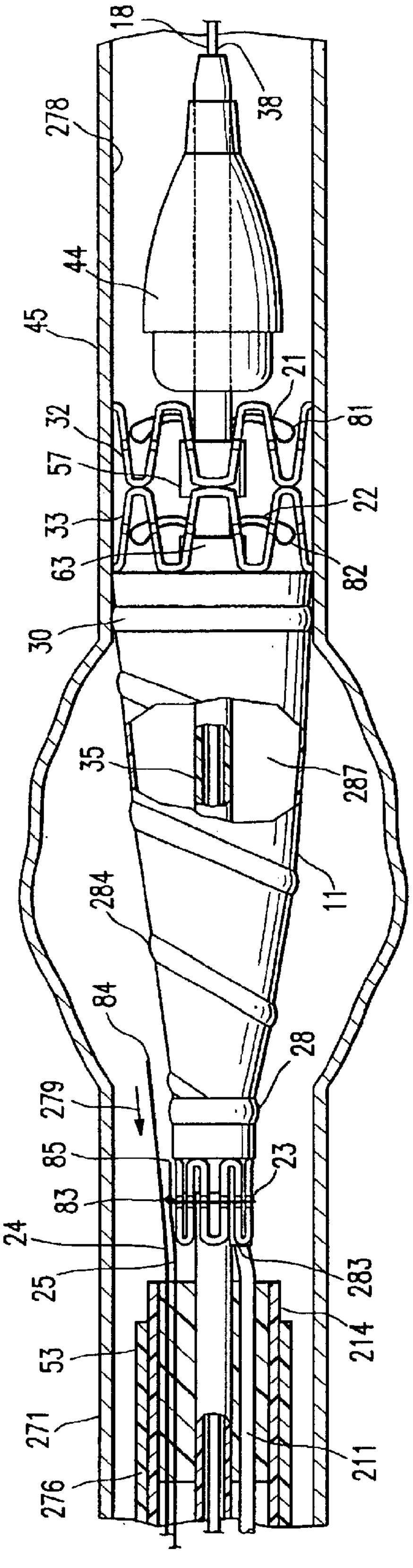
FIG. 10 is a diagrammatic view of a delivery system having features of the invention disposed within an artery of a patient with an expandable intracorporeal device being deployed within the artery.

The guidewire tube 17 has an inner lumen 34, as shown in FIG. 2, a distal section 35, a proximal end 36, as shown in FIG. 8, and a distal end 37. The inner lumen 34 of the guidewire tube 17 terminates at the distal end 37 with a distal guidewire tube port 38, as shown in FIG. 10. As seen in FIG. 8, the proximal end 36 of guidewire tube 17 terminates in a port 41 disposed in the proximal adapter 42. The port 41 is typically a tapered fitting such as a Luer lock fitting which facilitates the attachment of a hemostasis valve (not shown). The guidewire tube 17 is a hollow tubular member that normally has an annular cross section, although oval cross-sectional profiles and others are also suitable.

Figure 5:
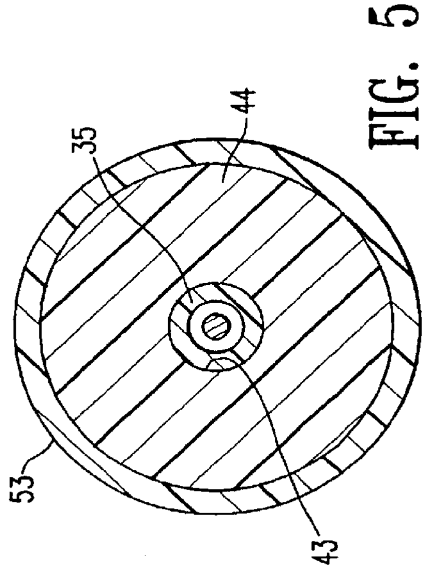
FIG. 5 is a transverse cross sectional view of the delivery system of FIG. 1 taken along lines 5—5 of FIG. 1.

A portion of the distal section 35 of the guidewire tube 17, shown in FIG. 1, is disposed within an inner lumen 43 of a distal nose piece 44, as shown in FIG. 5. Distal nose piece 44 is configured in a streamlined bullet shape for easy passage within a patient lumen or vessel such as aorta 45. Guidewire tube 1 7 may be bonded to the inner lumen 43 of the nose piece 44, or it may be molded into the nose piece 44 during manufacture. Referring to FIG. 1, the nose piece 44 has a distal portion 46, an intermediate portion 47 and a proximal shoulder portion 48 configured to slidingly engage the distal portion 51 of an inner lumen 52 of an outer tubular member 53.

Referring to FIGS. 1, 6A, 6B and 7A, on the distal section 35 of guidewire tube 17, proximal to the proximal shoulder portion 48 of nose piece 44, a first distal belt 21 is secured to the guidewire tube 17. The first distal belt may be secured to the guidewire tube 17 with any suitable adhesive such as cyanoacrylate, epoxy or the like. Both free ends 55 and 56 of the first distal belt 21 are secured to the guidewire tube 17. The guidewire tube 17 may be made from a variety of suitable materials including polyethylene, teflon, polyimide and the like.

Referring to FIGS. 2–5, the inner lumen 34 of the guidewire tube 17 has an inside diameter that can accommodate a guidewire suitable for guiding a device such as delivery system 10. The inner lumen 34 of the guidewire tube 17 may have an inside diameter of about 0.015 inch to about 0.045 inch; specifically, about 0.020 inch to about 0.040 inch. The outer diameter of the guidewire tube 17 may range from about 0.020 inch to about 0.060 inch; specifically, about 0.025 inch to about 0.045 inch.

Figures 6A, 6B:
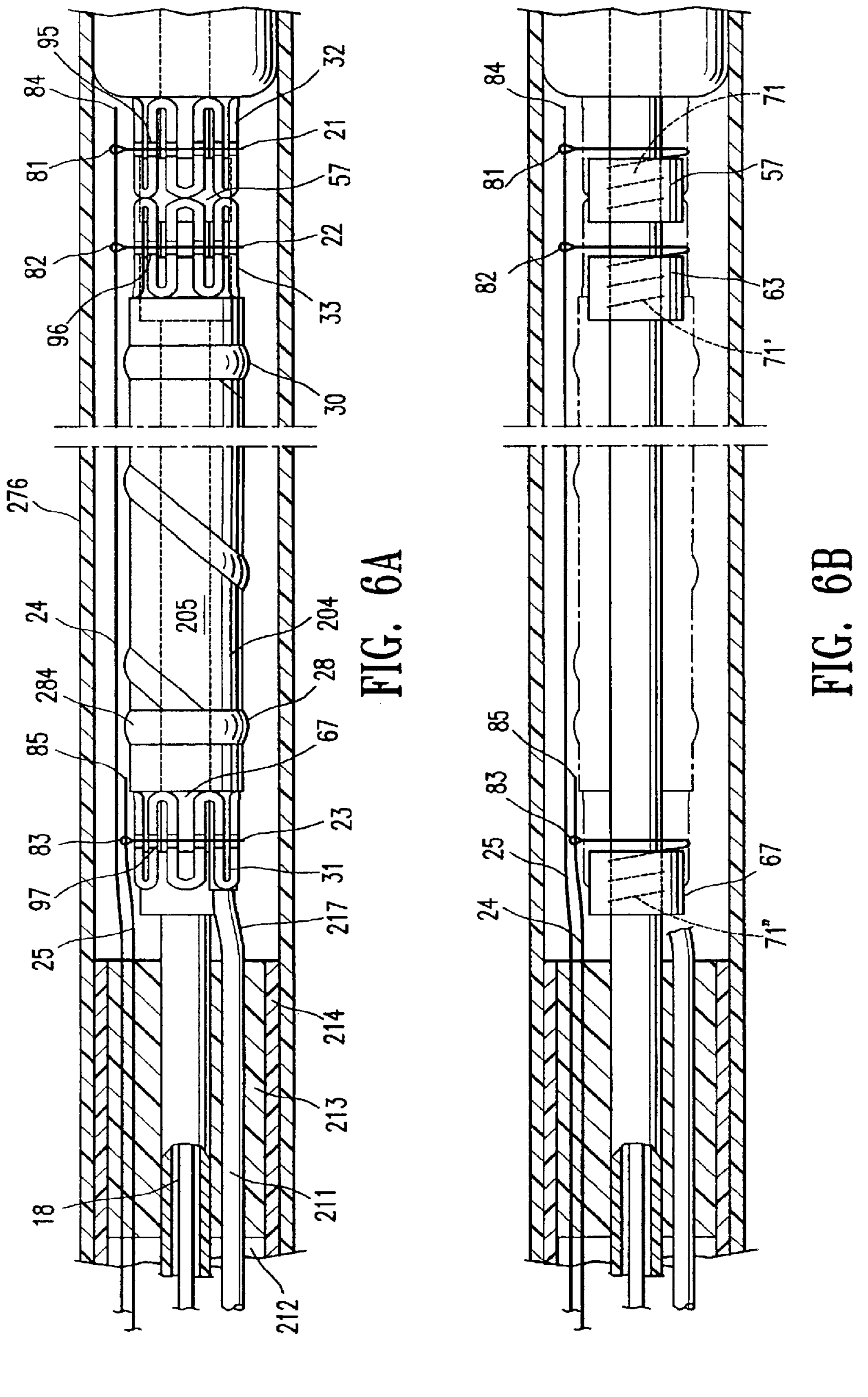
FIG. 6A is an enlarged elevational view in partial section of the delivery system in FIG. 1.
FIG. 6B is an enlarged elevational view in partial section of the delivery system of FIG. 1 with portions of the graft and self-expanding members cut away for clarity of view of the belt bushings.

Referring again to FIGS. 6A, 6B and 7A, an optional first distal belt bushing 57 is disposed about the guidewire tube 17 so as to cover the portions of the free ends 55 and 56 of the first distal belt 21 that are secured to the distal section 35 of the guidewire tube 17. This bushing 57 may also serve to control the constrained configuration of the belted self-expanding members, and may include geometric features to engage or support the belted members. A similar configuration is present at a second distal belt 22 which has free ends secured to the guidewire tube 17 proximal to the first distal belt 21. A second distal belt bushing 63 is disposed about the guidewire tube 17 so as to cover the portions of the free ends of the second distal belt 22 that are secured to the guidewire tube 17. A proximal belt 23 has free ends secured to the guidewire tube 17 proximal to the second distal belt 22 and has an optional proximal belt bushing 67, as shown in FIG. 6B, configured similarly to the first and second distal belt bushings 57 and 63.

The belts 21, 22 and 23 can be made from any high strength, resilient material that can accommodate the tensile requirements of the belt members and remain flexible after being set in a constraining configuration. Typically, belts 21, 22 and 23 are made from solid ribbon or wire of a shape memory alloy such as nickel titanium or the like, although other metallic or polymeric materials are possible. Belts 21, 22 and 23 may also be made of braided metal filaments or braided or solid filaments of high strength synthetic fibers such as Dacron®, Spectra or the like. An outside transverse cross section of the belts 21, 22 and 23 may range from about 0.002 to about 0.012 inch, specifically, about 0.004 to about 0.007 inch. The cross sections of belts 21, 22 and 23 may generally take on any shape, including rectangular (in the case of a ribbon), circular, elliptical, square, etc.

In general, we have found that a ratio of a cross sectional area of the belts to a cross sectional area of the release members, 24 and 25, of about 1:2 is useful to balance the relative strength and stiffness requirements. Other ratios, however, may also be used depending on the desired performance characteristics.

Figure 4:
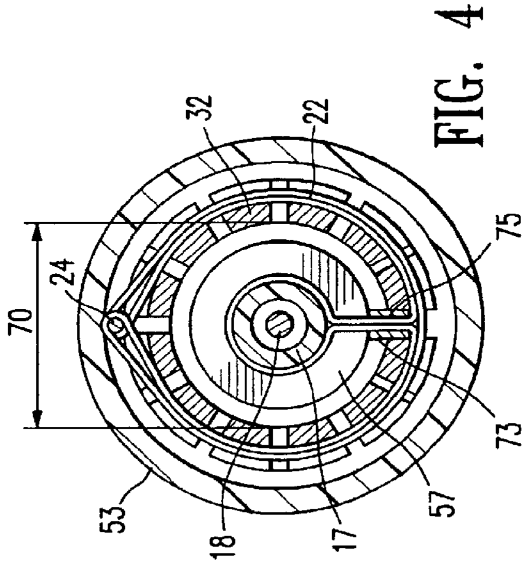
FIG. 4 is a transverse cross sectional view of the delivery system of FIG. 1 taken along lines 4—4 of FIG. 1.
Figure 7B:
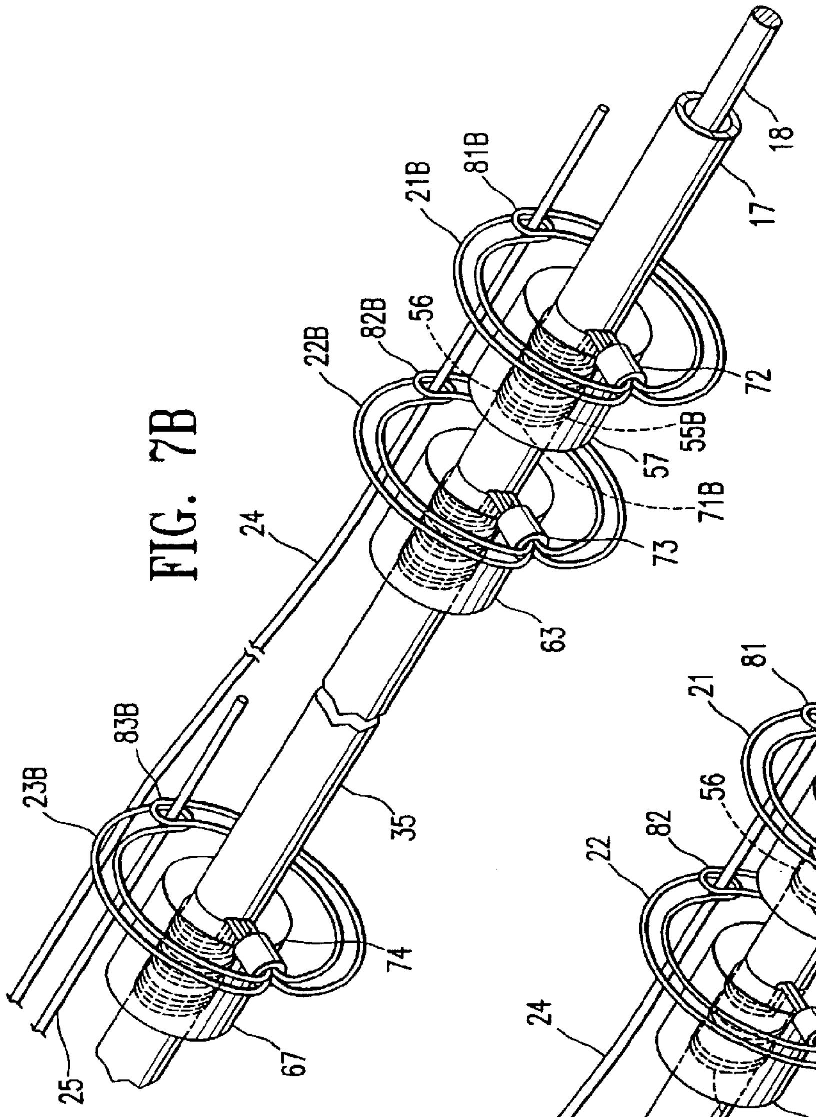
FIG. 7B is a perspective view showing an alternative embodiment of release belts.
Figure 7A:
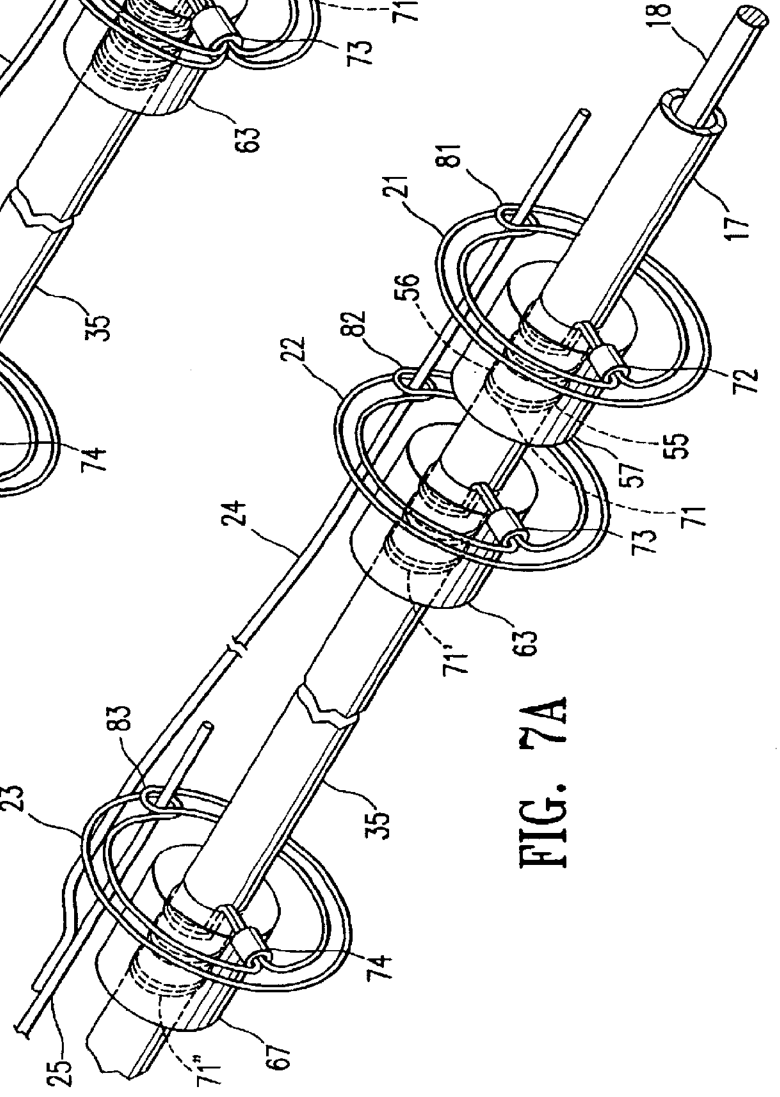
FIG. 7A is a perspective view showing release belt configurations having features of the invention.

The inner diameters of belt bushings 57, 63 and 67 are sized to have a close fit over the guidewire tube 17 and secured portion 71, as shown in FIG. 7A, of the free ends of the belts 21, 22 and 23 that are secured to the guidewire tube 17. Typically, the inner diameter of the belt bushings 57, 63 and 67 range from about 0.025 inch to about 0.065 inch; specifically, about 0.030 inch to about 0.050 inch. In addition, the outer diameter of belt bushing 57 may be sized to approximate an inner diameter 70, as shown in FIG. 4, of the respective first distal self-expanding member 32 of the endovascular graft 11 when the member 32 is in a fully constrained state. The other belt bushings 63 and 67 may be similarly configured with respect to the second distal self-expanding member 33 and the proximal self-expanding member 31.

Such an arrangement keeps the self-expanding members 31, 32 and 33 properly situated when in a constrained state and prevents the various portions of the self-expanding members 31, 32 and 33 from overlapping or otherwise entangling portions thereof while in a constrained state. The outer diameter of the belt bushings 57, 63 and 67 may range from about 0.040 inch to about 0.200 inch; specifically, about 0.060 inch to about 0.090 inch. The material of the belt bushings 57, 63 and 67 may be any suitable polymer, metal, alloy or the like that is bondable. Generally, the belt bushings 57, 63 and 67 are made from a polymer such as polyurethane, silicone rubber or PVC plastic.

As shown in FIG. 7A, belts 21, 22 and 23 extend radially from the guidewire tube 17 through optional standoff tubes 72, 73 and 74. Standoff tubes 72, 73 and 74 are disposed about belts 21–23 adjacent the guidewire tube 17 and act to prevent separation of belts 21–23 in a circumferential direction as tension is applied to the belts. Standoff tubes 72–74 also prevent belts 21–23 from applying other undesirable forces on portions of the endovascular graft 11 that are constrained by the belts. Specifically, the standoff tubes 72–74 prevent the belts 21–23 from spreading the self-expanding members 31–33, or portions thereof, at those locations where the belts 21–23 extend radially through the self-expanding members.

The standoff tubes 72–74 typically have a length substantially equal to a single wall thickness of the self-expanding members 31, 32 and 33. The length of the standoff tubes 72–74 may range from about 0.010 inch to about 0.030 inch. An inner diameter of an inner lumen 75 of the standoff tubes, as shown in FIG. 4, may range from about 0.004 to about 0.024 inch, with a wall thickness of the standoff tubes being about 0.002 inch to about 0.006 inch. Typically, the standoff tubes 72–74 are made from a high strength metal or alloy such as stainless steel, although they may be polymeric as well.

Belts 21–23 exit the outer apertures of standoff tubes 72–74 and extend circumferentially about the respective portions of the expandable intracorporeal device 11. The term "circumferential extension" as used with regard to extension of the belts 21–23 is meant to encompass any extension of a belt in a circumferential direction. The belts may extend circumferentially a full 360 degrees, or any portion thereof. For example, belts or belt segments may extend partially about an endovascular device, and may be combined with other belts or belt segments that also partially extend circumferentially about an endovascular device. Typically, a plane formed by each of the belts 21–23 when in a constraining configuration is generally perpendicular to a longitudinal axis 76, shown in FIG. 1, of the distal section 14 of shaft 12. As shown in FIGS. 6A and 6B, loop ends 81, 82 and 83 of the belts 21, 22 and 23, respectively, are releasably locked together by one or more release members. For example, in the embodiment shown in FIG. 1, a release member in the form of a first release wire 24 is shown disposed within end loops 81 of the first distal belt 21 and end loops 82 of the second distal belt 22 so as to secure the first and second distal belts 21 and 22 in a constraining configuration about the endovascular graft 11. Another release member in the form of a second release wire 25 is shown disposed within end loops 83 of the proximal belt 23 so as to secure the proximal belt 23 in a constraining configuration about the endovascular graft 11.

A single release wire may also be used to perform the function of each of the first and second release wires, 24 and 25, so that first distal belt 21, second distal belt 22, and proximal belt 23 may be releasably secured by a single release wire. A highly controlled, sequential belt deployment scheme may be realized with the use of a single release wire.

Any number of release wires and belts as may be needed to effectively secure and deploy graft 11, in combination, are within the scope of the present invention.

In some embodiments of the invention, when constrained, the end loops of any single belt touch each other or are spaced closely together such that the belt as a whole forms a substantially circular constraint lying substantially in a plane. Release wire 24 and 25 may be made from suitable high strength materials such as a metal or alloy (e.g., stainless steel) which can accommodate the torque force applied to the release wire by the belt end loops 83 when the belts 23 are under tension from the outward radial force of the constrained portions of the endovascular graft 11, i.e., the self-expanding members 32 and 33.

The release wires 24 and 25 may generally have an outer diameter ranging from about 0.006 to about 0.014 inch. Distal end portions 84 and 85 of release wires 24 and 25, respectively, may terminate at any appropriate site distal of the end loops 81–83 of belts 21–23. As shown in FIG. 8, the proximal ends 86 and 87 of the release wires 24 and 25 extend through the elongate shaft 12 of the delivery system 10 through proximal ports 91 and 92 on the proximal adapter 42, respectively, and terminate at respective release wire handles 93 and 94 which are releasably secured to the proximal adapter 42.

FIG. 7B illustrates an alternative embodiment of the belts 21–23 of FIG. 7A. In FIG. 7A, belts 21–23 are shown as each consisting of a single strand of wire formed into the end loops 81–83, respectively, with the end loops in an overlapping configuration. Free ends 55 and 56 of belt 21 are shown secured to the distal section 35 of the guidewire tube 17. In contrast, FIG. 7B, wherein like elements with regard to FIG. 7A are shown with like reference numerals, shows belts 21B, 22B and 23B formed of two strands of wire, with each strand formed into a single loop which overlaps a loop of the other strand to form end loops 81B, 82B and 83B. The free ends of the belts 21B–23B may be secured in a similar manner to those of free ends 55 and 56 of FIG. 7A.

Figure 7D:
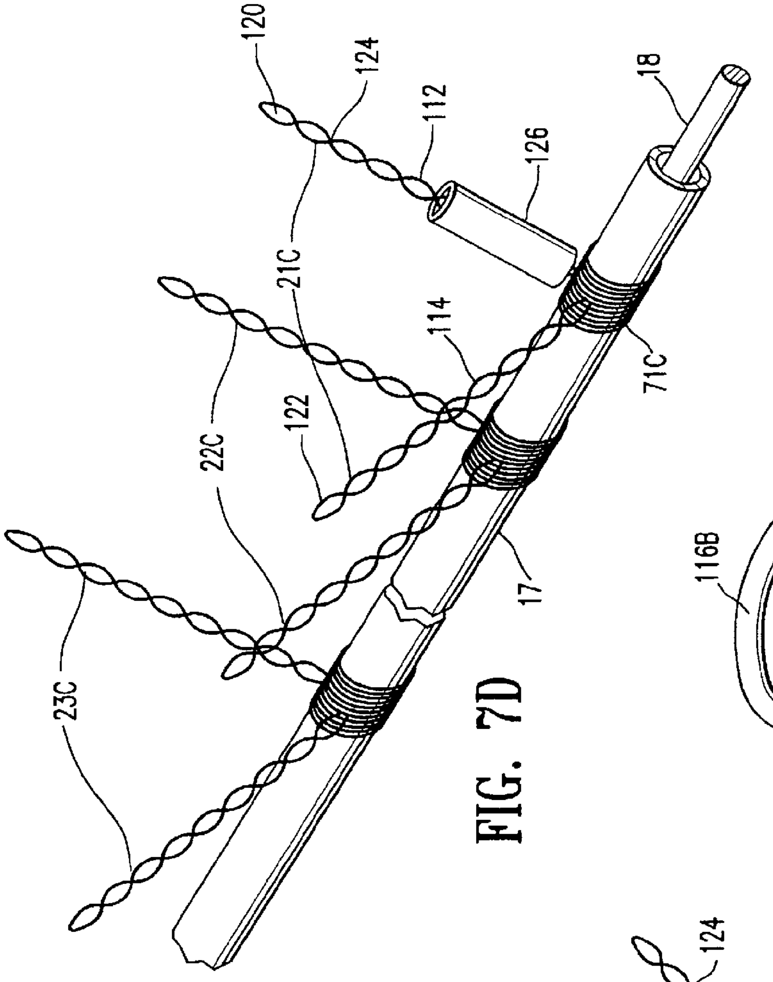
FIG. 7D is a perspective view of the embodiment of FIG. 7C.
Figure 7F:
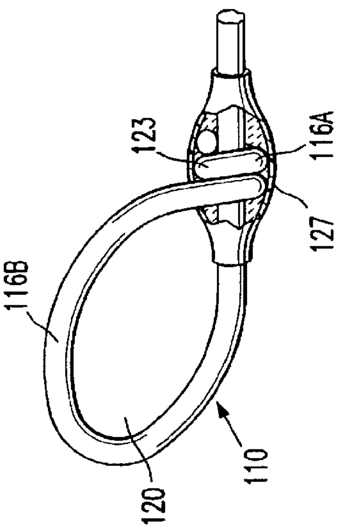
FIG. 7F is a perspective view, partially cut away, of a particular embodiment of an end loop of a release belt.
Figure 7E:
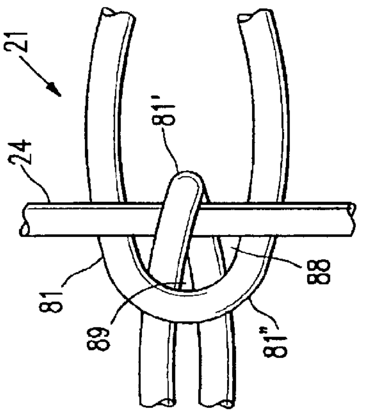
FIG. 7E is an enlarged view of a particular coupling configuration between end loops of release belts.
Figure 7C:
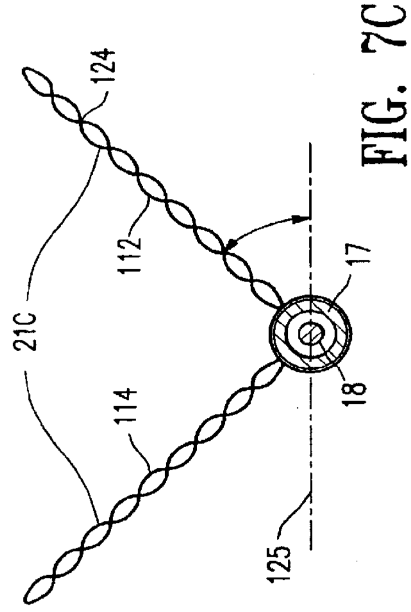
FIG. 7C is an end view showing an alternative embodiment of release belts.

Turning now to FIGS. 7C and 7D, alternative embodiments for portions of the delivery system of the present invention are shown. FIGS. 7C and 7D illustrate alternative belts 21C, 22C and 23C disposed on guidewire tube 17. Single or multiple belts 21C–23C may be deployed at various locations along guidewire tube 17 as desired. In addition, the members comprising belts 21C–23C are shown as a single line. However, belts 21C–23C may be of a single- or multiple strand or filament design with various cross-sectional shapes as previously described. A single solid ribbon or wire is particularly useful.

Belts 21C–23C shown in FIGS. 7C and 7D are a single strand filament wrapped around guidewire tube 17 and fixed thereon via any number of suitable techniques, such as gluing with adhesive, mechanical fixation, etc. Especially useful is fixing the belt with an ultraviolet-curable adhesive.

Alternatively, belts 21C–23C may comprise two strand filaments each wrapped around guidewire tube 17 so that, for instance, belt 21C is a two-filament component.

Belt 21C includes belt arms 112 and 114, each of which, in the embodiments shown, is a loop of filament twisted upon itself to form a helix. Any number of twists may be imparted to arms 112 and 114 to provide a relatively loose or relatively tight helix as desired. Typically the number of twists (with a single twist being defined as a single overlap of wire segment) in each belt arm 112 and 114 numbers from zero to about 50 or more; specifically, about two to about 10. The choice of material used for belt 21C is an important factor in determining the optimum number of twists for each belt arm. Belt arms 112 and 114 may be formed into other configurations (e.g., braid, double helix, etc.) as well.

Disposed within the end loops of the belt arms 112 and 114 are distal apertures or openings 120, 122, respectively. During assembly of the delivery system, a release wire (such as wire 24) is passed through each aperture 120, 122 after the belt arms are wrapped around the graft self-expanding member, preferably in a circumferential groove as further described below. The release wire may also be disposed through any aperture created along the length of belt arms 112, 114 by each helix twist, although the distal-most apertures 120, 122 are preferred.

The wire optionally may be welded, glued, or otherwise fixed to itself at discrete points or along all or any portion of belt arms 112, 114, save their corresponding apertures 120 and 122. For instance, the belt arm wire may be glued or welded to itself at the overlap or twist points, such as points 124.

FIG. 7D shows an optional belt arm sleeve 126 that may be used to enclose a portion of one or both belt arms 112, 114, or any of the other belt embodiments contemplated herein. Belt 112 is shown in FIG. 7D being constrained or covered over a length thereof by a flexible sleeve or coating 126 (or alternatively, a coil wrapping or by fixing the loop to itself by adhesives, welding, soldering, brazing, etc.). Sleeve or coating 126 may optionally be shrink-wrapped, crimped, or otherwise configured to constrain or cover belt arm 112 therein. These fixation and sleeve features help to minimize the potential of belt arm untwisting and tend to close or block some or all of the helix apertures along the length except those through which the release wire are intended to pass. They can also provide greater structural and operational stability to the catheter system as a whole.

Belt arm sleeve 126 can be configured to have a transverse dimension that is sized to fit a twisted belt arm with fixed nodal points such as the belt arm 112 shown in FIG. 7D. In order to accommodate such a twisted belt arm 112, the inner diameter and outer diameter would be large relative to a transverse dimension of the wire material that forms the belt arm 112. However, the belt arm sleeve 126 can also be only slightly larger in transverse dimension that the wire that forms the belt arm. For example, embodiments of belt arms that do not have twisted wires may have a sleeve 126 that fits closely or tightly over two strands of wire forming a belt arm. The sleeve 126 can cover substantially the entire length of such an untwisted belt arm from at least the guidewire tube to just proximal of the distal loop, such as distal loop 120. The distal loop should remain exposed for engagement by a release wire. In such an embodiment, the sleeve covered portion of the belt arm may also be wrapped around and secured to the guidewire tube just as the unsleeved belt portion of the belt arm 112 shown in FIG. 7D is shown at 71C. This type of low profile belt arm sleeve may also be used to cover twisted belt arm embodiments, although a slightly larger diameter sleeve would be required.

It may be desirable to impart a particular free resting angle to the belt arms 112, 114 to improve the reliability of the system and further reduce the possibility of the arms 112 and 114 interfering with other components of the prosthesis or delivery system. The FIG. 7C view shows belt arms 112, 114 symmetrically disposed at an angle α as measured from a horizontal plane 125. This angle a may range from zero to 180 degrees. For example, one or both belt arm 112, 114 may lie along plane 125 or they may rest in the configuration shown (α=45 degrees). Any known techniques may be used to impart a desired resting configuration to the system, such as, for example, cold working or shape-setting by way of an athermal phase transformation (in the case of shape memory alloys).

Figure 7G:
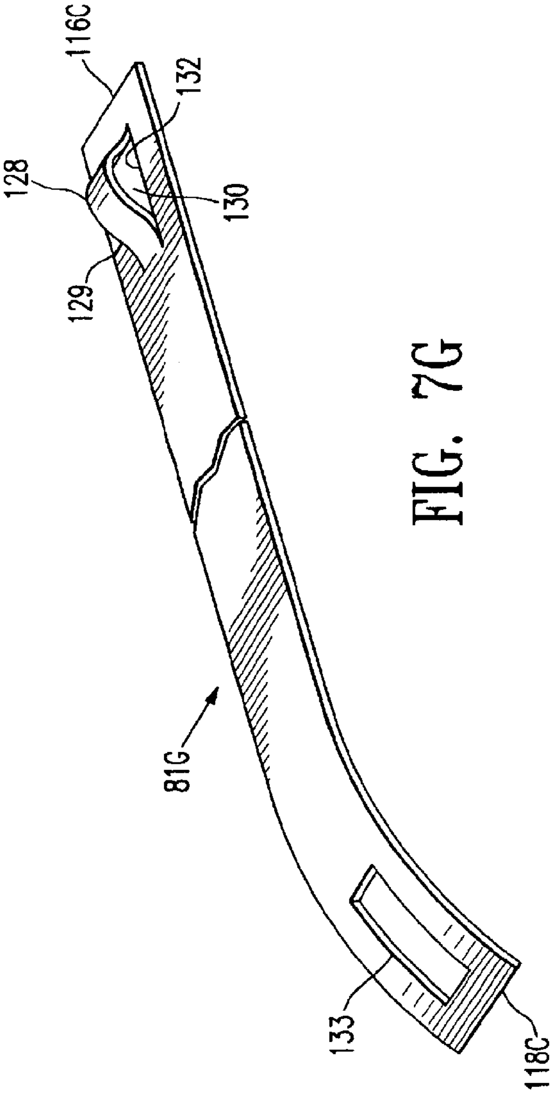
FIG. 7G is a perspective view of an alternative embodiment of a release belt.
Figure 7H:
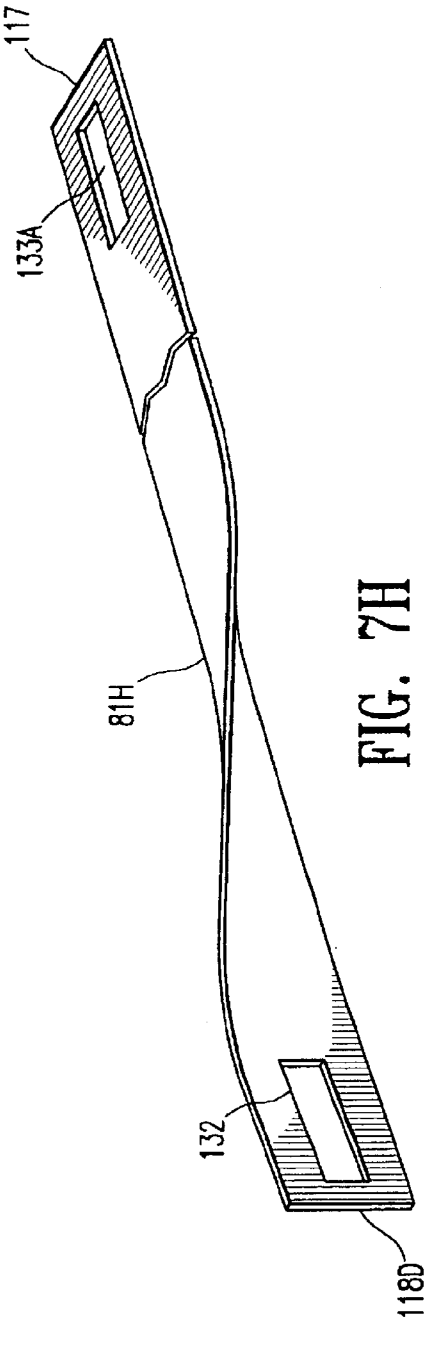
FIG. 7H is a perspective view of an alternative embodiment of a release belt.
Figure 7I:
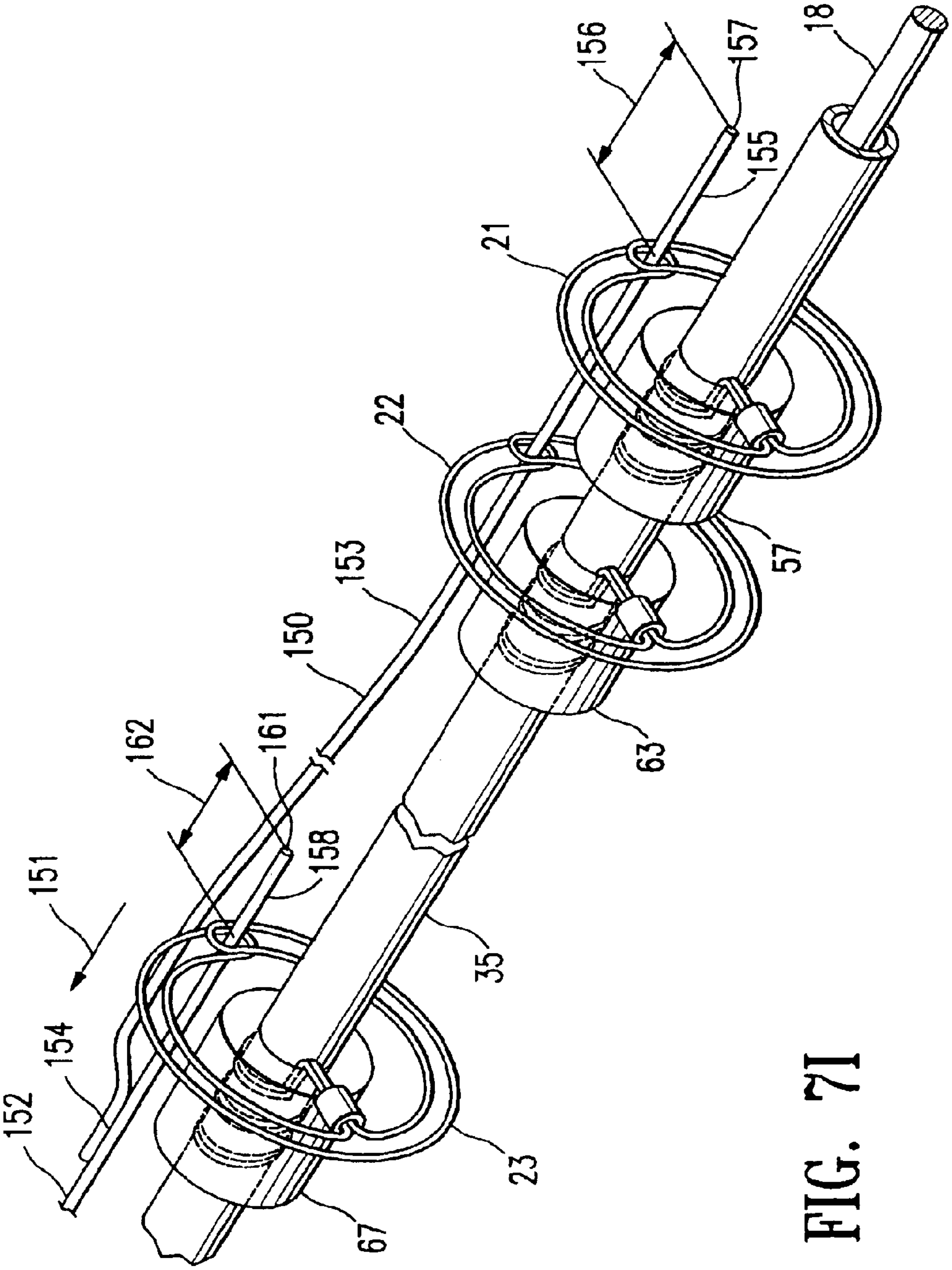
FIG. 7I is a perspective view of an alternative embodiment of a branched release wire.
Figure 7K:
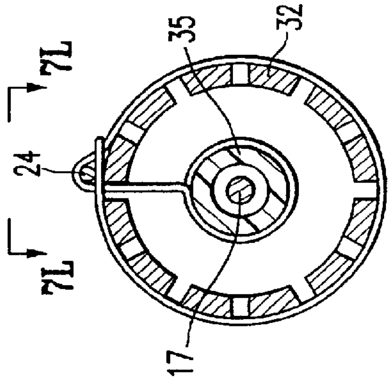
FIG. 7K is a transverse cross sectional view showing the alternative embodiment of the release belt configuration of FIG. 7J constraining a self-expanding member.
Figure 7L:
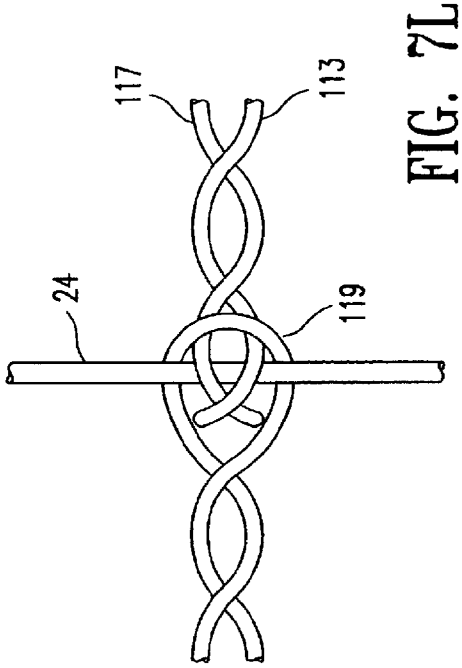
FIG. 7L is a detail of the connection formed where a release wire is used with the alternative release belt embodiment of FIGS. 7J–7K.
Figure 7J:
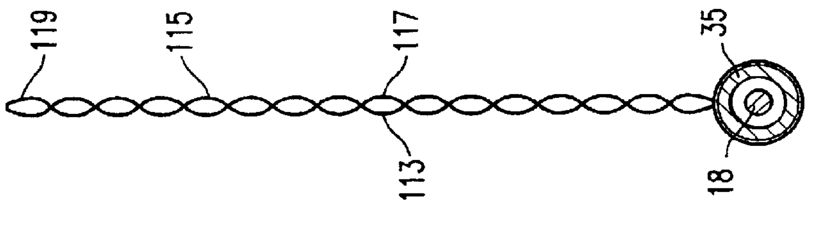
FIG. 7J is an end view showing an alternative embodiment of a release belt.

FIG. 7J shows a single belt example of the version shown in FIGS. 7C and 7D. Here, a single belt arm 113 is shown disposed about the distal section 35 of guidewire tube 17. Belt arm 113 is significantly longer than either belt arm 112 or 114 of the FIGS. 7C–7D embodiment so that it may extend at least around the circumference of any one of self-expanding members 31, 32, or 33. The distal portion 115 of belt arm 113 meets a more proximal portion 117 where one or both strands (when the belt arm 113 is a twisted variety) extends through an end loop 119 in the belt arm 115 distal portion. As discussed with other embodiments, a release member such as release wire 24 may be inserted through end loop 119 and the intersecting portion of the belt arm proximal portion 117 to releasably secure belt arm 113 in a constraining configuration about the endovascular graft 11. FIG. 7K depicts a simplified schematic cross-sectional view of belt arm 113 (shown here untwisted) held in place by a release wire 24 about an exemplary self-expanding member 32. FIG. 7L is a detail of the connection formed where release wire 24 intersects the distal and proximal portions, 115 and 117, respectively, of belt arm 113.

All of the features discussed herein with respect to the, FIGS. 7C–7D embodiment may be employed in the embodiment of FIGS. 7J–7K as well.

This helix configuration shown in the embodiments of FIGS. 7C–7D and 7J–7L is a particularly reliable configuration. It reduces the possibility that a portion of belt 21C becomes entangled with a self-expanding member (such as members 31, 32 and 33) or otherwise interferes with the safe and effective deployment of the prosthesis.

FIG. 7E depicts a particularly useful arrangement for configuring the belt end loops 81–83 with release wires 24–25 during assembly of delivery system 10. In this example, first and second end loops 81' and 81" of belt 21 are shown connected via release wire 24. To achieve the configuration of FIG. 7E, first end loop 81' is passed through aperture 88 disposed in second end loop 81". A portion of aperture 89 disposed in first end loop 81' should extend through the plane created by second end loop 81" as shown in FIG. 7E.

Next, release wire 24 is passed through the portion of aperture 89 that extends beyond this plane so that wire 24 "locks" the two looped ends 81' and 81" together as shown. We have found that this is a stable configuration that lends itself well to a reliable and safe deployment protocol.

Other techniques for assembling wire 24 and first and second end loops 81' and 81" may be used; the method described above is merely exemplary. Wire 24 may simply pass through loop ends as configured and as shown at reference numerals 81, 82 and 83 in FIG. 7A, and 81B, 82B and 83B of FIG. 7B as well.

In the embodiment of FIG. 7F, belt 110 is a member in the shape of a wire formed into an end loop 116B having an aperture 120 for receiving a release wire. This arrangement may be used on one or both ends of belt 110 or, alone if belt 110 is in the form of a single belt arm as discussed above. Connection 122 is shown in FIG. 7F as a simple wrapping of the distal end 116A of the wire comprising belt 110. Connection 122 need not be limited to such a tapered or cylindrical sleeve or coating, however. Other methods to form end loop 116B are contemplated, including, for example, the use of adhesives, welding, brazing, soldering, crimping, etc. An optional protective sleeve or coating 127 (shown in sectional view in FIG. 7F) covers or is part of connection 122 and serves to protect the patient as well as components of the delivery system and prosthesis from damage.

Turning now to FIGS. 7G and 7H, two alternative embodiments of a ribbon-like belt 81G and 81H are shown. In FIG. 7G, a section 128 of material has been partially displaced from belt 81G distal end 116C and worked into a loop-like member 129 such that two generally orthogonal apertures 130, 132 are formed in belt distal end 116C. A set of hinges or other protective mechanism or material may be used on each end of this section 128 so that further tearing or peeling of this member may be prevented. Section 128 may be formed integrally from the belt distal end 116C as shown in FIG. 7G or may be a separate component that is attached to the belt distal end by any suitable means.

Second belt distal end 118C in FIG. 7G is shown as having an aperture 133 disposed therein. In use, a half-twist is imparted to the ribbon-like belt 81G as the second distal end 118C is brought through aperture 130 such that apertures 132 and 133 are at least partially aligned. A release wire (such as wire 24) is then brought through apertures 132 and 133 to releasably join ends 116C and 118C.

FIG. 7H shows yet another embodiment of a belt 81H where a simple rectangular aperture 133A is disposed in the distal end 117 of belt 81H through which another belt end and release wire may be disposed as taught herein. As with the embodiment of FIG. 7G, a half-twist is imparted to the belt 81H in use so that the second distal end 118D is brought through aperture 133. A release wire may then be threaded through apertures 132 and 133 to releasably join ends 117 and 118D. In this embodiment, aperture 132 should be large enough to accommodate both second distal end 11 8D and a release wire.

FIG. 7I shows a perspective view of a belt assembly similar to that shown in FIG. 7A, wherein like elements are shown with like reference numerals. An alternative embodiment of a release wire consisting of a branched release wire 150 is illustrated in FIG. 7I. The branched release wire 150 engages belts 21–23 and is configured to release belts 21–23 at different times with a proximal withdrawal movement of the branched release wire 150, the direction of which is indicated by arrow 151. Branched release wire 150 has a main portion 152 and a branch portion 153. Branch portion 153 is secured to main portion 152 by a solder joint 154. The joint 154 could also be made by any other suitable means, such as welding, bonding with an epoxy, mechanically binding the joint, or the like. The embodiment of the branched release wire shown in FIG. 71 consists of wire which is generally round in cross section. The wire of the branched release wire can have the same or similar material and mechanical properties to the wire of the release wires 24 and 25 discussed above. Branch portion 153 engages first distal belt 21 and second distal belt 22. A distal segment 155 has a length L indicated by arrow 156 which extends distally from first distal belt 21 to the distal end 157 of branch portion 153.

Main portion 152 of the branched release wire 150 engages the proximal belt 23 and has a distal segment 158 that extends distally from the proximal belt 23 to a distal end 161 of the main portion. The length L' of the distal segment 158 of the main portion 152 is indicated by arrow 162. Length L of distal segment 155 is greater than length L' of distal segment 158. In this way, as the branched release wire is withdrawn proximally, proximal belt 23 is released first, first distal belt 21 is released second and second distal belt is released last. Such a branched release wire allows a wide variety of belt release timing with a single continuous withdrawal or movement of a proximal end (not shown) of the branched release wire 150. The proximal end of the branched release wire may be terminated and secured to a release wire handle or the like, as discussed herein with regard to other embodiments of release wires. The ability to deploy multiple release wires in a desired timing sequence with a single branched release wire 150 gives the designer of the delivery system great flexibility and control over the deployment sequence while making the deployment of the belts simple and reliable for the operator of the delivery system. Although the branched release wire 150 has been shown with only a single branch, any number of branches or desired configuration could be used to achieve the deployment sequence required for a given embodiment of a delivery system. For example, a separate branch could be used for each belt in a multiple belt system, with varying distal segment length used to control the sequence of deployment. Also, multiple branched release wires, or the like, could be used in a single delivery system to achieve the desired results.

A number of embodiments for the belt and belt arm components of the present invention are described herein. In general, however, we contemplate any belt or belt arm configuration in which the belt may be used to releasably hold or restrain an implant member in conjunction with a release member. The particular embodiments disclosed herein are not meant to be limiting, and other variations not explicitly disclosed herein, such as those in which multiple apertures (which may have varying shapes and sizes) are disposed along the belt length, those in which the belt or belt arm distal ends comprises a separate material or element that is affixed to the belt or belt arm, etc. are within the scope of the invention. Furthermore, various embodiments of the ends of the belts or belt arms taught herein may exist in any combination in a single delivery system.

Turning now to FIG. 6A, belts 21–23 lie within circumferential grooves or channels 95, 96 and 97, respectively, formed into the respective self-expanding members 31, 32 and 33. Grooves 95–97 prevent axial displacement of the belts 21–23 prior to activation or release of the releasable members 24 and 25, i.e., proximal retraction of the first and second release wires. Although grooves 95–97 are illustrated in the embodiment shown, other alternatives are possible to achieve the same or similar function of the grooves. For example, abutments extending slightly from the self-expanding members 31–33 on either side of the belts 21–23 in their constraining configuration could prevent axial movement of the belts. A detachable adhesive or the like could also be used.

As shown in FIG. 10, the release of end loops 81–83 occurs when the distal end portions 84 and 85 of the release wires 24 and 25, respectively, pass from within the overlapped end loops 81–83. If the end loops 81–83 move axially in response to movement of the release wires 24 and 25 due to frictional forces imposed on the end loops 81–83 by the release wires, the point at which the distal end portions 84 and 85 pass from within the end loops 81–83 would vary depending on the amount of movement of the end loops 81–83.

If the end loops 81–83 were to be axially displaced from their normal position relative to the distal ends of the release wires prior to deployment, the timing of the release of the belts 21–23 could be adversely affected. Thus, the prevention of axial displacement of the belts 21–23 during proximal retraction of the release wires 24 and 25 facilitates accurate release of the belts by keeping the overlap joint of the belt looped end portions in a constant axial position during such retraction.

In addition, it may be desirable to keep belts 21–23 positioned at or near the general center of a given constrained self-expanding members 31–33 so that the self-expanding member 31–33 is substantially uniformly and evenly constrained over its axial length. If belts 21–23 constrain the self-expanding members 31–33 at a non-centered axial position on the member, an end of the member opposite that of the non-centered position may be less constrained and may interfere with axial movement of the outer tubular member 53 (and consequently deployment of the endovascular graft 11).

Figure 3:
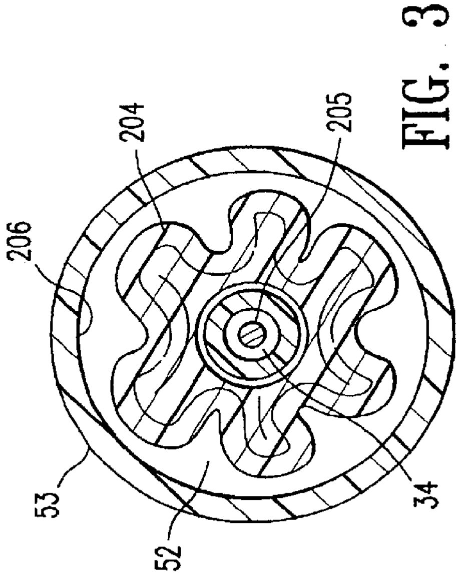
FIG. 3 is a transverse cross sectional view of the delivery system of FIG. 1 taken along lines 3—3 of FIG. 1.

Tubular body member 205 of the endovascular graft 11 is disposed between and secured to the second distal self-expanding member 33 and the proximal self-expanding member 31. The tubular body member comprised of flexible material 204, is shown constrained in an idealized view in FIGS. 1, 3 and 6, for clarity. In practice, tubular body member 205 while constrained is tightly compressed with minimal air space between layers of flexible material 204 so as to form a tightly packed configuration as shown in FIG. 3. Tubular body member 205 is optionally radially constrained by an inside surface 206 of the inner lumen 52 of outer tubular member 53.

An inner tubular member 207 is slidably disposed within the inner lumen 52 of outer tubular member 53. Release wires 24 and 25, guidewire tube 17 and an inflation tube 211 are disposed within an inner lumen 212 of the inner tubular member 207. Inner lumen 212 is optionally sealed with a sealing compound, depicted in FIGS. 1, 2 and 6A by reference numeral 213 at distal end 214. The sealing compound 213 prevents leakage of fluids such as blood, etc., from a proximal end 215, shown in FIG. 8, of the inner tubular member 207. Sealing compound 213 fills the space within the inner lumen 212 of the inner tubular member 207 between an outer surface 216 of the guidewire tube 17, the outer surface 217 of the inflation tube 211 and outer surfaces 221 and 222 of a tubular guide 223 for the first release wire 24 and a tubular guide 224 for the second release wire 25. The sealing compound 213 can be any suitable material, including epoxies, silicone sealer, ultraviolet cured polymers, or the like.

In FIG. 2, the tubular guides 223 and 224 for the first release wire 24 and the second release wire 25 allow axial movement of the release wires with respect to the sealing compound 213 and inner tubular member 207. The inside diameter of the inner lumens of the tubular guides 223 and 224 are sized to fit closely with an outer diameter or transverse dimension of the release wires 24 and 25. Alternatively, tubular guides 223 and 224 may be replaced by a single tubular guide that houses one or more release wires, such as wires 24 and 25.

Turning to FIG. 8, the inner tubular member 207 terminates proximally with the proximal adapter 42 having a plurality of side arms 225, 226 and 227 and a proximal exit port 231 for the inner lumen 34 of the guidewire tube 17. First release wire side arm 225 branches from a proximal adapter body portion 233 and has an inner lumen 234 and proximal end 86 of the first release wire 24. A proximal extremity 236 of the first release wire 24 is anchored to the first release wire proximal handle 93 which is threaded onto the proximal end 238 of the first release wire side arm 225. The proximal extremity 236 of first release wire 24 is configured as an expanded bushing or other abutment that captures the handle 93 and translates proximal axial movement of the handle 93 to the first release wire 24 but allows relative rotational movement between the handle 93 and the proximal end 86 of the first release wire 24.

A similar configuration exists for the proximal end 87 of the second release wire 25. There, a second release wire side arm 226 branches from the proximal adapter body portion 233 and has an inner lumen 244 that houses the proximal end 87 of the second release wire 25 which is free to slide in an axial orientation within the lumen 244. A proximal extremity 246 of the second release wire 25 is configured as an expanded bushing or other abutment that captures the second release wire handle and translates axial proximal movement of the second release wire handle 94 to the second release wire 25, but allows relative rotational movement between the proximal end 87 of the second release wire 25 and the second release wire handle 94.

The first release wire handle 93 and second release wire handle 94 may optionally be color coded by making each, or at least two, release wire handles a color that is distinctly different from the other. For example, the first release wire handle 93 could be made green in color with the second release wire handle 94 being red in color. This configuration allows the operator to quickly distinguish between the two release wire handles and facilitates deployment of the belts in the desired order.

In another embodiment, instead of color coding of the release wire handles 93 and 94, the spatial location of the handles can be configured to convey the proper order of deployment of the release wires to the operator of the delivery system. For example, if three release wire handles are required for a particular embodiment, the corresponding three side arms can be positioned along one side of the proximal adapter. In this configuration, the release wire handle that needs to be deployed first can extend from the distal-most side arm. The release wire handle that needs to be deployed second can extend from the middle side arm. The release wire handle that is to be deployed last can extend from the proximal-most side arm. For such a configuration, the operator is merely instructed to start deployment of the release wires at the distal-most release wire handle and work backward in a proximal direction to each adjacent release wire handle until all are deployed. Of course, an opposite or any other suitable configuration could be adopted. The configuration should adopt some type of spatially linear deployment order, either from distal to proximal or proximal to distal, in order to make reliable deployment of the release wires in the proper order easy to understand and repeat for the operator of the delivery system. Other types of release order indicators such as those discussed above could also be used, such as numbering each release wire handle or side arm with a number that indicates the order in which that handle is to be deployed.

As shown in FIG. 8, the proximal end 36 of the guidewire tube 17 terminates and is secured to an inner lumen 251 of the proximal end 259 of the proximal adapter 42. Inner lumen 251 typically has a longitudinal axis 253 that is aligned with a longitudinal axis 254 of the proximal section 13 elongate shaft 12 so as to allow a guidewire to exit the proximal end 15 of the elongate shaft 12 without undergoing bending which could create frictional resistance to axial movement of the guidewire. A proximal port 255 of the proximal adapter 42 may be directly fitted with a hemostasis valve, or it may be fitted with a Luer lock fitting which can accept a hemostasis valve or the like (not shown).

The proximal adapter 42 may be secured to the proximal end 215 of the inner tubular member 207 by adhesive bonding or other suitable method. A strain relief member 256 is secured to the distal end 257 of the proximal adapter 42 and the inner tubular member 207 to prevent kinking or distortion of the inner tubular member 207 at the joint.

As seen in FIG. 1, the proximal end 261 of the outer tubular member 53 is secured to a proximal fitting 262 that slides over an outer surface 258 of the inner tubular member 207. A seal 263 located in proximal fitting 262 provides a fluid seal for the lumen 265 formed between the outer surface 258 of the inner tubular member 207 and the inner surface 206 of the inner lumen 52 of the outer tubular member 53. The fit between the outer surface 258 of the inner tubular member 207 and the inner surface 206 of the outer tubular member 53 is typically close, but still allows for easy relative axial movement between outer tubular member 53 and inner tubular member 207. A stop 266 is disposed and secured to the outer surface 258 of the inner tubular member 207 distal of the proximal adapter 42 to limit the amount of proximal axial movement of the outer tubular member 53 relative to the inner tubular member 207.

When the outer tubular member 53 is positioned on the proximal shoulder 48 of the distal nose piece 44 prior to deployment of endovascular graft 11, the distance between a proximal extremity 267 of proximal fitting 262 and a distal extremity of stop 266 is approximately equal to or slightly greater than an axial length of the endovascular graft 11 in a constrained state. This configuration allows the outer tubular member 53 to be proximally retracted to fully expose the endovascular graft 11 in a constrained state prior to deployment of the graft. This distance may be greater, but should not be less than the length of the endovascular graft 11 in a constrained state in order to completely free the constrained graft 11 for radial expansion and deployment.

Retraction limiters may alternatively be used to prevent excessive axial movement of the release wires 24 and 25 in a proximal direction during deployment. Particularly in embodiments of the invention where single release wires are used to constrain and deploy multiple belts such as with first release wire 24, retraction limiters may be used to allow enough axial movement of the release wire 24 to deploy a first belt 21, but prevent deployment of a second more proximally located belt 22. For example, as shown in FIG. 8, a retraction limiter in the form of a filament 269 could be disposed between the proximal adapter 42 and the handle 93 of the first release wire 24 such that proximal retraction of the first release wire 24 sufficient for deployment of the first distal belt 21 could be achieved, but not so much as to allow deployment of the second distal belt 22. In order to deploy the second distal belt 22, the filament 268 would have to be severed or otherwise released. This type of configuration can allow more control over deployment of the endovascular graft 11 and allow deployment in stages which are sequentially controlled to prevent inadvertent deployment of a portion of the graft 11 in an undesirable location within the patient's vessels.

Figure 9:
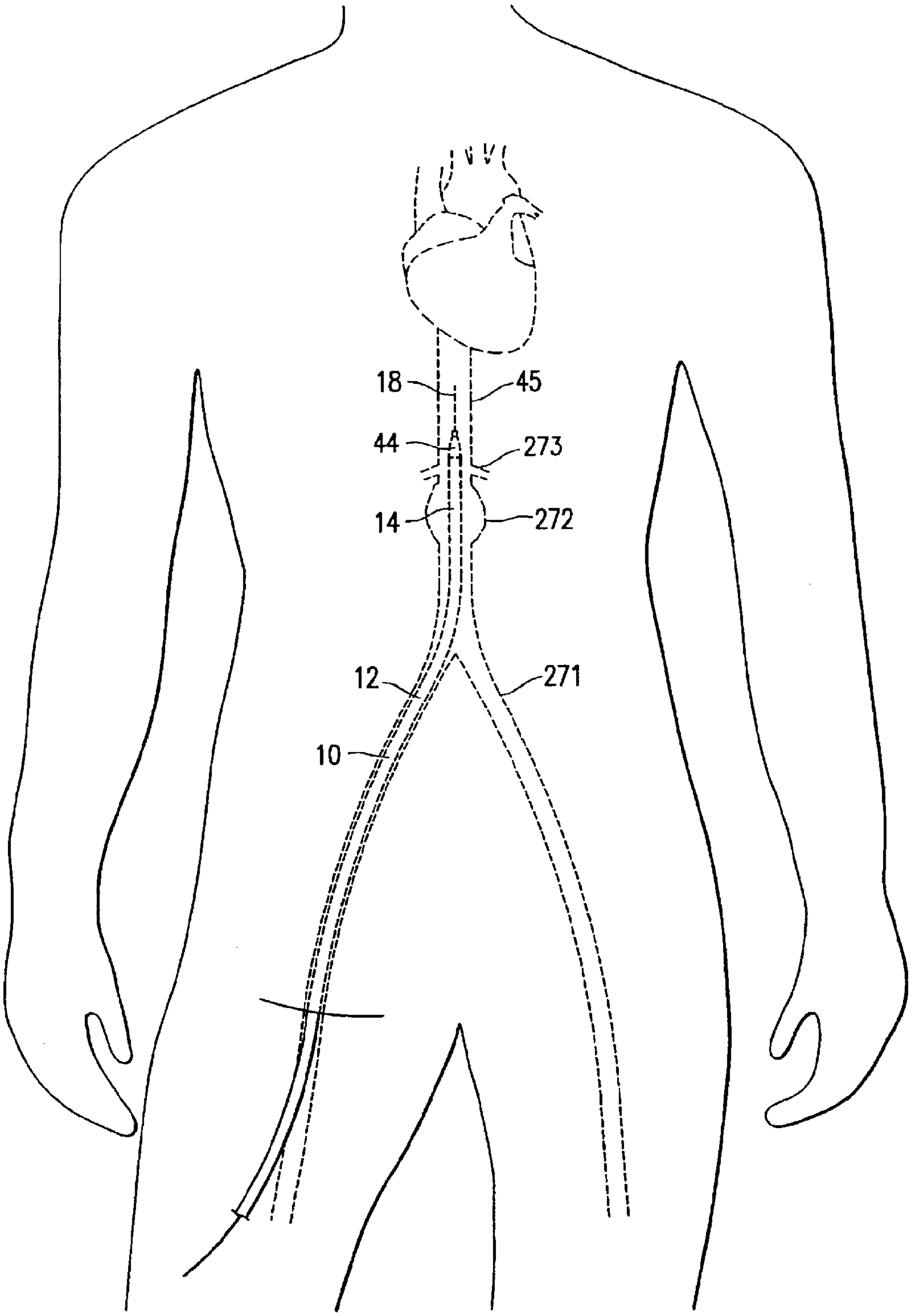
FIG. 9 is a diagrammatic view of a patient's body illustrating the patient's heart, aorta, iliac arteries, femoral arteries, and a delivery system having features of the invention disposed within the femoral artery and aorta.

In use, the delivery system 10 is advanced into a patient's arterial system 271 percutaneously as shown in FIG. 9 and positioned so that the endovascular graft 11 spans an aneurysm 272 in the patient's aorta 45 as illustrated in FIGS. 1 and 9–12. It is generally desirable to have the tubular body member 205 of the graft 11 positioned below the renal arteries 273 in order to prevent significant occlusion of the renal arteries. The procedure typically begins with the placement of guidewire 18 into the patient's target vessel 45 across the target location, e.g., the aneurysm 272. Common percutaneous techniques known in the art may be used for the initial placement of the guidewire 18. For example, as shown in FIG. 9, percutaneous access to the aorta may be had through the femoral or iliac artery, although other access sites may be used. The delivery system 10 may then be advanced over the guidewire 18 to a desired position within the patient's vessel 45. Alternatively, delivery system 10 and guidewire 18 could be advanced together into the patient's vasculature 271 with the guidewire 18 extending distally from the distal port 38 of the guidewire tube 17. In addition, it may be desirable in some cases to advance the delivery system 10 to a desired location within the patient without the use of a guidewire 18.

Figure 11:
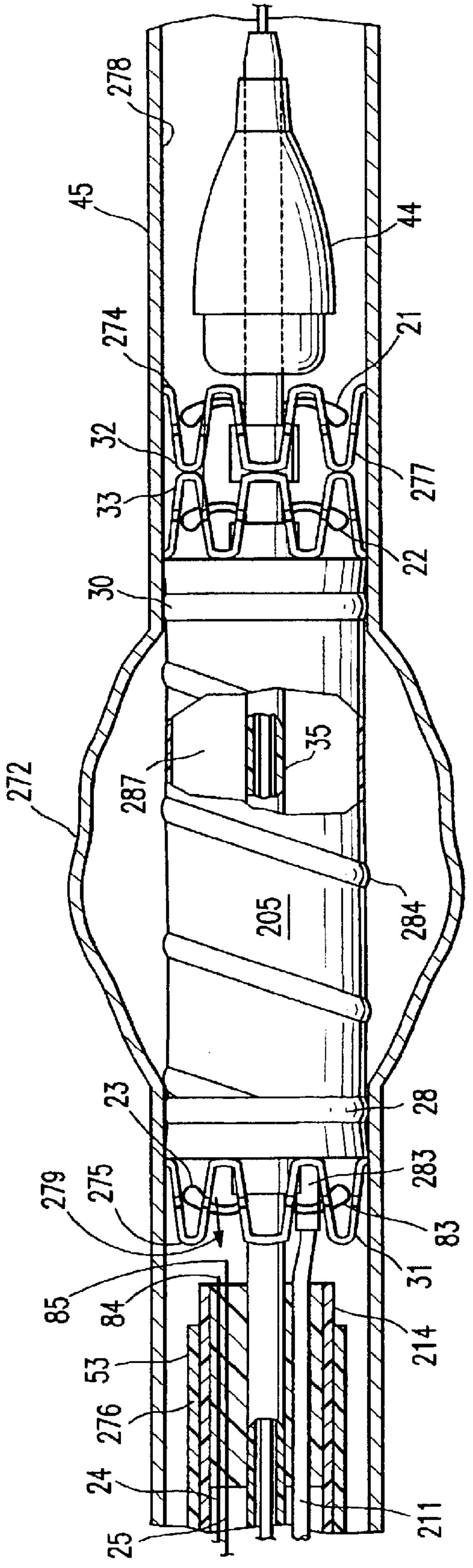
FIG. 11 is a diagrammatic view of a delivery system having features of the invention disposed within an artery of a patient with an expandable intracorporeal device being deployed within the artery.

Generally, the position of the delivery system 10 is determined using fluoroscopic imaging or the like. As such, it may be desirable to have one or more radiopaque markers (not shown) secured to the delivery system at various locations. For example, markers may be placed longitudinally coextensive with the respective distal and proximal extremities 274 and 275, as shown in FIG. 11. In this way, it can be readily determined whether the graft 11 is spanning the aneurysm 272 of the patient's artery. Imaging markers, such as radiopaque markers, may also be secured to desirable positions on the endovascular graft 11 itself. Other types of imaging and marking systems may be used such as computed tomography (CT), magnetic resonance imaging (MRI) and nuclear magnetic resonance (NMR) imaging systems and markers.

Once the distal section 14 of the delivery system 10 is properly positioned within the patient's artery 45, the operator moves the proximal end 261 of outer tubular member 53 in a proximal direction relative to inner tubular member 207. The relative axial movement is carried out by grasping the proximal end 215 of the inner tubular member 207 or proximal adapter 42, and grasping the proximal end 261 of the outer tubular member 53, and moving the respective proximal ends towards each other. This retracts the distal section 276 of the outer tubular member 53 from the constrained endovascular graft 11 and frees the graft for outward radial expansion and deployment. However, in this deployment scheme, note that the operator is free to reinsert graft 11 back into the outer tubular member 53 if necessary, as the release bands have not yet released the graft.

Once the distal section 276 of the outer tubular member 53 has been retracted, handle 93 of the first release wire 24 may then be unscrewed or otherwise freed from the proximal adapter 42 and retracted in a proximal direction indicated by arrow 279 in FIG. 10 until the distal end 84 of the first release wire 24 passes from within the end loops 81 of the first distal belt 21. When this occurs, the looped ends 81 of the first distal belt 21 are released and the first distal belt 21 ceases to radially constrain the first distal self-expanding member 32 which thereafter self-expands in a radial direction into an inner surface 278 of the patient's aorta 45 as shown in FIG. 10.

If the operator of the delivery system 10 is not satisfied with the position, particularly the axial position, of the endovascular graft 11 after deployment of the first distal self-expanding member 32, it may then be possible to re-position the endovascular graft 11 by manipulating the proximal end 15 of the elongate shaft 15. Movement of the elongate shaft 12 can move the endovascular graft 11, even though physical contact between the expanded member 32 and the vessel inner surface 278 generates some static frictional forces that resist such movement. It has been found that the endovascular graft 11 can be safely moved within a blood vessel 45 even in the state of partial deployment discussed above, if necessary.

Once the operator is satisfied with the position of the graft 11, the first release wire 24 may then be further proximally retracted so as to deploy the second distal belt 22 in a manner similar to the deployment of the first distal belt 21. The deployment of the second distal belt 22 occurs when the distal end 84 of the first release wire 24 passes from within end loops 82 of the second distal belt 22 which are held in a radially constraining configuration by the first release wire 24. Upon release of the second distal belt 22, the second distal self-expanding member 33 expands in a radial direction such that it may engage inner surface 278 of the patient's aorta 45. The amount of outward radial force exerted by the self-expanding members 32 and 33 on the inside surface 278 of the patient's aorta 45, which may vary between members 32 and 33, is dependent upon a number of parameters such as the thickness of the material which comprises the self-expanding members 32 and 33, the nominal diameter which the self-expanding members 32 and 33 would assume in a free unconstrained state with no inward radial force applied, material properties of the members and other factors as well.

Once the distal members 32 and 33 are deployed, the handle 94 for the second release wire 25 can be disengaged and axially retracted in a proximal direction from the proximal adapter 42 until the distal end 85 of the second release wire 25 passes from within the end loops 83 of the proximal belt 23. Once the proximal belt 23 is released, the proximal self-expanding member 31 is deployed and expands in an outward radial direction, such that it may engage or be in apposition with the inner surface 278 of the patient's aorta 45 as shown in FIG. 11. Thereafter, the endovascular graft 11 may be inflated with an inflation material (not shown) introduced into the proximal injection port 282 in the proximal adapter 42, through the inflation tube 211, and into the inflation port 283 of the endovascular graft 11. Inflation material may be injected or introduced into the inflation port 283 until the proximal and distal inflatable cuffs 28 and 30 and inflatable channels 284 of the graft 11 have been filled to a sufficient level to meet sealing and other structural requirements necessary for the tubular body to meet clinical performance criteria.

Before or during the deployment process, and preferably prior to or simultaneous with the step of inflating the endovascular graft 11, it may be beneficial to optionally treat vessel 45 in which the graft 11 is deployed so to obtain a better seal between the graft 11 and the vessel inner surface 278, thus improving the clinical result and helping to ensure a long term cure.

One approach to this treatment is to administer a vasodilator, or spasmolytic, to the patient prior to deploying graft 11. This has the effect of reducing the tone of the smooth muscle tissue in the patient's arteries; specifically, the smooth muscle tissue in the wall of vessel 45 into which graft 11 is to be deployed. Such tone reduction in turn induces the dilation of vessel 45, reducing the patient's blood pressure. Any number of appropriate vasoactive antagonists, including the direct acting organic nitrates (e.g., nitroglycerin, isosorbide dinitrate, nitroprusside), calcium channel blocking agents (e.g., nifedipine), angiotensin-converting enzyme inhibitors (e.g., captopril), alpha-adrenergic blockers (e.g., phenoxybenzamine, phentolamine, prasozin), beta-adrenergic blockers (e.g., esmolol) and other drugs may be used as appropriate. Particularly useful are those vasodilators that can be administered intravenously and that do not have unacceptable contraindications such as aoritic aneurysm dissection, tachycardia, arrhythmia, etc.

The degree of vasodilatation and hypotensive effect will depend in part on the particular vessel in which graft 11 is to be placed and the amount of smooth muscle cell content. Generally, the smaller the vessel, the larger percentage of smooth muscle cell present and thus the larger effect the vasodilator will have in dilating the vessel. Other factors that will effect the degree of vasodilatation is the health of the patient; in particular, the condition of the vessel 11 into which graft 11 is to be placed.

In practice, once the vasodilator has been administered to the patient, graft 11 may be deployed and filled with inflation material so that graft 11 reaches a larger diameter than would otherwise be possible if such a vasodilator was not used. This allows the inflation material to expand the diameter of graft 11, for a given inflation pressure, beyond that which would be achievable if the vessel 45 were in a non-dilated state (and nominal diameter). Alternatively, a larger diameter graft 11 may be chosen for deployment. We anticipate that an increased vessel diameter of between two and twenty percent during vasodilatation may be optimal for-achieving an improved seal.

The vessel 45 in which graft 11 is to be placed may optionally be monitored pre- and/or post-dilation but before deployment of graft 11 (via computed tomography, magnetic resonance, intravenous ultrasound, angiography, blood pressure, etc.) so to measure the degree of vasodilatation or simply to confirm that the vasodilator has acted on the vessel 45 prior to deploying graft 11.

Once the vasodilator wears off, preferably after between about five and thirty minutes from the time the drug is administered, the vessel 45 surrounding graft 11 returns to its normal diameter. The resultant graft-vessel configuration now contains an enhanced seal between graft 11 and vessel inner surface 278 and provides for reduced luminal intrusion by graft 11, presenting an improved barrier against leakage and perigraft blood flow compared to that obtainable without the sue of vasodilators or the like.

Such vasodilating techniques may be used with all of the embodiments of the present invention, including the tubular graft 11 as well as a bifurcated graft version of the expandable intracorporeal device of the present invention as is discussed in detail below.

Figure 12:
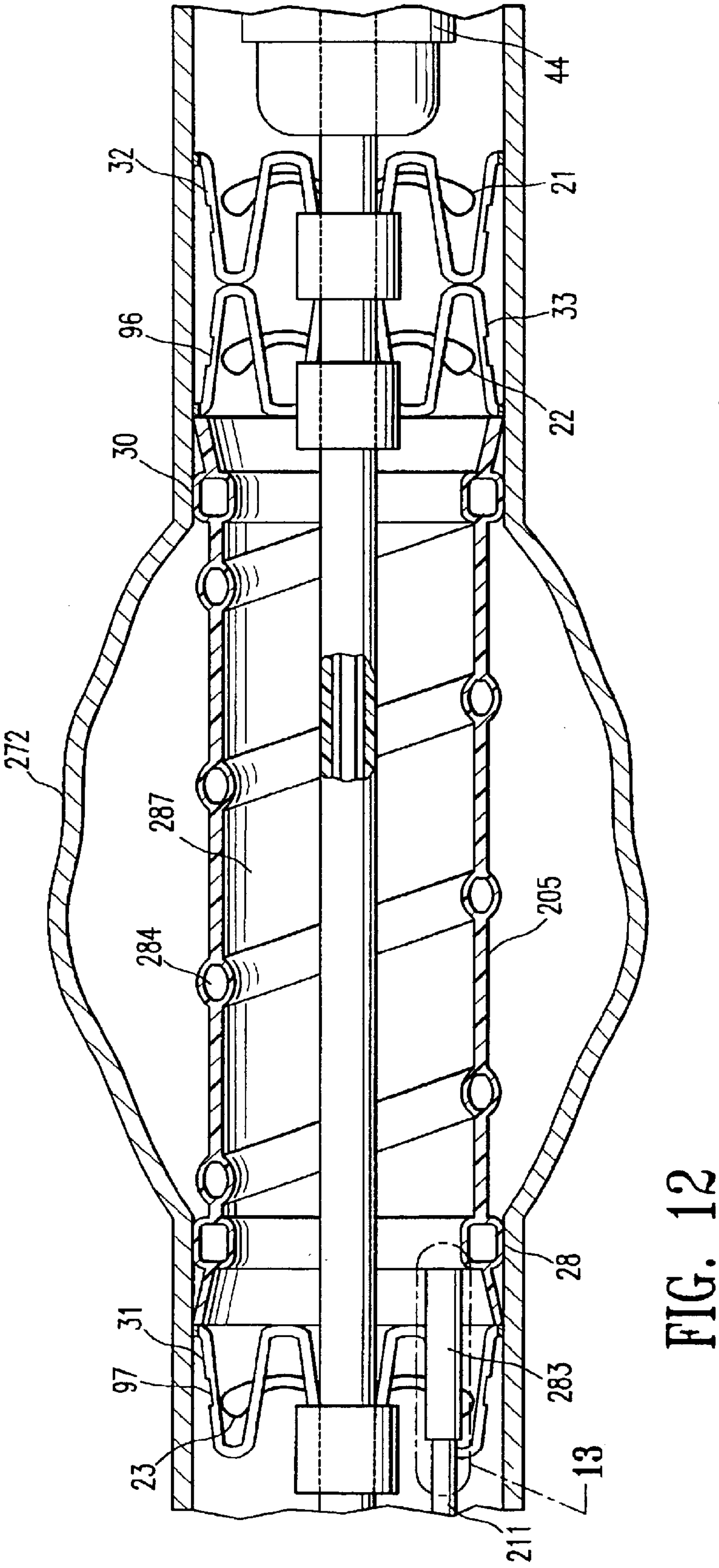
FIG. 12 is an enlarged diagrammatic view of a delivery system having features of the invention disposed within an artery of a patient with an expandable intracorporeal device being deployed within the artery.
Figure 13:
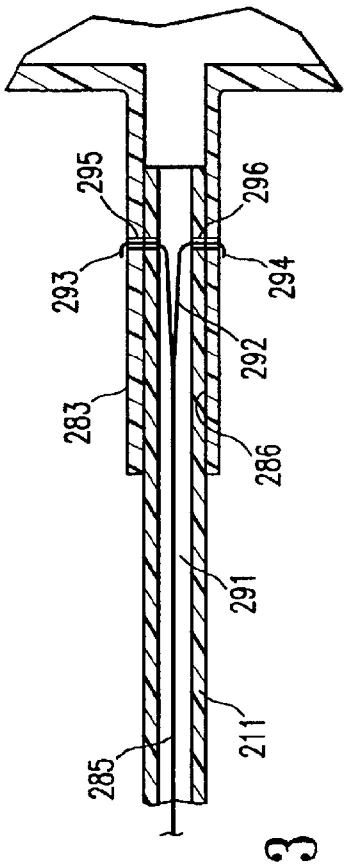
FIG. 13 is an elevational view in partial section of a connection between an inflation tube and an inflation port of an endovascular graft.

Once graft 11 is fully deployed, a restraining or retention device, such as retention wire 285 that binds the distal end 286 of the inflation tube 211 to the inflation port 283, as shown in FIGS. 12 and 13, is activated. The retention wire 285 is activated by pulling the proximal end of the wire in a proximal direction so as to disengage the distal ends 293 and 294 from the holes 295 and 296. This eliminates the shear pin function of the distal ends 293 and 294 and allows the distal end 286 of the inflation tube 211 to be disengaged from the inflation port 283. The release wires 24 and 25 may then be fully retracted from the elongate shaft 12 in a proximal direction and the delivery system 10 retracted in a proximal direction from the deployed endovascular graft 11. The unconstrained distal belts 21–23 slip through the openings in the expanded members 31, 32 and 33 as the delivery system 10 is retracted and are withdrawn through the inner passageway 287 of the deployed graft 11. The distal nosepiece 44 is also withdrawn through the inner passageway 287 of the deployed graft 11 as the delivery system 10 is withdrawn as shown in FIGS. 10–12.

FIG. 13 illustrates the junction between the distal end 286 of inflation tube 211 and inflation port 283. Typically, retention wire 285 extends from the inflation port 283 proximally to the proximal end 15 of delivery system 10. In this way, an operator can disengage the distal end 286 of the inflation tube 211 from the inflation port 283 by pulling on the proximal end of retention wire 285 from a proximal end 15 of delivery system 10. The retention wire 285 can be a small diameter wire made from a material such as a polymer, stainless steel, nickel titanium, or other alloy or metal; in a particular embodiment of the invention, retention wire 285 may be a spring formed of a variety of suitable spring materials. Alternatively retention wire 285 may have a braided or stranded configuration.

FIG. 13 shows a single retention filament or wire 285 disposed within the lumen 291 of the inflation tube 211. The distal end 292 of retention wire 285 may have one or more loops 293 and 294, respectively, disposed within one or more side holes disposed in the inflation port 283 of the distal end 286 of the inflation tube 211. A number of side hole configurations may be utilized. The embodiment of FIG. 13 has two sets of opposed side hole locations 295 and 296. The distal end loops 293 and 294 of the retention wire 285 act to interlock the side holes 295 and 296 by creating a removable shear pin element which prevents relative axial movement between the distal end 286 of the inflation tube 211 and the inflation port 283. Alternate embodiments may include multiple retention filaments or wires disposed within the lumen 291 of the inflation tube 211. An external sleeve (not shown) may be added over this assembly to further secure the interface and prevent leakage of inflation material through side holes 295 and 296. This sleeve is attached to inflation tube 211 and is received with it.

Figure 14:
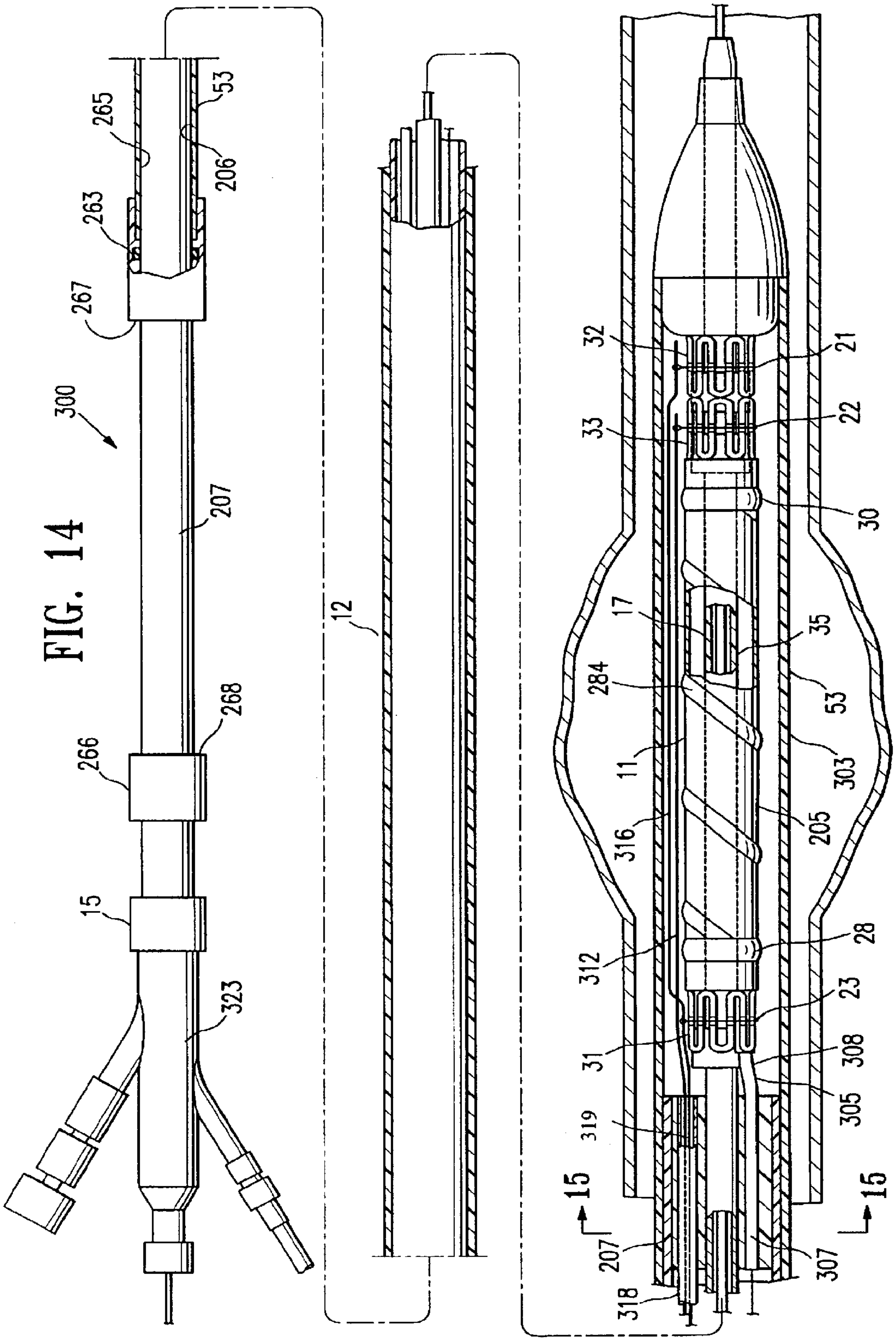
FIG. 14 is an elevational view in partial longitudinal section illustrating an embodiment of a delivery system for an expandable intracorporeal device having features of the invention.
Figure 15:
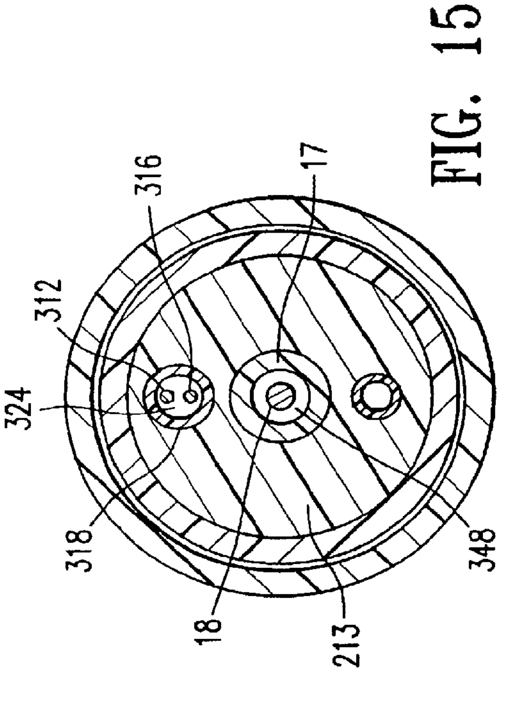
FIG. 15 is a transverse cross sectional view of the delivery system of FIG. 14 taken along lines 15—15 in FIG. 14.
Figure 16:
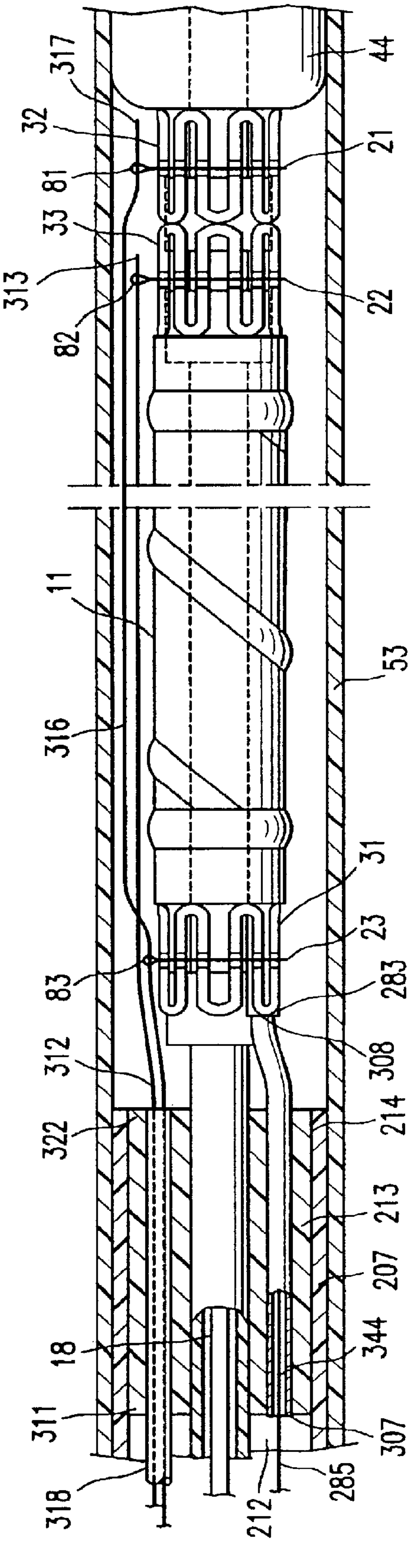
FIG. 16 is an enlarged elevational view in partial section of the delivery system shown in FIG. 14.

FIGS. 14–17 illustrate an alternative embodiment of the delivery system shown in FIG. 1. In FIGS. 14–17, like elements with respect to the embodiment of FIG. 1 will be shown with like reference numerals where appropriate. The delivery system 300 has an outer tubular member 53 and inner tubular member 207 at a distal section 303 of the delivery system 300. An endovascular graft 11 is disposed within the outer tubular member in the distal section 303. An inflation tube 305, similar to that of the embodiment shown in FIG. 1 is coupled to an inflation port 283 of the endovascular graft 11. However, the inflation tube 305, having a proximal end 307 and a distal end 308, does not extend the majority of the length of the delivery system 300. Instead, the proximal end 307 of the inflation tube 305 terminates at a proximal end 311 of the potted section 213 as shown in FIGS. 14–16.

Figure 17:
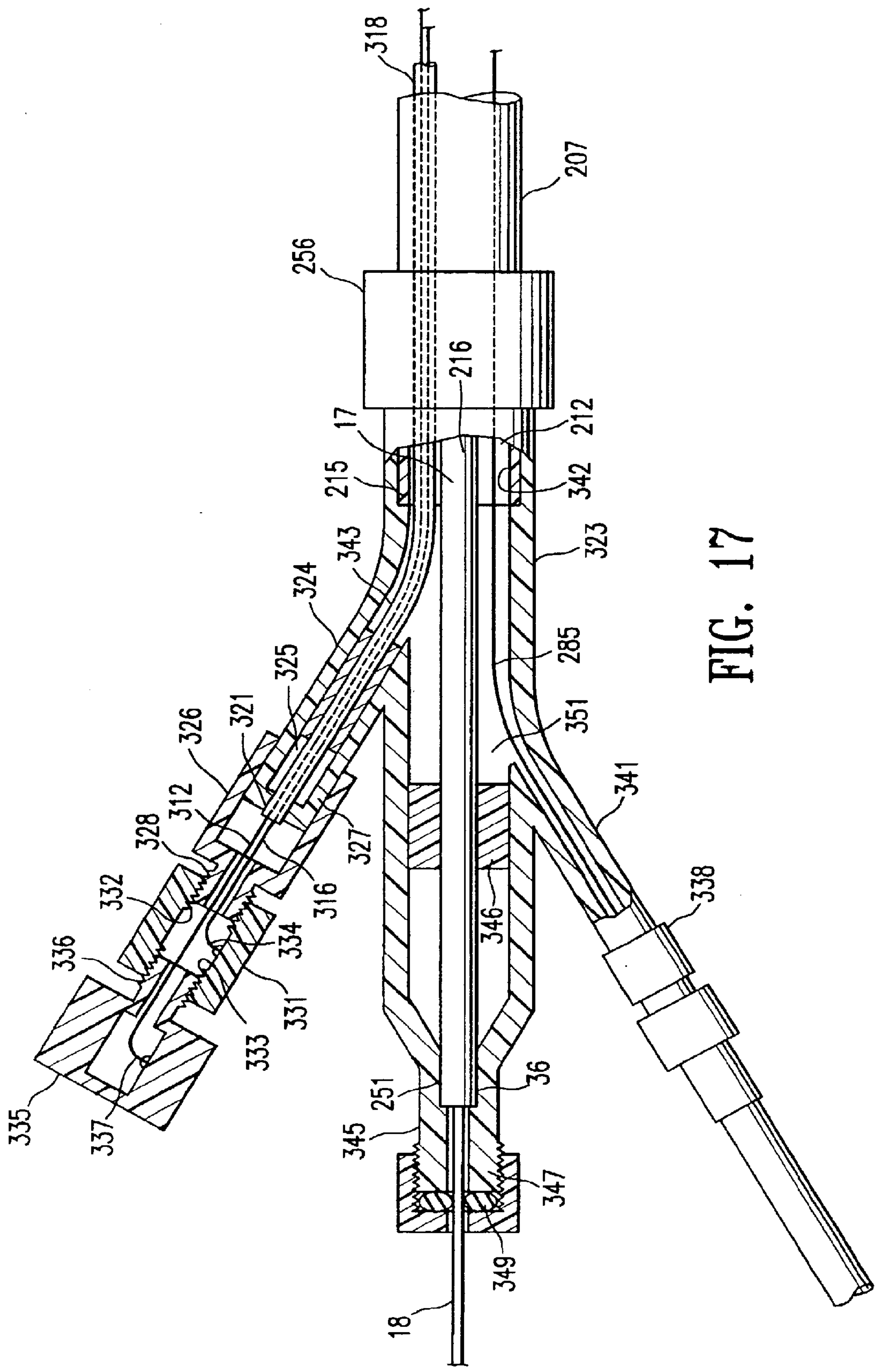
FIG. 17 is an elevational view in partial section of the proximal adapter of the delivery system shown in FIG. 14.

Referring to FIGS. 14 and 16, first release wire 312 having distal end 313 engages end loops 82 of second distal belt 22. The second distal belt 22 is disposed about and constrains the second distal self-expanding member 33. A second release wire 316 having a distal end 317 engages the end loops 81 of the first distal belt 21 and the end loops 83 of the proximal belt 23. The first distal belt 21 is disposed about and constrains the first distal self-expanding member 32. The proximal belt 23 is disposed about and constrains the proximal self-expanding member 31 A release wire tube 318, having a proximal end 321, as shown in FIG. 17, and a distal end 322, shown in FIG. 16, extends from the potted section 213 of the distal section 303 of the delivery system 300 to the proximal adapter 323 shown in FIG. 17. The release wire tube 318 has a lumen 319, as shown in FIG. 15, that contains the first release wire 312 and the second release wire 316.

The proximal adapter 323 has a first side arm 324 with an inner lumen 325 that secures the proximal end 321 of the release wire tube 318. A threaded end cap 326 is secured to a proximal end 327 of the first side arm 324 and has a threaded portion 328. A second release wire handle 331, having a distal threaded portion 332 and a proximal threaded portion 333, is threaded onto the threaded end cap 326. A proximal end 334 of the second release wire 316 is secured to the second release wire handle 331. A first release wire handle 335 has a threaded portion 336 which is releasably threaded onto the proximal threaded portion 333 of the second release wire handle 331. A proximal end 337 of the first release wire 312 is secured to the first release wire handle 335.

Once the outer tubular member 53 has been proximally retracted, belts 21–23 can be released. This configuration allows the operator of the delivery system 300 to first disengage and proximally retract the first release wire handle 335 so as to first release the second distal self-expanding member 33 without releasing or otherwise disturbing the constrained state of the first distal self-expanding member 32 or the proximal self-expanding member 31. Once the second distal self-expanding member 33 has been deployed or released, the endovascular graft 11 may be axially moved or repositioned to allow the operator to adjust the position of the graft 11 for final deployment.

This is advantageous, particularly in the treatment of abdominal aortic aneurysms, because it allows the physician to accurately place graft 11 into position. In many cases, it is desirable for the physician to place the graft 11 such that the distal end of the tubular body portion 205 of the graft is just below the renal arteries 273, shown in FIG. 9, to prevent occlusion of the renal arteries by the tubular body portion 205. If a self-expanding member, such as self-expanding member 32 is radiopaque and the delivery procedure is performed using fluoroscopic imaging, adjustment of the position of the graft after release of self-expanding member is readily achievable. Because self-expanding member 32 is immediately adjacent the distal end of the tubular body portion 205 of the graft 11, the ability to visualize and reposition the self-expanding member 32 is particularly useful in order to position the distal end of the tubular body portion 205 just below the renal arteries without occluding the renal arteries, if such positioning is indicated for the patient being treated.

Thereafter, the second release wire handle 331 may be unscrewed or otherwise released from the threaded cap 326 and proximally retracted so as to first release the first distal belt end loops 81 and then the proximal belt end loops 83. Of course, the position of the graft 11 may still be adjustable even with both distal self-expanding members 32 and 33 deployed, depending on the particular configuration of the graft 11 and the self-expanding members 32 and 33. The release of the belts 21, 22 and 23 is the same or similar to that of the belts of the embodiment of FIG. 1 and occurs when the distal end of the release wires 312 and 316 which lock the end loops 81–83 together is proximally retracted past the end loops 81–83 of the belts 21–23 which are constrained.

Once the self-expanding members 31–33 of the endovascular graft 11 have been deployed or released, and the graft 11 is in a desired location, the graft 11 can then be inflated by injection of an inflation material (not shown) into the injection port 338 on a second side arm 341 of the proximal adapter 323. The inflation material is introduced or injected directly into an inner lumen 212 of the inner tubular member 207, as shown in FIG. 17, and travels distally between an inside surface 342 of the inner tubular member 207, outside surface 343 of the release wire tube 318 and outside surface 216 of the guidewire tube 17. This allows the inflation material, which can be highly viscous, to flow through the cross sectional area between the inside surface 342 of the inner tubular member 207 and the outside surfaces 216 and 343 of the release wire tube 318 and guidewire tube 17. This cross sectional area is large relative to the cross sectional area of the inner lumen of the inflation tube 211 of the embodiment of FIG. 1. This results in more rapid flow of inflation material to the inflatable cuffs 28 and 30 and channels 284 of the endovascular graft 11 and decreases inflation time.

Once the inflation material, which is travelling distally in the delivery system 300 during inflation, reaches the potted portion 213 of the distal section 303 of the delivery system, it then enters and flows through a lumen 344, as shown in FIG. 16, at the proximal end 307 of the inflation tube 305 and into the inflation port 283 of the graft 11. Upon inflation of the graft 11 with an inflation material, a release device, such as retention wire 285 can be retracted or otherwise activated so as to de-couple the inflation tube 305 from the inflation port 283 of the endovascular graft 11.

A proximal end 36 of the guidewire tube 17 is secured within a central arm 345 of the proximal adapter 323 which has a potted section 346. A seal 349 is disposed on a proximal end 347 of the central arm 345 for sealing around the guidewire 18 and preventing a backflow of blood around the guidewire. A hemostasis adapter (not shown) can be coupled to the proximal end 347 of the central arm 345 in order to introduce fluids through the guidewire tube lumen 348, as shown in FIG. 15, around an outside surface of the guidewire 18. The potted section 346 of the central arm 345 prevents any injected fluids from passing into the inflation material lumen 351 within the proximal adapter 323 or the inner tubular member 207.

Figure 18:
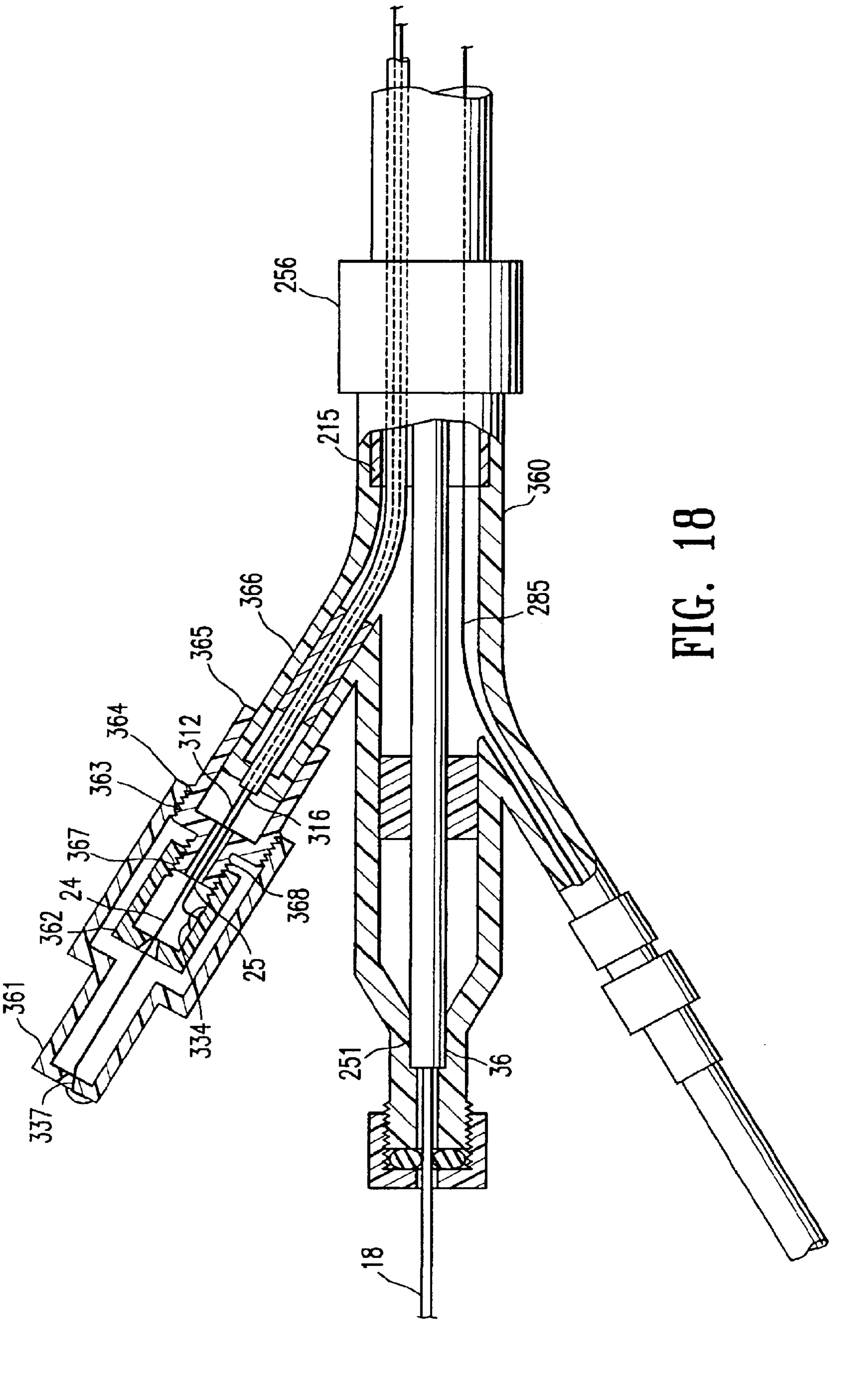
FIG. 18 is an elevational view in partial section of an alternative embodiment of the proximal adapter of the delivery system shown in FIG. 14 with a nested handle configuration.

FIG. 18 illustrates an alternative embodiment to the proximal adapters 42 and 323 used in the embodiments of the invention of FIG. 1 and FIG. 14. In this embodiment, the proximal adapter 360 has a first release wire handle 361 and a second release wire handle 362 which are in a nested configuration. The proximal end 334 of the second release wire 316 is secured to the second release wire handle 362. The proximal end 337 of the first release wire 312 is secured to the first release wire handle 361. This configuration prevents the operator from inadvertently deploying or activating the second release wire 316 prior to deployment or activation of the first release wire 312 which could result in an undesirable endovascular graft deployment sequence.

In use, the operator first unscrews or otherwise detaches a threaded portion 363 of the first release wire handle 361 from an outer threaded portion 364 of a first side arm end cap 365 of a first side arm 366. The first release wire handle 361 is then proximally retracted which releases the end loops 82 of the second distal belt 22 as discussed above with regard to the embodiment of the invention shown in FIG. 14.

Once the first release wire handle 361 is removed from the first side arm end cap 365, the second release wire handle 362 is exposed and accessible to the operator of the delivery system. A threaded portion 367 of the second release wire handle 362 can then be unscrewed or otherwise detached from an inner threaded portion 368 of the first side arm end cap 365. The second release wire handle 362 can then be retracted proximally so as to sequentially deploy the first distal belt 21 and self-expanding member 32 and proximal belt 23 and proximal self-expanding member 31, respectively. The other functions and features of the proximal adapter 360 can be the same or similar to those of the proximal adapters 42 and 323 shown in FIG. 1 and FIG. 17 and discussed above.

Optionally, this embodiment may comprise reverse or oppositely threaded portions, 363 and 367 respectively, of the first and second release wire handles 361 and 362. Thus, for instance, a counter-clockwise motion may be required to unthread threaded portion 363 of the first release wire handle 361 from the outer threaded portion 364, while a clockwise motion is in contrast required to unthread threaded portion 367 of the second release wire handle 367 from the inner threaded portion 368. This feature serves as a check on the overzealous operator who might otherwise prematurely unscrew or detach the threaded portion 367 of the second release wire handle 362 by unscrewing in the same direction as required to release the threaded portion 363 of the first release wire handle 361.

In another aspect of the invention, a delivery system 400 for delivery and deployment of a bifurcated intracorporeal device, specifically, an embodiment of the invention directed to delivery and deployment of a bifurcated endovascular graft or stent is contemplated. As with all the delivery systems disclosed herein, the delivery system 400 for a bifurcated device is configured for delivery and deployment a wide variety of intracorporeal devices. Although the focus of the specific embodiments are directed to systems for delivery of endovascular grafts or stent grafts, embodiments of the delivery systems disclosed herein can are also suitable for delivery of intravascular filters, stents, including coronary stents, other types of shunts for intracorporeal channels, aneurysm or vessel occluding devices and the like.

The structure, materials and dimensions of the delivery system 400 for bifurcated devices can be the same or similar to the structure, materials and dimensions of the delivery systems discussed above. In addition, the structure, materials and dimensions of bifurcated grafts contemplated herein can have structure, materials and dimensions similar to those of grafts having a primarily tubular shape discussed above.

FIGS. 19–22 illustrate an embodiment of an expandable intracorporeal device in the form of a bifurcated stent-graft 401. This embodiment includes a main body portion 402 at a distal end 403 of the graft 401 that has a generally tubular cross-sectional profile when the graft takes on an expanded or deployed configuration. An ipsilateral leg 404 and contralateral leg 405 (short leg), both having a substantially tubular configuration when expanded or deployed, branch from the main body portion 402 at bifurcation 406 and extend in a proximal direction from the bifurcation 406. The ipsilateral leg 404 terminates proximally with a proximal self-expanding member 407 and the contralateral leg 405 terminates proximally with a proximal self-expanding member 408.

The main body portion 402 of the graft may have a transverse dimension when in an expanded or deployed state ranging from about 10 mm to about 40 mm, specifically from about 15 mm to about 30 mm. The legs 404 and 405 of the graft 401 may have a transverse dimension when in an expanded or deployed state ranging from about 5 mm to about 16 mm, specifically from about 8 mm to about 14 mm. The main body portion 402 of the graft 401 may have a length ranging from about 2 cm to about 12 cm, specifically from about 4 cm to about 8 cm.

A second distal self-expanding member 411 is disposed at a distal end 412 of the main body portion 402 of the graft 401 as with the graft embodiments previously discussed. Also, as with other endovascular graft embodiments discussed herein, the graft 401 may have inflatable channels and inflatable cuffs that serve, among other functions, to provide support for the graft 401 and the inflatable channels and cuffs can have configurations which are the same or similar to those inflatable channels and cuffs of other graft embodiments discussed herein, as well as other configurations. A distal inflatable cuff 413 is disposed at the distal end 412 of the main body portion 402. Proximal inflatable cuffs 414 and 415 are disposed on a proximal end 416 of the ipsilateral leg 404 and a proximal end 417 of the contralateral leg 405 respectively. Inflatable channels 418 are fluid tight conduits which connect the inflatable cuffs 413, 414 and 415. The inflatable channels 418 and inflatable cuffs 413 and 414 are inflatable through an inflation port 421 that may be disposed at or near the proximal end 416 of the ipsilateral leg 404. The inflation port 421 may also be disposed at or near the proximal end 417 of the contralateral leg 405, or it may be disposed on other portions of the device as necessary. Generally, the structure and the materials used in the graft 401 (both the graft portion and the self-expanding members) can be similar to the structure and materials of the other graft embodiments discussed above. In one particular embodiment, the main body portion and legs of the graft are made of expanded polytetrafluoroethylene (ePTFE) and the self-expanding members are made of nickel titanium, stainless steel or the like.

Figures 19, 20, 21, 22:
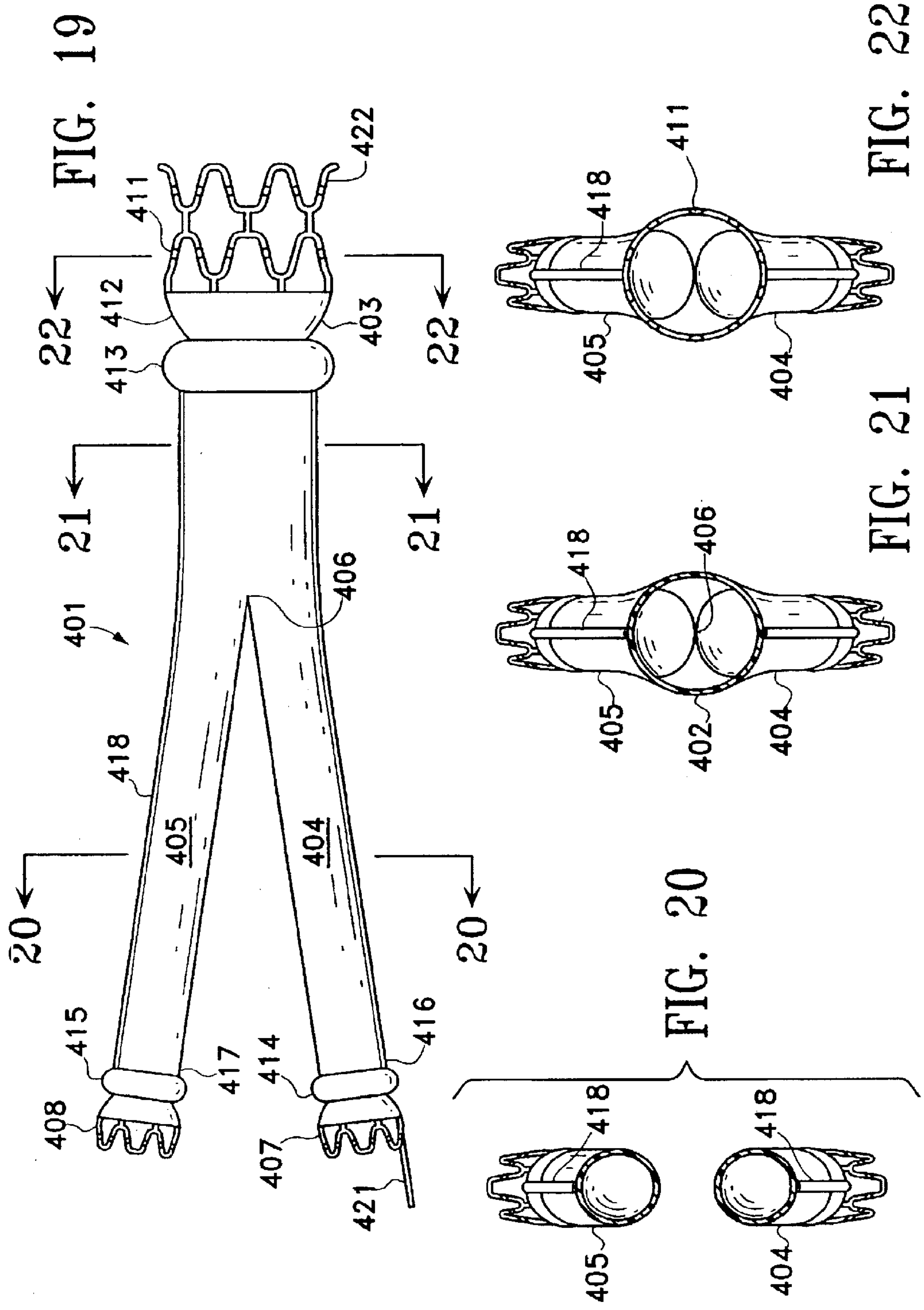
FIG. 19 is an elevational view of a bifurcated stent graft suitable for delivery and deployment by embodiments of the invention.
FIG. 20 is a transverse cross sectional view of the stent graft of FIG. 19 taken along lines 20—20 in FIG. 19.
FIG. 21 is a transverse cross sectional view of the stent graft of FIG. 19 taken along lines 21—21 of FIG. 19.
FIG. 22 is a transverse cross sectional view of the stent graft of FIG. 19 taken along lines 22—22 of FIG. 19.

A first distal self-expanding member 422 is secured to the second distal self-expanding member 411 as shown in FIG. 19. This configuration is similar to that of endovascular graft 11 illustrated in FIGS. 1–6B, 10–12 and 14–16 above. Graft 11 has first and second distal self-expanding members 32 and 33 which may be deployed in any desired sequence. In a particular embodiment having first and second distal self-expanding members, it may be desirable to first deploy the second distal self-expanding member 33 prior to deploying the first distal self-expanding member 32. As discussed above, deploying the second distal self-expanding member 33 first may allow the operator to accurately adjust the axial position of the graft in the body lumen or vessel to within one to several millimeters before deploying the first distal self-expanding member 32. Using this technique, deployment of the second distal self-expanding member 33 alone provides sufficient resistance to axial displacement of the graft 11 for the graft position to be maintained in normal blood flow, but still allows deliberate axial displacement by the operator to achieve a desired axial position. This may be particularly important if tissue-penetrating members are included on the distal-most or first distal self-expanding member 32. If such tissue penetrating members are used on the first distal self-expanding member 32, axial movement may be difficult or even impossible once this member 32 is deployed without risking damage to the body lumen or vessel. As such, accurate axial placement of the graft 11 prior to deployment of the first distal self-expanding member 32 can be critical.

In addition, although not shown in the figures, this graft embodiment 401 may include two or more proximal self-expanding members disposed on one or both of the ipsilateral leg 404 and/or contralateral leg 405. These self-expanding members may have a configuration similar to that of the first and second distal self-expanding members 411 and 422

Figure 23:
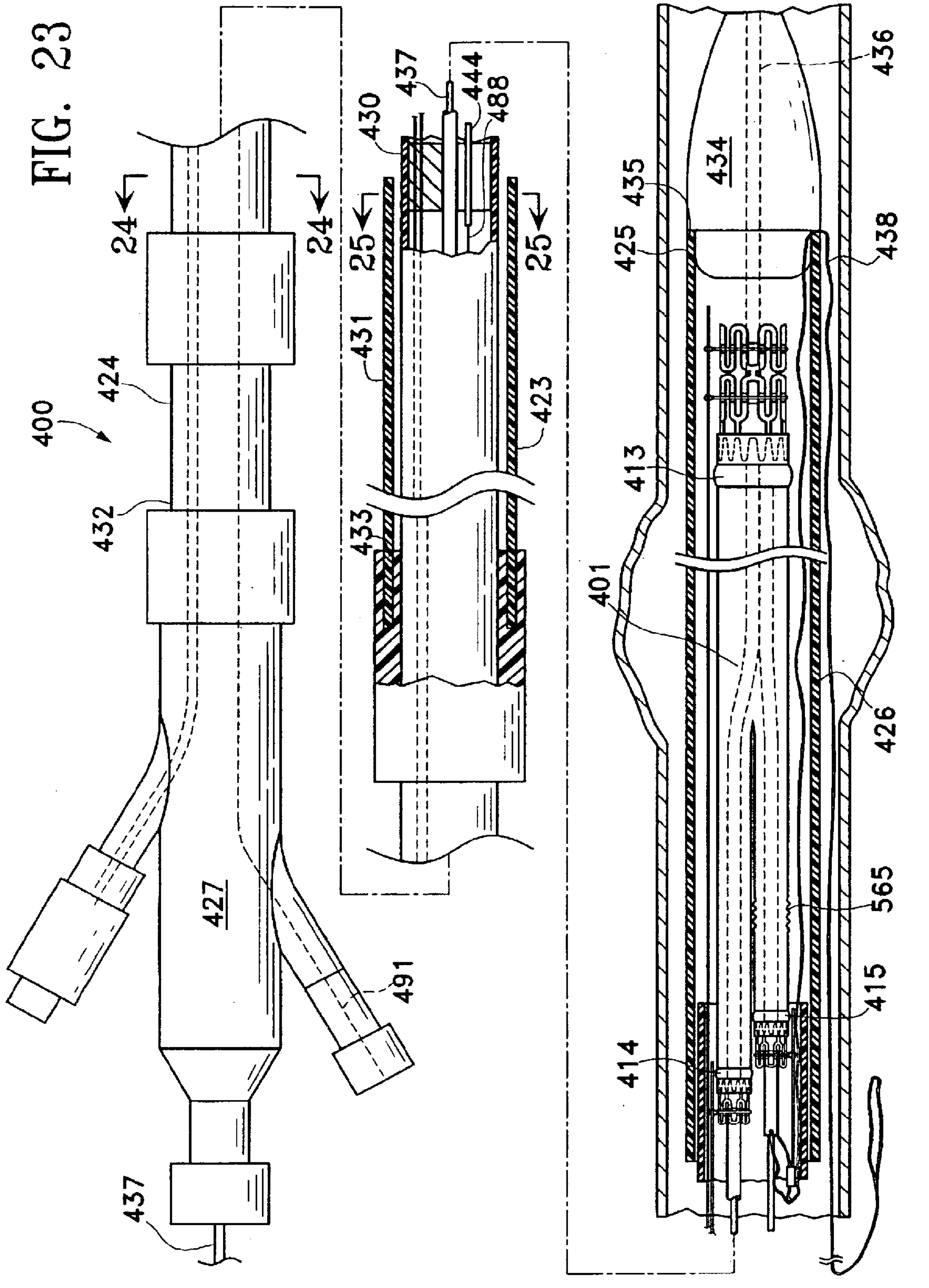
FIG. 23 is an elevational view in partial section of an embodiment of a delivery system having features of the invention.

FIGS. 23–32 illustrate an embodiment of a delivery system 400 having features of the invention. FIG. 23 shows delivery system 400 in partial section having an elongate shaft 423 with a proximal end 424, a distal end 425 and a distal section 426. A proximal adapter 427 is disposed at the proximal end 424 of the elongate shaft 423 and houses the controls that enable the operator to manipulate elements at the distal section 426 of delivery system 400 to release and deploy the graft 401, including inflating the graft channels 418 and cuffs 413, 414 and 415. The elongate shaft 423 has an inner tubular member 430 and an outer tubular member 431 disposed about the inner tubular member 430. The outer tubular member 431 is generally configured to slide in an axial direction over the inner tubular member 430. A proximal end 432 of the inner tubular member 430 is secured to or disposed on the proximal adapter 427. The inner and outer tubular members 430 and 431 may be made of polymeric materials, e.g., polyimides, polyester elastomers (Hytrel®), or polyether block amides (Pebax®), and other thermoplastics and polymers. The outside diameter of the outer tubular member 431 may range from about 0.1 inch to about 0.4 inch; specifically from about 0.15 inch to about 0.20 inch. The wall thickness of the outer tubular member 431 may range from about 0.002 inch to about 0.015 inch, specifically from about 0.004 inch to about 0.008 inch. The proximal adapter 427 is generally fabricated from a polymeric material such as polyethylene, acetal resins (Delrin®), etc., but can also be made from any other suitable material.

Bifurcated stent graft 401 is shown in FIGS. 23–28 disposed within the distal section 426 of the elongate shaft 423 in a constrained configuration. The outer tubular member 431 is disposed about the graft 401 in the constrained state but can be retracted proximally so as to expose the constrained graft 401 by proximally retracting a proximal end 433 of the outer tubular member 431. As illustrated more fully in FIG. 37, a distal nosepiece 434 may be disposed on a distal end 435 of the outer tubular member 431 and forms a smooth tapered transition from a guidewire tube 436 to the outer tubular member 431. This transition helps to facilitate the tracking of the outer tubular member 431 over a guidewire 437. In order to form this smooth transition, the nosepiece 434 may have a length to major diameter ratio ranging from about 3:1 to about 10:1 (the "major diameter" being defined as the largest diameter of the nosepiece). The outer tubular member 431 is not typically permanently secured to the nosepiece 434 and may be retractable from the nosepiece 434 during the deployment sequence. A secondary release cable 438 extends from an opening in the distal section of the elongate shaft.

Figure 24:
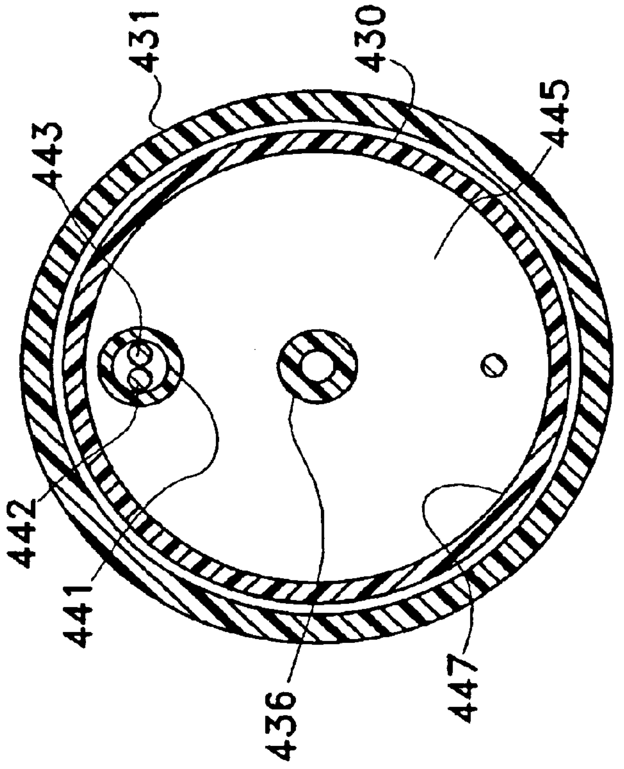
FIG. 24 is a transverse cross sectional view of the delivery system of FIG. 23 taken along lines 24—24 of FIG. 23.

FIG. 24 shows the inner tubular member 430 disposed within the outer tubular member 431 and the guidewire tube 436 disposed within the inner tubular member 430. The guidewire tube 436 may be made from polymeric materials such as polyimide, polyethylene, polyetheretherketones (PEEK™), or other suitable polymers, and may have an outside diameter ranging from about 0.02 inch to about 0.08 inch, specifically about 0.035 inch to about 0.055 inch. The guidewire tube 436 wall thickness may range from about 0.002 inch to about 0.025 inch, specifically from about 0.004 inch to about 0.010 inch.

A release member tube in the form of a release wire tube 441 is disposed about a distal primary release member in the form of a distal primary release wire 442. The release wire tube 441 is also disposed about a proximal primary release member in the form of a proximal primary release wire 443. Both the release member tube 441 and an inflation tube 444 are disposed within an inner lumen 445 of the inner tubular member 430. The outside diameter of the release wire tube 441 may range from about 0.01 inch to about 0.05 inch, specifically about 0.015 inch to about 0.025 inch. The wall thickness of the release wire tube 441 may range from about 0.001 inch to about 0.006 inch, specifically from about 0.002 inch to about 0.004 inch.

The outside diameter of the inflation tube 444 may range from about 0.02 inch to about 0.10 inch; specifically from about 0.04 inch to about 0.08 inch. The inflation tube 444 wall thickness may range from about 0.002 inch to about 0.025 inch; specifically from about 0.003 inch to about 0.010 inch.

Figure 25:
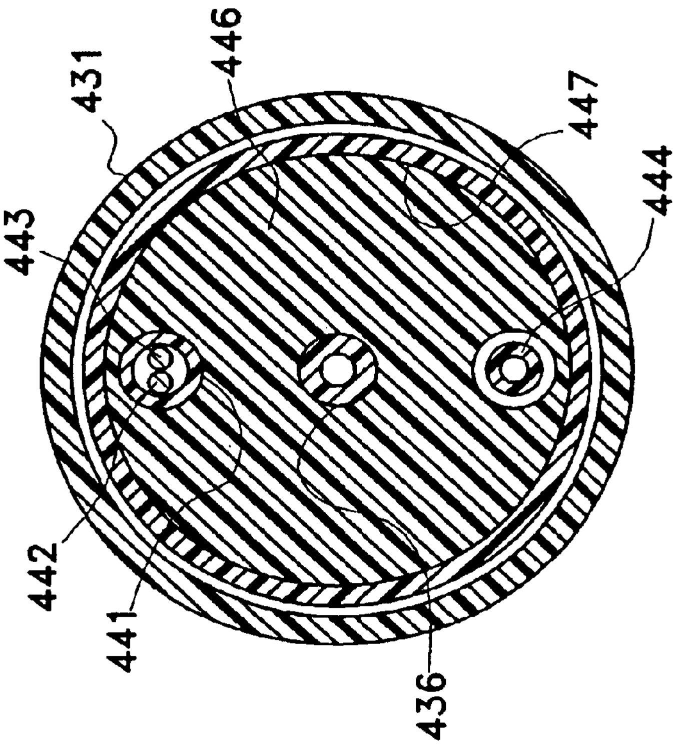
FIG. 25 is a transverse cross sectional view of the delivery system of FIG. 23 taken along lines 25—25 of FIG. 23.

In FIG. 25, a potted portion 446 is disposed between an inner surface 447 of a distal end 448 of the inner tubular member 430, the release wire tube 441, the guidewire tube 436 and the inflation tube 444. The potted portion 446 seals the inner lumen 445 of the inner tubular member 430 from bodily fluids that are exposed to the constrained graft 401 and potted portion 446 once the outer tubular member 431 is proximally retracted. The potted portion 446 may be made from adhesives, thermoforming plastics, epoxy, metals, or any other suitable potting material. Alternatively, a molded or machined plug may be bonded or affixed to the distal end of the inner tubular member, with lumens to accommodate the passage of tubes 441,436 and 444.

Figure 26:
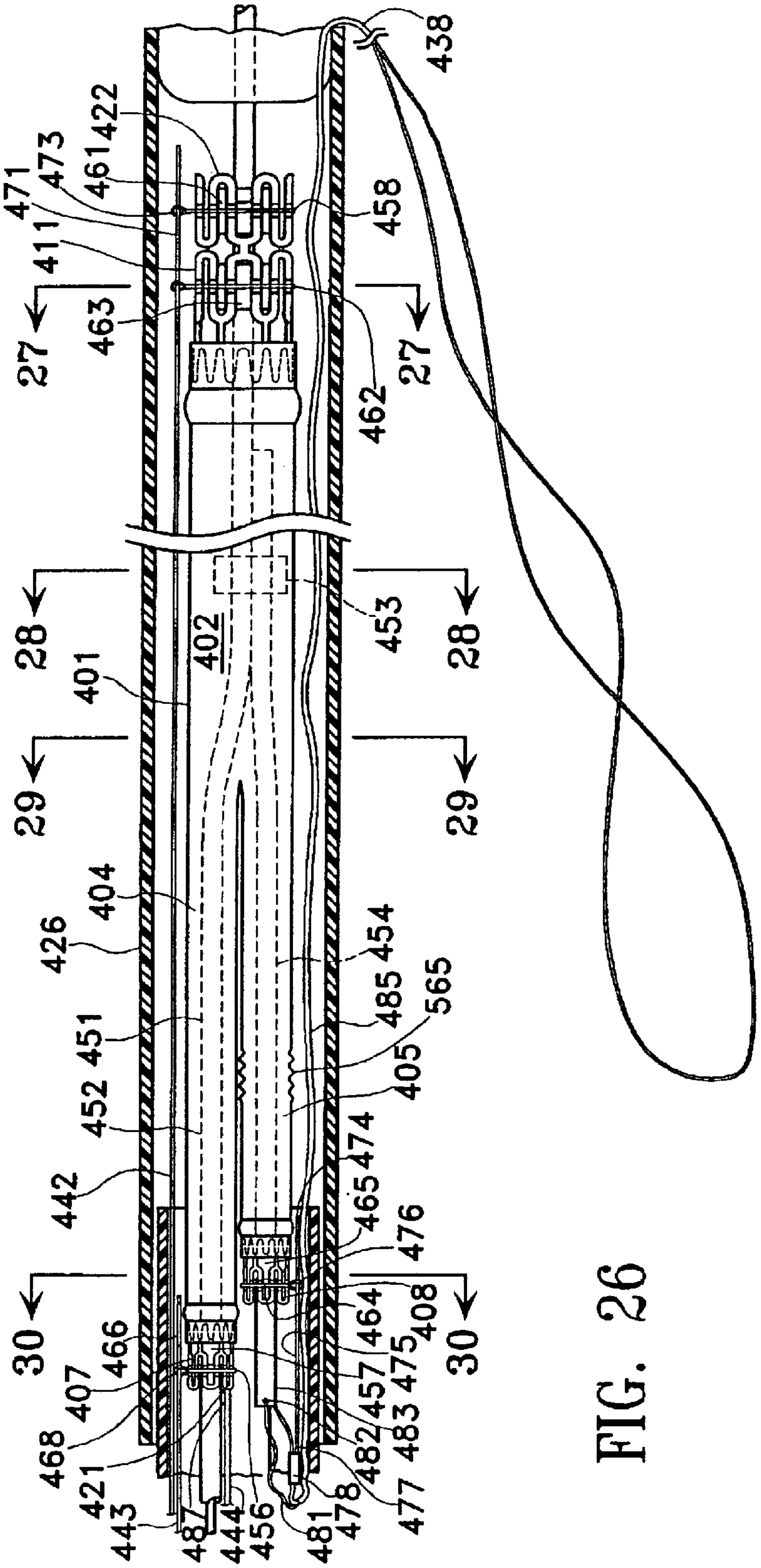
FIG. 26 is an elevational view in partial section showing an enlarged view of a distal portion of the delivery system of FIG. 23.

A more detailed view of the distal section 426 of the elongate shaft 423 is shown in partial section in FIGS. 26–30. A distal section 451 of the guidewire tube 436 serves as a primary belt support member 452 and is disposed within the main body portion 402 and ipsilateral leg 404 of the graft 401. Alternatively, the primary belt support member 452 may be disposed adjacent the graft main body portion 402 and ipsilateral leg 404. A secondary belt support member housing 453 is secured to the primary belt support member 452. An additional length of guidewire tube or other elongate member serving as a secondary belt support member 454 is slidably disposed within an appropriately configured lumen 455 of the housing 453. The secondary belt support member 454 is shown in FIG. 26 disposed within the graft main body portion 402 and contralateral leg 405; however, the secondary belt support member 454 may also be disposed adjacent the contralateral leg 405, regardless of whether the primary belt support member 452 is disposed adjacent or within the main body portion 402 and ipsilateral leg 404.

The secondary belt support member housing lumen 455 and secondary support member 454 cross sections may be keyed, singly or in combination, to allow relative sliding motion without relative rotation motion and therefore limit any twisting of the secondary support member 454 and the contralateral leg 405. The secondary belt support member 454 may be made from alloys such as nickel titanium, stainless steel, or polymeric materials such as polyimide and can have an outside transverse dimension ranging from about 0.01 inch to about 0.06 inch.

A proximal primary belt 456 is shown in FIG. 26 disposed about and radially constraining the proximal self-expanding member 407 of the ipsilateral leg 404. This proximal self-expanding member 407 in turn is disposed about a bushing 457 that is shown as cylindrical in form, but which may have other configurations as well. The bushing 457 is secured to the primary belt support member 452 adjacent the proximal self-expanding member 407 of the ipsilateral leg 404.

A first distal primary belt 458 is disposed about and radially constraining the first distal self-expanding member 422, which itself is disposed about a cylindrical bushing 461. A second distal primary belt 462 is disposed about and radially constraining the second distal self-expanding member 411 and the second distal self-expanding member 411 is disposed about a cylindrical bushing 463.

A secondary belt 464 is shown disposed about and radially constraining the proximal self-expanding member 408 of the contralateral leg 405. This proximal self-expanding member 408 is disposed about a bushing 465 which is cylindrical in shape.

As with the other embodiments of the present invention, the belts 456, 458, 462 and 464 are typically made from nickel titanium, an alloy that is capable of exhibiting a unique combination of high strain without elastic deformation, high strength and biocompatability. However, any other suitable materials may be used including other metallic alloys such as stainless steel, high strength fibers such as carbon, Kevlar®, polytetrafluoroethylene (PTFE), polyimide, or the like. The outer transverse dimension or diameter of the belts 456, 458, 462 and 464 can be from about 0.002 inch to about 0.012 inch; specifically about 0.004 inch to about 0.007 inch.

A distal portion 466 of the proximal primary release wire 443 is disposed within end loops 468 of the proximal primary belt 456 so as to releasably secure the proximal self-expanding member 407 of the ipsilateral leg 404 in a constrained state. The proximal primary belt 456 may be disposed about the self-expanding member 407 in a hoop-like configuration. The proximal self-expanding member 407 exerts outward radial pressure on the releasably secured belt 456. The primary proximal release wire 443 is axially moveable within the end loops 468 of the proximal primary belt 456 to allow for release of the belt by proximal retraction of the primary proximal release wire 443 in the same manner as described above with respect to other embodiments of the present invention.

Likewise, a distal portion 471 of the distal primary release wire 442 is disposed within end loops 472 of the second distal primary belt 462 which radially constrains the second distal self-expanding member 411. The second distal primary belt 462 is formed in a hoop configuration about the second distal self-expanding member 411 and the second distal self-expanding member 411 exerts outward radial force on the second distal primary belt 462. The distal primary release wire 442 is axially moveable within the end loops 472 of the second distal primary belt 462 to allow for release of the radial constraint as discussed above with respect to the proximal primary release wire 443 and as discussed above for other embodiments of the present invention. The distal portion 471 of the distal primary release wire 442 is also disposed within end loops 473 of the first distal primary belt 458 and radially constrains the first distal self-expanding member 422 in a similar fashion.

Although the distal primary release wire 442 and proximal primary release wire 443 are shown as two separate components, the release wires 442 and 443 could be combined into a single release member, such as the branched release wire 150 shown in FIG. 71 above. A branched release wire is capable of releasing multiple belts in a desired sequence by proper configuration of the lengths of the various branches of the wire. The relative amount of the release wire extending beyond the looped ends of the belt as indicated by reference numeral 156 in FIG. 71 controls the timing of the release of the belts. Alternatively, a single release wire may engage both distal and proximal primary belts 456, 458 and 462. As this single release wire 150 is moved proximally, the first distal primary belt 458 is first released, followed by the release of the second distal primary belt 462 and then release of the proximal primary belt 456.

A distal portion 474 of a secondary release member in the form of a secondary release wire 475 is disposed within end loops 476 of a secondary belt 464 which radially constrains the proximal self-expanding member 408 of the contralateral leg 405. The proximal self-expanding member 408 of the contralateral leg 405 exerts outward radial force on the secondary belt 464 when the self-expanding member 408 is in a constrained configuration. The secondary release wire 475 is axially moveable within the end loops 476 of the secondary belt 464.

Figures 27, 28, 28A, 29, 30:
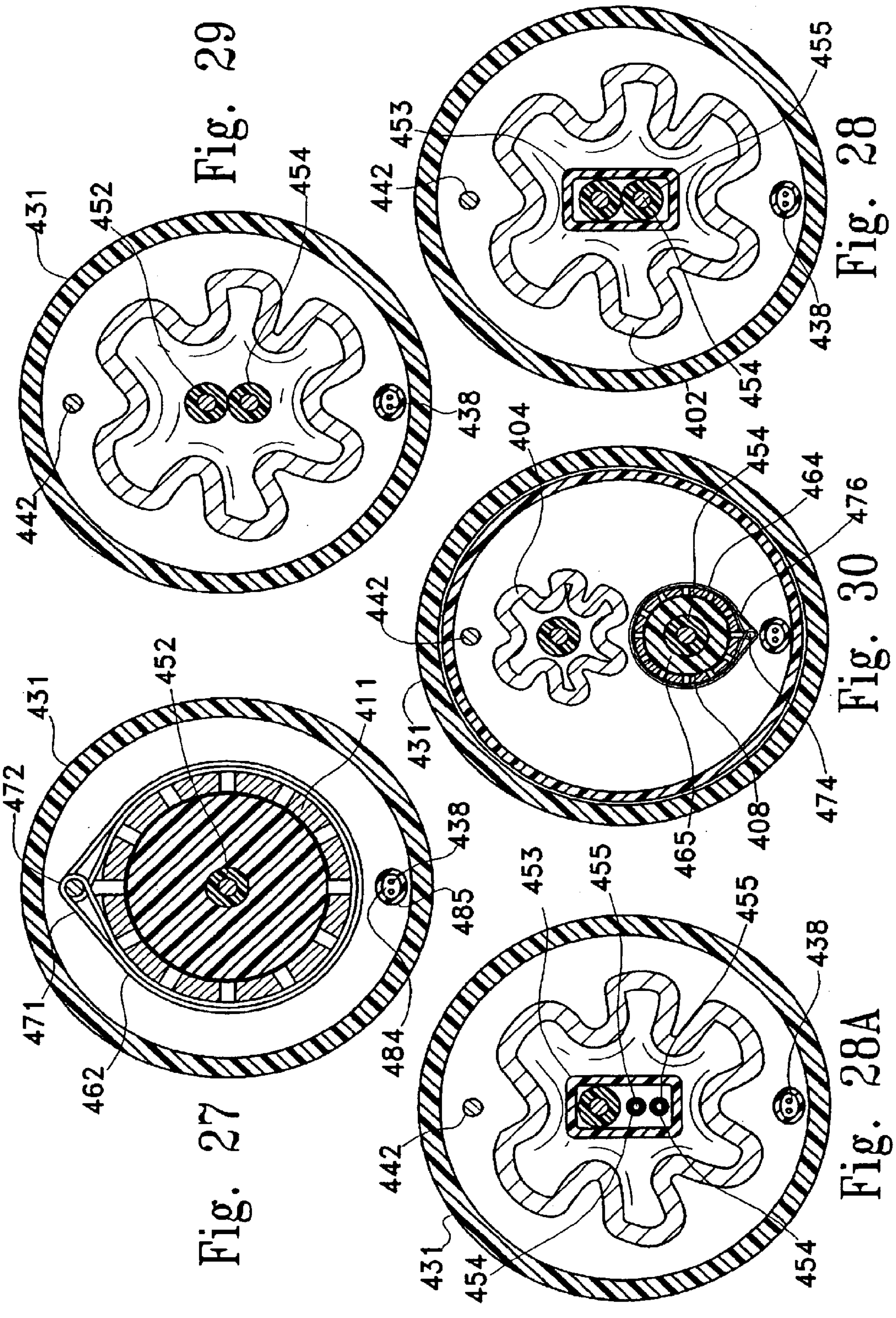
FIG. 27 is a transverse cross sectional view of the delivery system of FIG. 26 taken along lines 27—27 of FIG. 26.
FIG. 28 is a transverse cross sectional view of the delivery system of FIG. 26 taken along lines 28—28 of FIG. 26.
FIG. 28A is a transverse cross sectional view of an alternative embodiment of a secondary belt support member of a delivery system similar in function to that shown in FIG. 28.
FIG. 29 is a transverse cross sectional view of the delivery system of FIG. 26 taken along lines 29—29 of FIG. 26.
FIG. 30 is a transverse cross sectional view of the delivery system of FIG. 26 taken along lines 30—30 in FIG. 26.

A proximal end 477 of the secondary release wire 475 is secured to an actuator hub 478. A release strand 481 is secured to the actuator hub 478 and is attached to the secondary belt support member 454, and is shown by way of example in the embodiment of FIG. 26 as being looped through a hole 482 in the proximal end 483 of the secondary belt support member 454. Both portions of the release strand 481 that are looped through the proximal end 483 of the secondary belt support member 454 pass into an inner lumen 484 of a release strand tube 485 as seen in FIG. 27. The release strand tube 485 passes through an aperture 486 in the distal end 435 of the outer tubular member 431. Release strand 481 may comprise any filamentary thread or wire, metallic, polymeric, or otherwise, suitable for manipulation as will be herein described. It also may be braided or twisted if desired. The release strand 481 may be made of a filamentary thread of ePTFE.

As discussed above with respect to other embodiments, the release wires 442, 443 and 475 are generally made from a biocompatible high strength alloy such as stainless steel, but can also be made from any other suitable materials. Examples include other metallic alloys such as nickel titanium, non-metallic fibers such as carbon, polymeric materials, composites thereof, and the like. As discussed above, the diameter and stiffness of the release wires 442, 443 and 475 can be important with respect to the diameter and stiffness of the belts 456, 458, 462 and 464.

The configuration of the end loops 468, 472, 473 and 476 of the belts 456, 458, 462 and 464 may vary to suit the particular embodiment of the delivery system 400 and device to be delivered. For example, FIGS. 7C–7H illustrate a variety of belt and end loop configurations that may be suitable for delivery systems for bifurcated devices. Referring to FIG. 7C, belts 112 and 114 are shown having a twisted configuration which has a tendency to reduce snagging or entanglement of the belts 112 and 114 after deployment and release of the belts from a constrained configuration. In addition, FIG. 7C illustrates an angle a that belts 112 and 114 make with respect to line 125. In one embodiment, belts 112 and 114 would be substantially parallel to each other when in an unconstrained state such that this angle is approximately ninety degrees. It may also be desirable to use belts that have end loops that have different cross sectional areas (or transverse dimensions). For example, FIG. 7E shows end loops 81' and 81" constrained by release wire 24. We have found that, depending on the transverse dimension and material of loop 81' disposed within loop 81", elastic deformation of loop 81' can hinder the release process when release wire 24 is proximally retracted. Therefore, it may be desirable to make loop 81' from a material that is substantially smaller in cross sectional area or transverse dimension that that of loop 81". In a particular example, loop 81' is made from nickel titanium wire having a diameter of about 0.003 to about 0.005 inch, and loop 81" is made from the same material having a diameter ranging from about 0.005 to about 0.007 inch.

Figure 31:
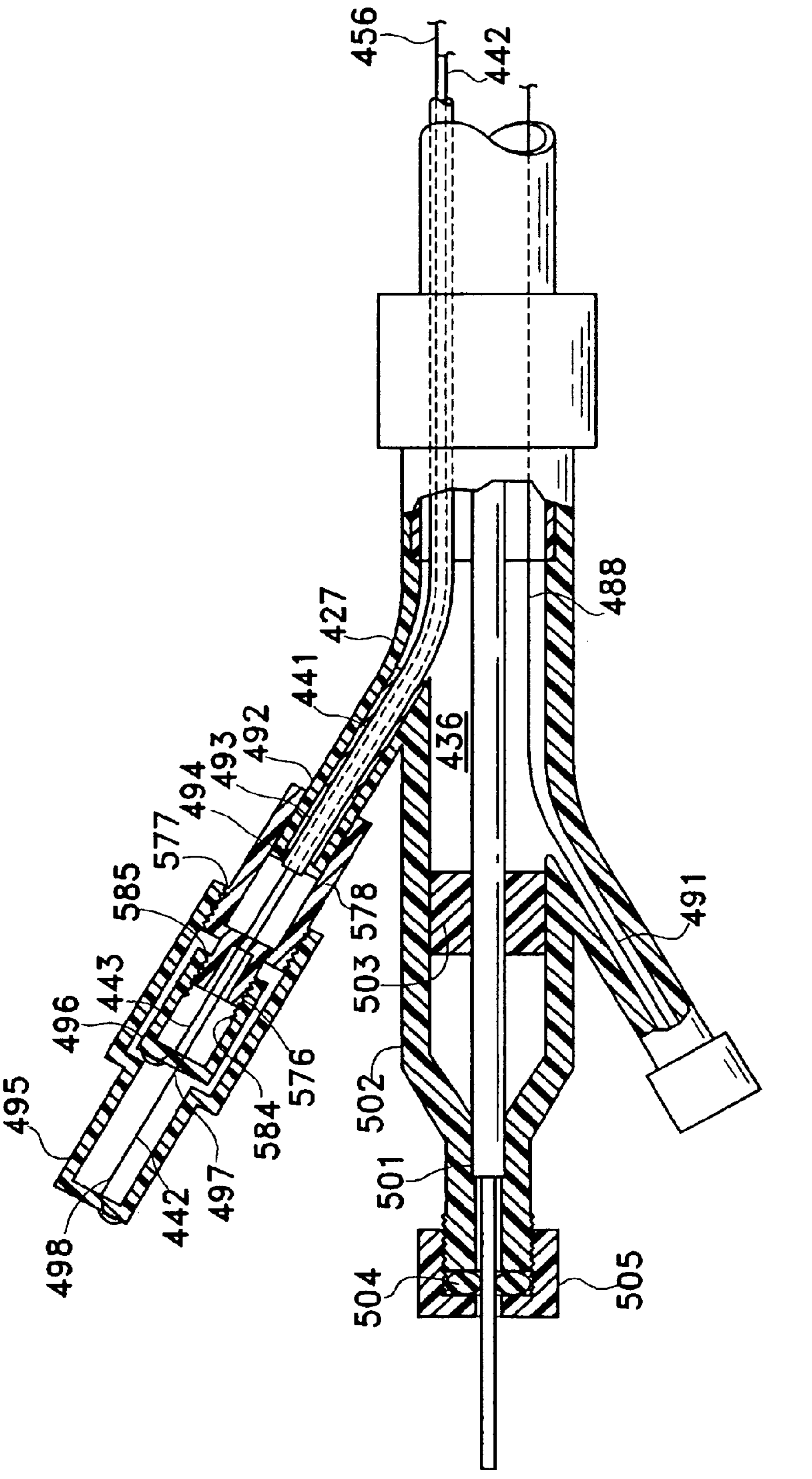
FIG. 31 is an elevational view in partial section of the proximal adapter of the delivery system of FIG. 23.

Inflation port 421 extends proximally from the proximal end 416 of the ipsilateral leg 404 of the graft 401. The inflation port 421 is coupled to a distal end 487 of the inflation tube 444 by a retention mechanism, such as a retention wire 488, the operation of which can be the same or similar to like embodiments of retention wire 285 discussed above. Typically, the retention wire 488 extends from the inflation port 421 proximally to the proximal adapter 427 of delivery system 400. The distal end 487 of the inflation tube 444 can be disengaged from the inflation port 421 by pulling on a proximal end 491 of retention wire 488, as shown in FIG. 31. The retention wire 488 may be a small diameter wire made from a material such as a polymer, stainless steel, nickel titanium, other alloy or metal, or composite; in a particular embodiment of the invention, retention wire 488 may be a spring formed of a variety of suitable spring materials. Alternatively, the retention wire 488 may have a braided or stranded configuration.

FIG. 31 illustrates proximal adapter 427 which is suitable for use with embodiments of the present invention. The proximal adapter 427 houses the proximal termination of the primary release wires 442 and 443, guidewire tube 444, retention wire 488 and release wire tube 441. The proximal adapter 427 has a first side arm 492 with an inner lumen 493 that secures the proximal end 494 of the release wire tube 441. The proximal adapter 427 has a distal primary release wire handle 495 and a proximal primary release wire handle 496 that are disposed in a nested configuration on the first side arm 492. A proximal end 497 of the proximal primary release wire 443 is secured to the proximal primary release-wire handle 496. A proximal end 498 of the distal primary release wire 442 is secured to the distal primary release wire handle 495. This configuration prevents the operator from inadvertently deploying or activating the proximal primary release wire 443 prior to deployment or activation of the distal primary release wire 442 which could result in an undesirable graft 401 deployment sequence.

A proximal end 501 of the guidewire tube 436 is secured within a central arm 502 of the proximal adapter 427 that has a potted section 503. A seal 504 may be disposed on a proximal end 505 of the central arm 502 for sealing around the guidewire lumen and preventing a backflow of fluid. The potted section 503 of the central arm 502 prevents any injected fluids from passing into the inflation material lumen 506 within the proximal adapter 427 or the inner tubular member 430. The other functions and features of the proximal adapter 427 may be the same or similar to those of the proximal adapters 42 and 323 shown in FIG. 1 and FIG. 17 and discussed above.

Figure 32:
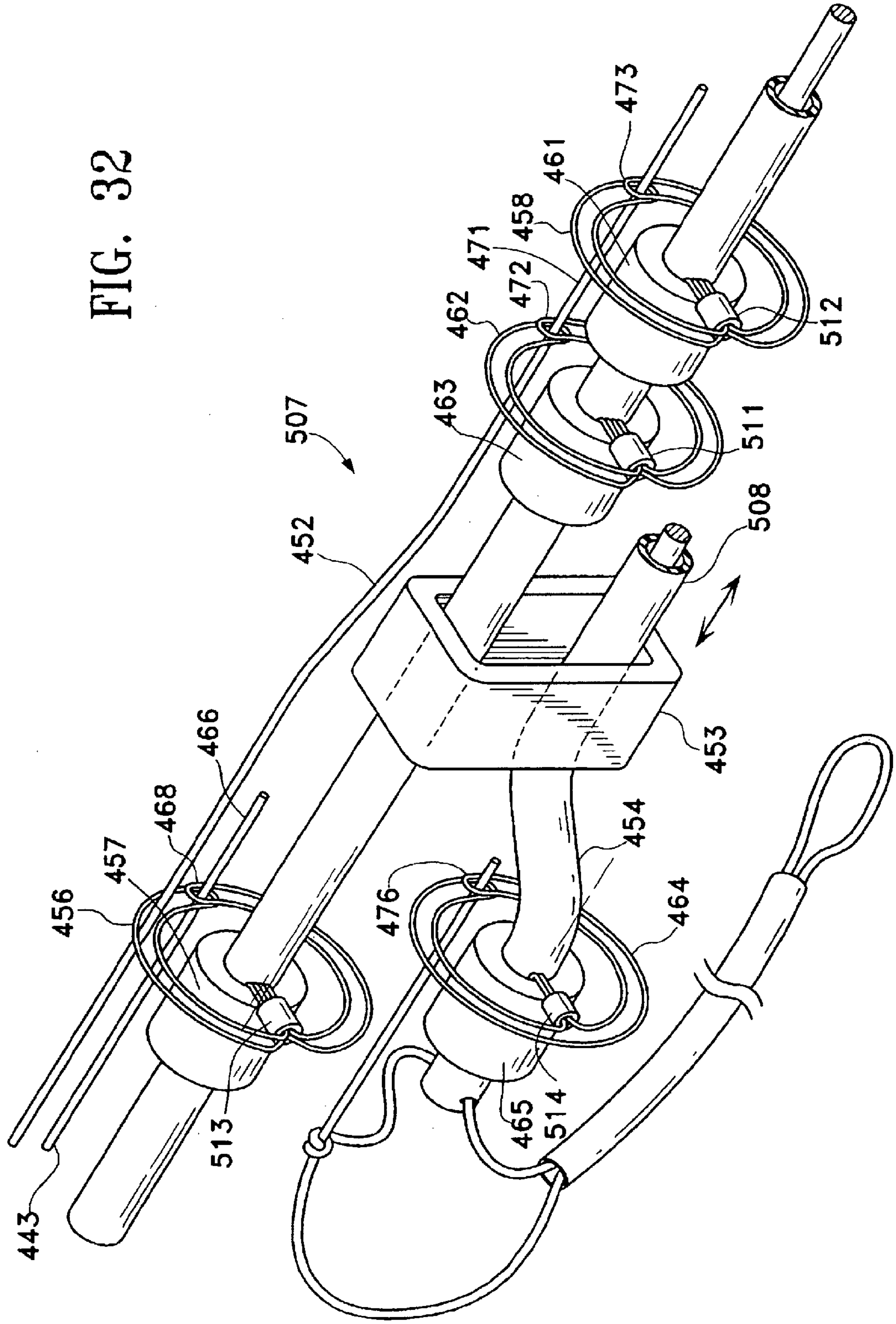
FIG. 32 is a perspective view of the belt support member assembly at a distal portion of the delivery system of FIG. 23.

FIG. 32 illustrates a belt support member assembly 507 of the delivery system 400. The distal end 508 of the secondary belt support member 454 is slidingly disposed within the secondary belt support member housing 453 which is secured to the primary belt support member 452. The second distal primary belt 462 is secured to the primary belt support member 452 (which in this embodiment is the guidewire tube 436) and extends radially therefrom through an optional second distal primary standoff tube 511. Similar optional first distal primary standoff tube 512, proximal primary standoff tube 513 and optional secondary standoff tube 514 are disposed on the first distal primary belt 458, proximal primary belt 456 and secondary belt 464, respectively.

In general, the various features and components (including, e.g., details of various embodiments of the release wires, the self-expanding members, belts, inflation port and tube, guidewire tube, standoff tubes, proximal adapter and its associated components, the materials and dimensions for each of the various components, etc.) as discussed herein with respect to those embodiments of FIGS. 1–18 may be used in the bifurcated embodiments of the present invention as discussed herein and as illustrated in FIGS. 19–32.

Figure 33:
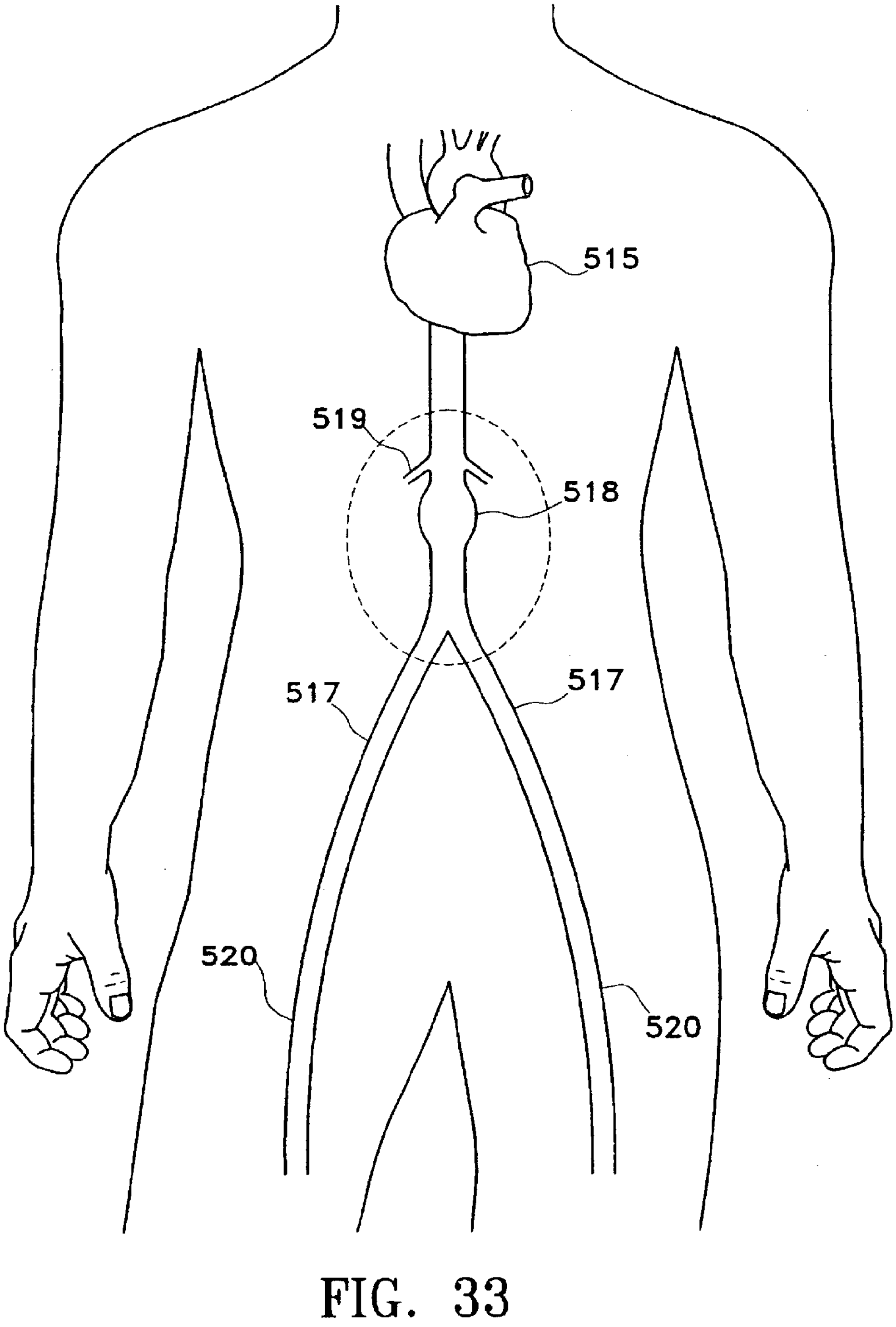
FIG. 33 illustrates a portion of the internal vasculature of a patient, including the aorta, iliac and femoral arteries branching therefrom.

In use, the delivery system 400 for delivery of a bifurcated intracorporeal device, specifically, a bifurcated graft 401, can be operated in a similar fashion to the delivery systems discussed above. FIG. 33 illustrates generally the anatomy of a patient's heart 515, aorta 516 and iliac arteries 517. The aorta extends from the heart 515 and descends into the abdomen of the patient's body. An aneurysm 518 is disposed in the aorta 516 just below the renal arteries 519. The aorta 516 branches into the right and left iliac arteries 517 below the aneurysm, which then become the femoral arteries 520.

Figure 34:
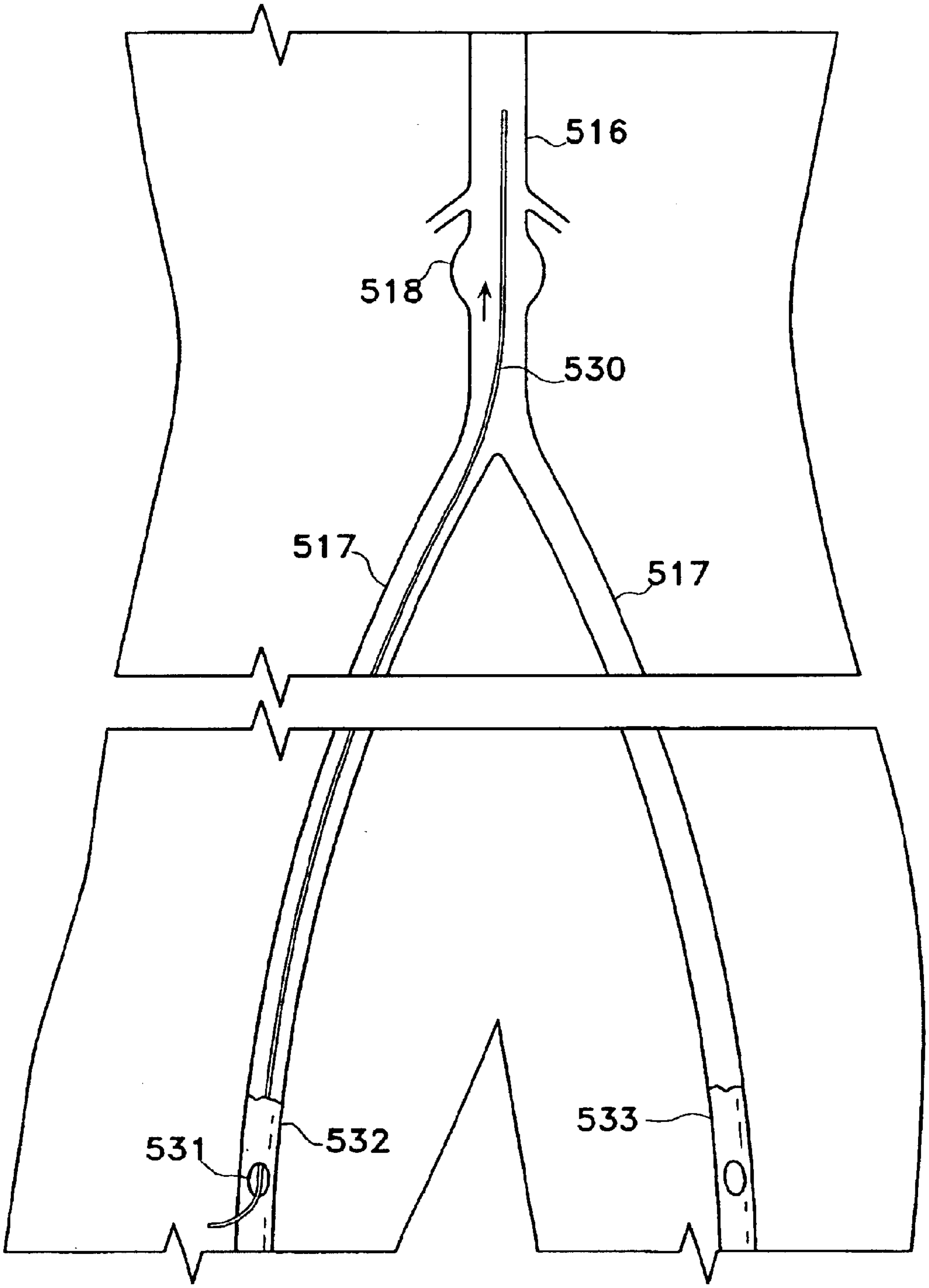
FIG. 34 is a magnified view of the abdominal aorta area of the patient shown in FIG. 33 and shows a guidewire positioned in the aorta from the right iliac artery.

One delivery procedure of the present invention begins with delivery of a first guidewire 530 into an access hole 531 in a femoral artery, the right femoral artery 532 for the procedure depicted in FIG. 34, and advanced distally through the iliac artery 517 and into the patient's aorta 516. Access into the femoral artery 532 is generally accomplished with a standard sheath and trocar kit, although sheathless access may also be employed. It should be noted that although the procedure described herein and illustrated in FIGS. 34–52 is initiated in the right femoral artery 532, the same procedure could be carried out beginning in the left femoral artery 532 with the orientation reversed. A vasodilator may optionally be administered to the patient at this point as previously discussed. If desired, a vasodilator may also be administered later in the procedure, but preferably prior to or simultaneous with the step of introducing inflation material into the graft 401.

Figure 35:
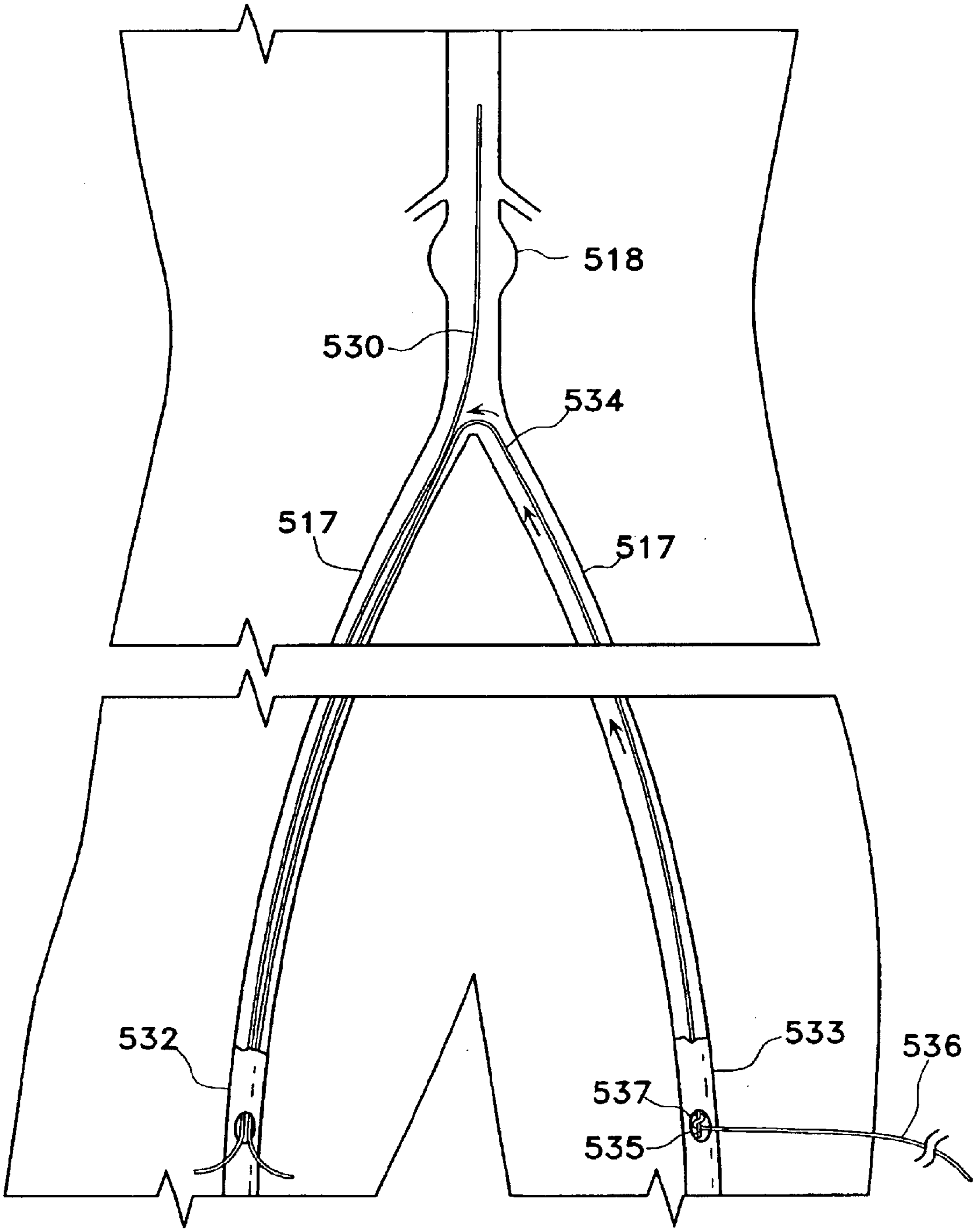
FIGS. 35–37 illustrate the magnified view of the abdominal aorta of the patient shown in FIG. 33 and depict a deployment sequence of the bifurcated endovascular stent graft of FIG. 19 with the delivery system of FIG. 23.

With the first guidewire 530 positioned across the aneurysm 518, a second guidewire 534 is then introduced into the ipsilateral or right femoral artery 532 and guided into the iliacs 517 and then back down into the contralateral or left femoral artery 533 as shown in FIG. 35. A distal end 535 of the second guidewire 534 may then be captured with a snare 536 or similar device inserted through an access hole 537 in the left femoral artery 533. The distal end 535 of the second guidewire 534 may then be pulled out of the left femoral artery 533 through the same left femoral artery access hole 537, providing a continuous length of wire passing through each iliac artery 517 via the left and right femoral artery access holes 531 and 537 as shown in FIG. 35.

Figure 36:
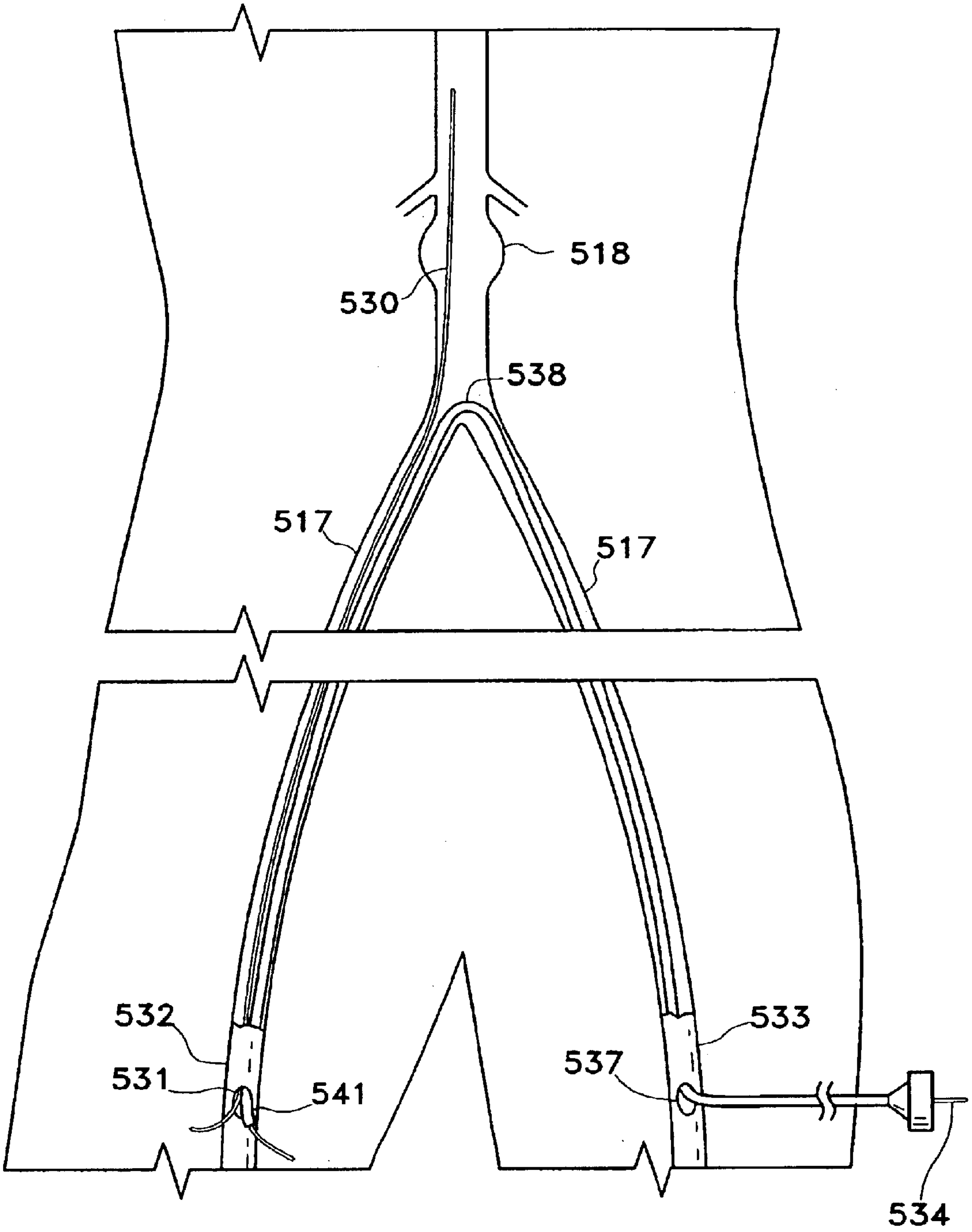
Figure 37:
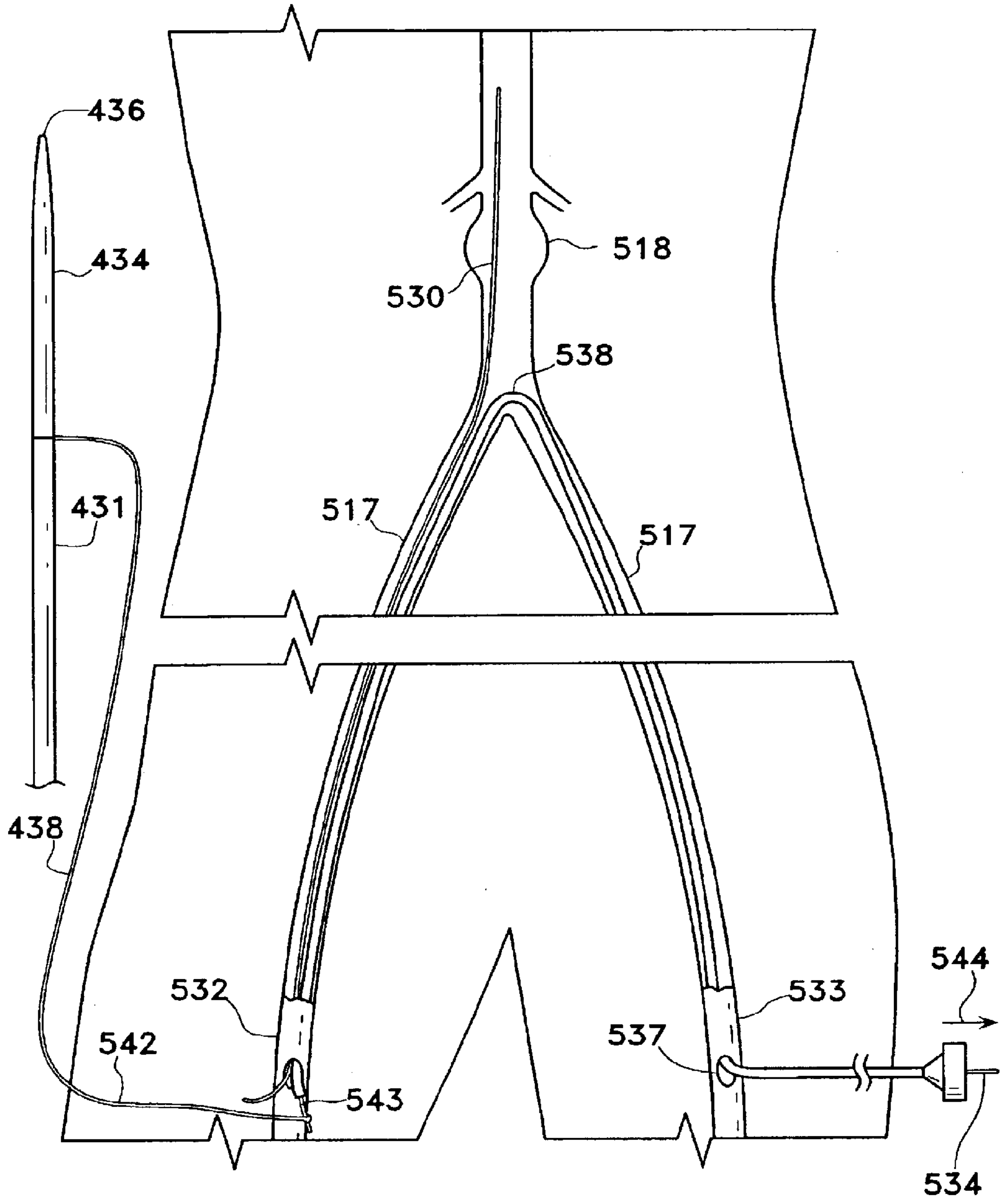

Once the second guidewire 534 exits the access hole 537 in the left femoral artery 533, a tubular catheter 538 may be advanced over the second guidewire 534 through the left femoral artery access hole 537 so as to extend out of the body from the access hole 531 in the right femoral artery 532 as shown in FIG. 36. This provides a continuous conduit between the right and left iliac arteries 517. With a distal end 541 of the tubular catheter 538 extending from the access hole 531 in the right femoral artery 532, a distal end 542 of the secondary release cable 438 may then be affixed to a proximal end 543 of the second guidewire 534 as shown in FIG. 37. For purposes of simplicity, the secondary release cable 438 is shown in, e.g., FIGS. 37–40 in schematic form as a single strand. However, it is understood that the term "secondary release cable" encompasses a single or multiple-component feature of the present invention that may be used to assist in the deployment of the graft. For instance, in the embodiment depicted herein, the secondary release cable 438 represents the combination of the release strand 481 and release wire tube 441 discussed above in conjunction with, e.g., FIG. 26. Other variations of this combination are within the scope of the present invention.

Figure 38:
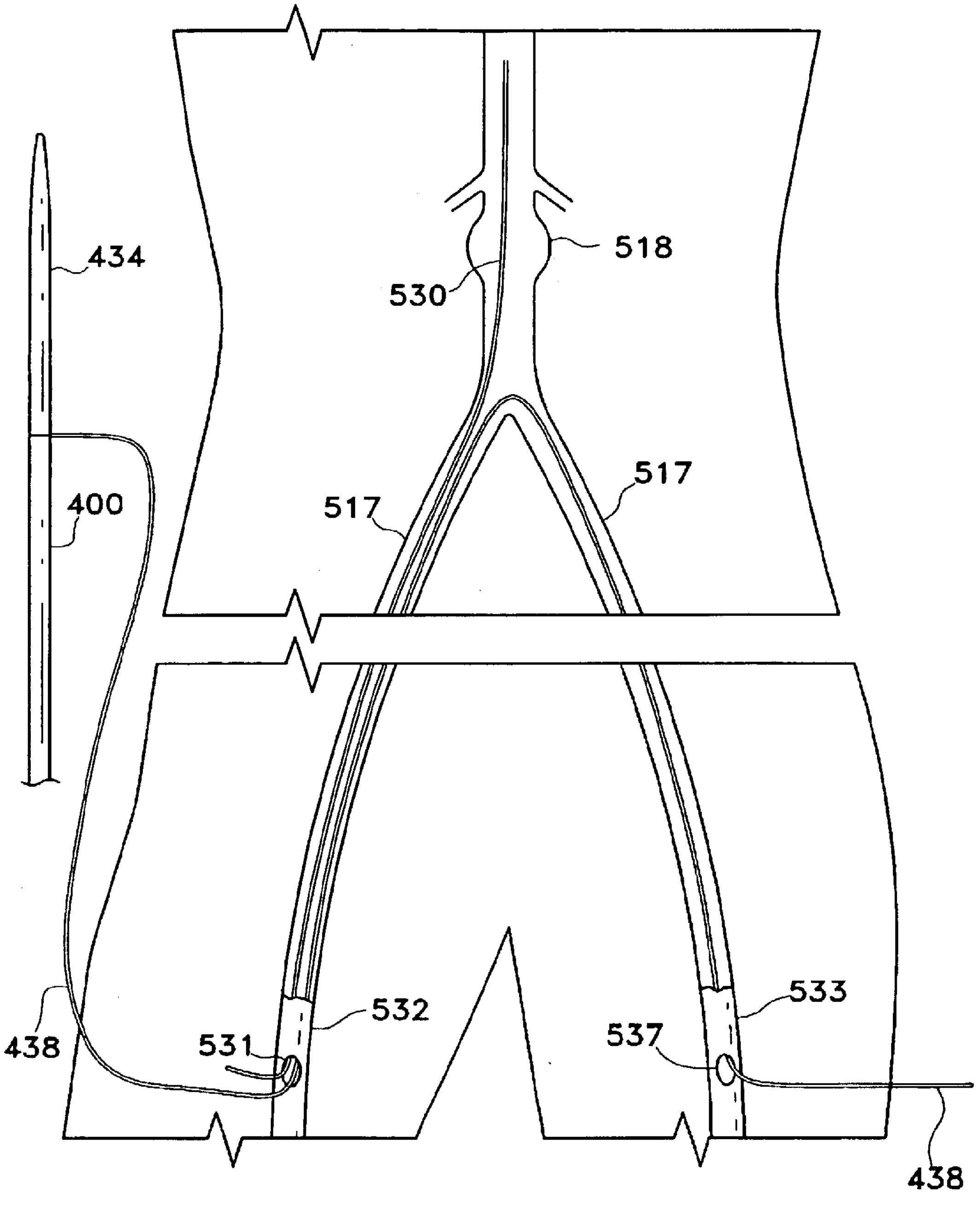
FIGS. 38–52 continue to illustrate a deployment sequence of the bifurcated endovascular stent graft of FIG. 19.

The second guidewire 534 is then pulled out of the tubular catheter 538 from the left femoral artery access hole 537, in the direction indicated by the arrow 544 in FIG. 37, so that the secondary release cable 438 then extends through the tubular catheter 538 from the right iliac artery to the left iliac artery. The tubular catheter 538 may then be withdrawn, leaving the secondary release cable 438 extending through the left and right iliac arteries 517 from the access hole 531 in the right femoral artery 532 to the access hole 537 in the left femoral artery 533 as shown in FIG. 38. The first guidewire 530 remains in position across the aneurysm 518.

Figure 39:
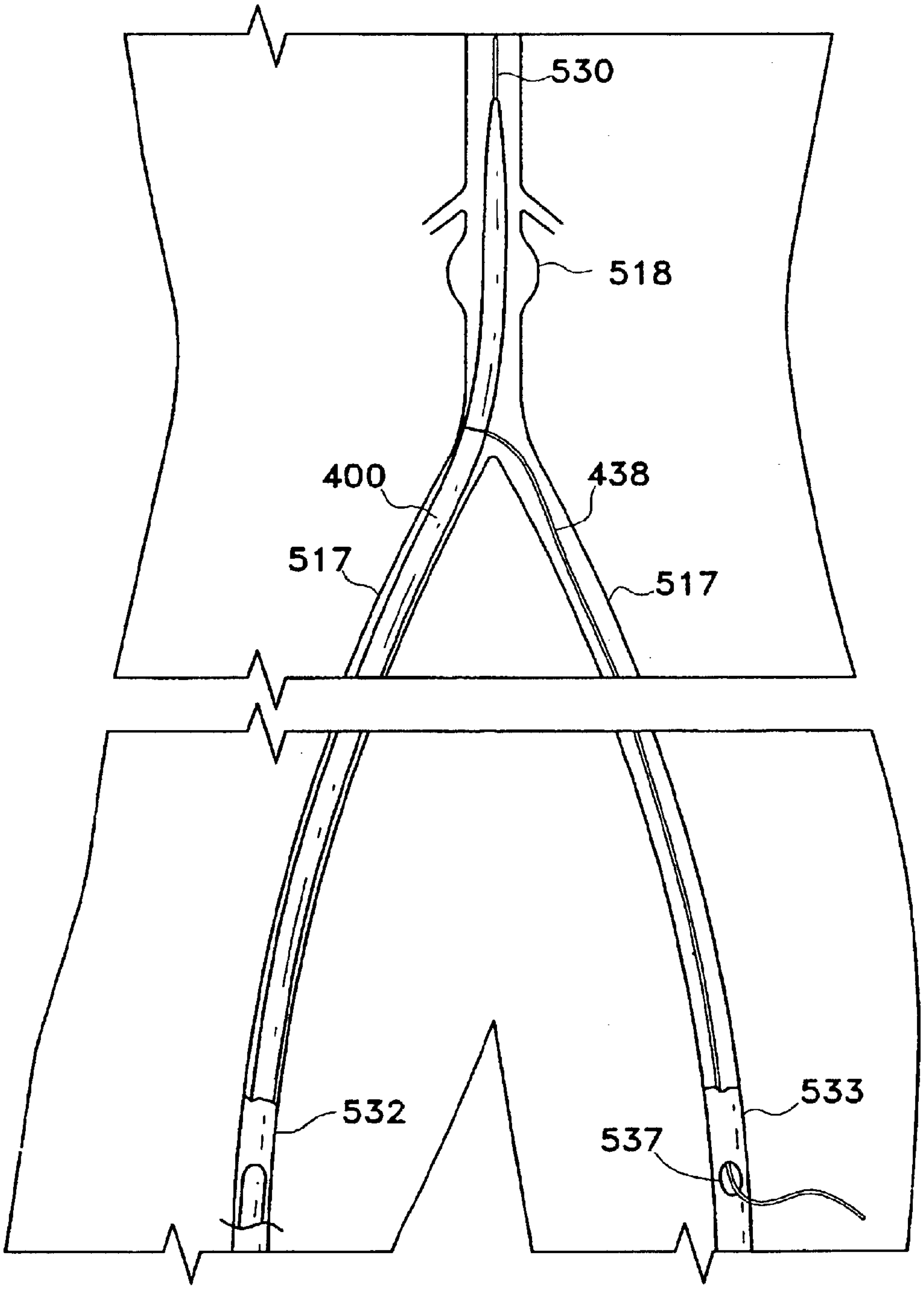

The delivery system 400 is then advanced into the patient's right femoral artery 532 through the access hole 531 over the first guidewire 530 as shown in FIG. 39. It may be desirable to apply tension to the secondary release cable 438 as the delivery system 400 is advanced to the vicinity of the aneurysm 518 so as to remove slack in the cable 438 and prevent tangling of the cable 438 or the like. Tension on the secondary release cable 438 may also help to prevent twisting of the delivery system 400 during insertion.

Figure 37A:
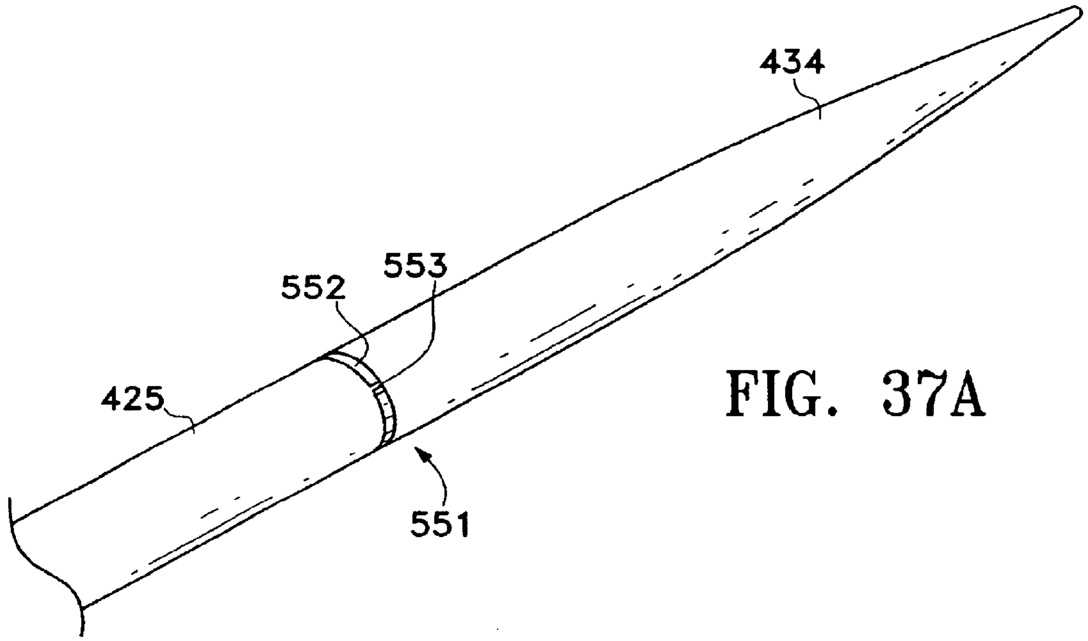
FIG. 37A is a perspective view of a marker disposed on the delivery system distal section in the vicinity of the nosepiece.
Figure 37B:
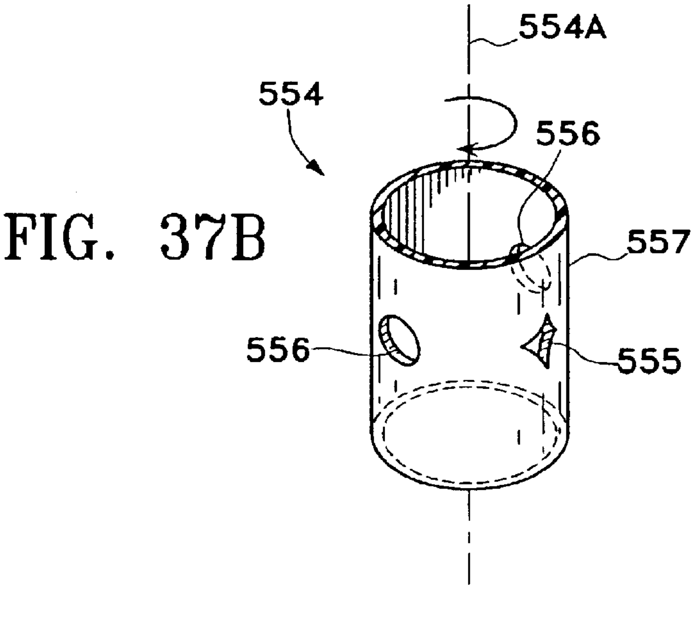
FIG. 37B is a perspective view of an alternative embodiment of a marker for use in the delivery system of the present invention.

FIGS. 37A–B show an optional marker band that may disposed adjacent nosepiece 434 or generally in the vicinity of the distal end 425 of the elongate shaft 423 of the delivery system 400. Such a marker band 551 may also be integral with the delivery system 400; for example, it may be incorporated as part of the distal nosepiece 434. A useful marker 551 can be one that does not add to the profile of the delivery system 400 as shown in FIG. 37A (i.e., one that does not give the delivery system 400 a higher diameter). The embodiments of FIGS. 37A–B are useful in the present embodiment, although they may be used in the embodiments discussed above. Such a marker may be used to aid the operator in introducing the delivery system 400 without twisting.

For example, the marker embodiment 551 of FIG. 37A comprises a marker body 552 in the form of a simple discontinuous ring made of an appropriate radiopaque material (e.g., platinum, gold, etc.) visible under fluoroscopy, etc. The cross section of the ring may be asymmetric so that under fluoroscopy the cross section may be seen in the vicinity of the discontinuity 553. The operator will be able to tell if the delivery system 400 is twisted by how the ring 552 is presented under fluoroscopy. Alternatively, ring 552 may be continuous but have a notch or similar cutout to serve the same purpose.

The embodiment 554 of FIG. 37B is an example of such a marker. Here, both a notch 555 and two circular holes 556 have been cut out of the marker body 557 for easier determination of its orientation when disposed on the notch or other part of the delivery system 400. For instance, in an orientation where the two circular holes 556 are aligned with respect to the fluoroscope field of view, the user will see a single circular hole to the left of a triangular or vee-shape cutout 555 on the side of the marker 554. As the angular orientation of the device 400 (and thus the marker 554) about the longitudinal axis changes, the appearance of the two circular holes 556 and side notch 555 will change. If the device is twisted clockwise ninety degrees from this orientation along its central longitudinal axis 554A, for instance, the circles 556 will largely disappear from view and the side notch 555 will generally appear in the front of the field of view as a symmetric diamond. Comparing these views will allow the user to know that the entire delivery system 400 has twisted about ninety degrees. Keeping the same orientation, then, will be made easier with such a marker 554.

For each of the embodiments of FIGS. 37A–B, variations in the shape, number, orientation, pattern and location of the notch 553 and 555, holes 556 or other discontinuity, as well as various marker body dimensions cross sectional shape, etc., may be realized, as long as the marker 551 and 554 is configured so that the angular orientation of the delivery system 400 may readily be determined by the user under fluoroscopy or similar imaging technique.

Figure 40:
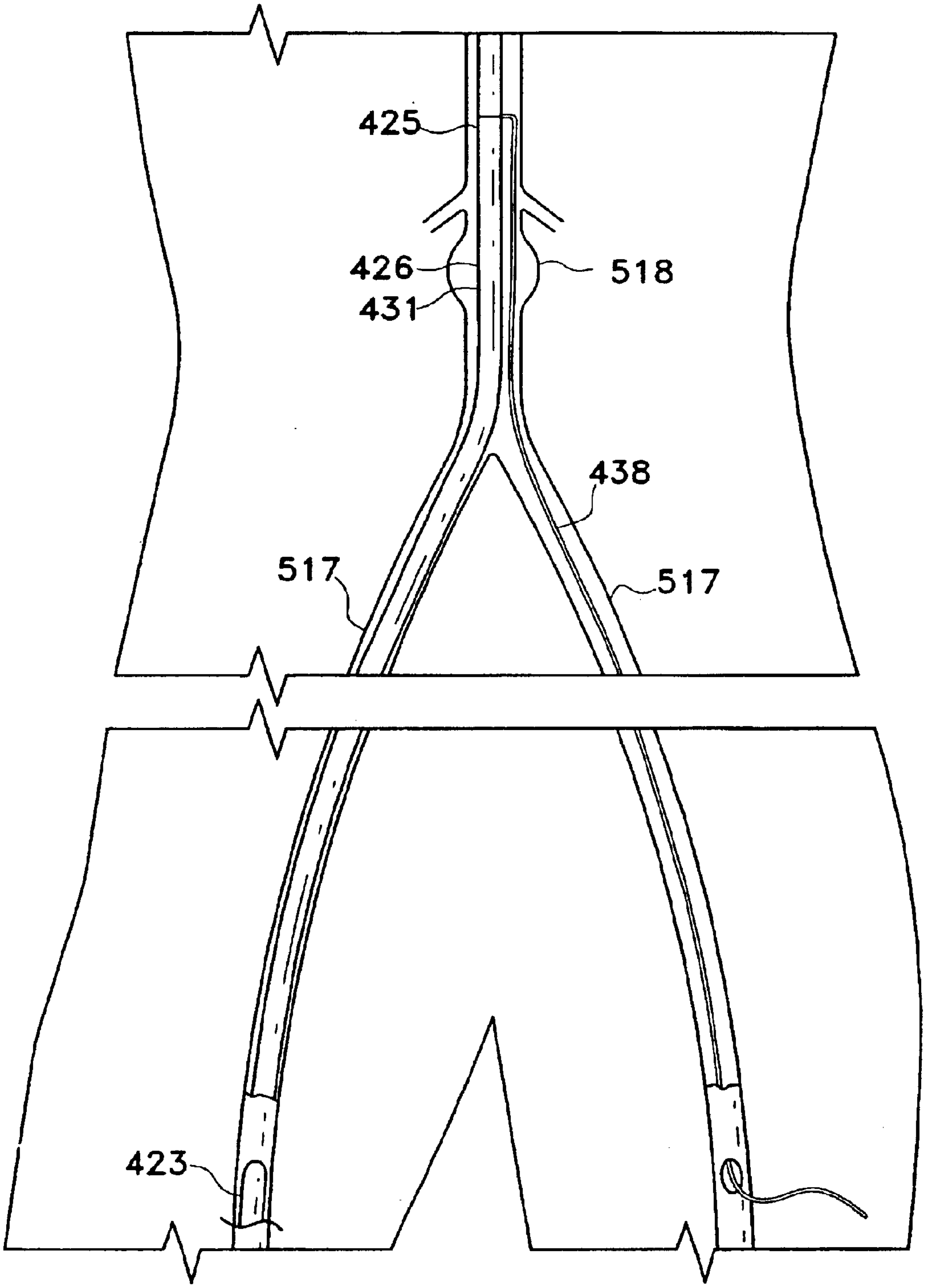
Figure 44:
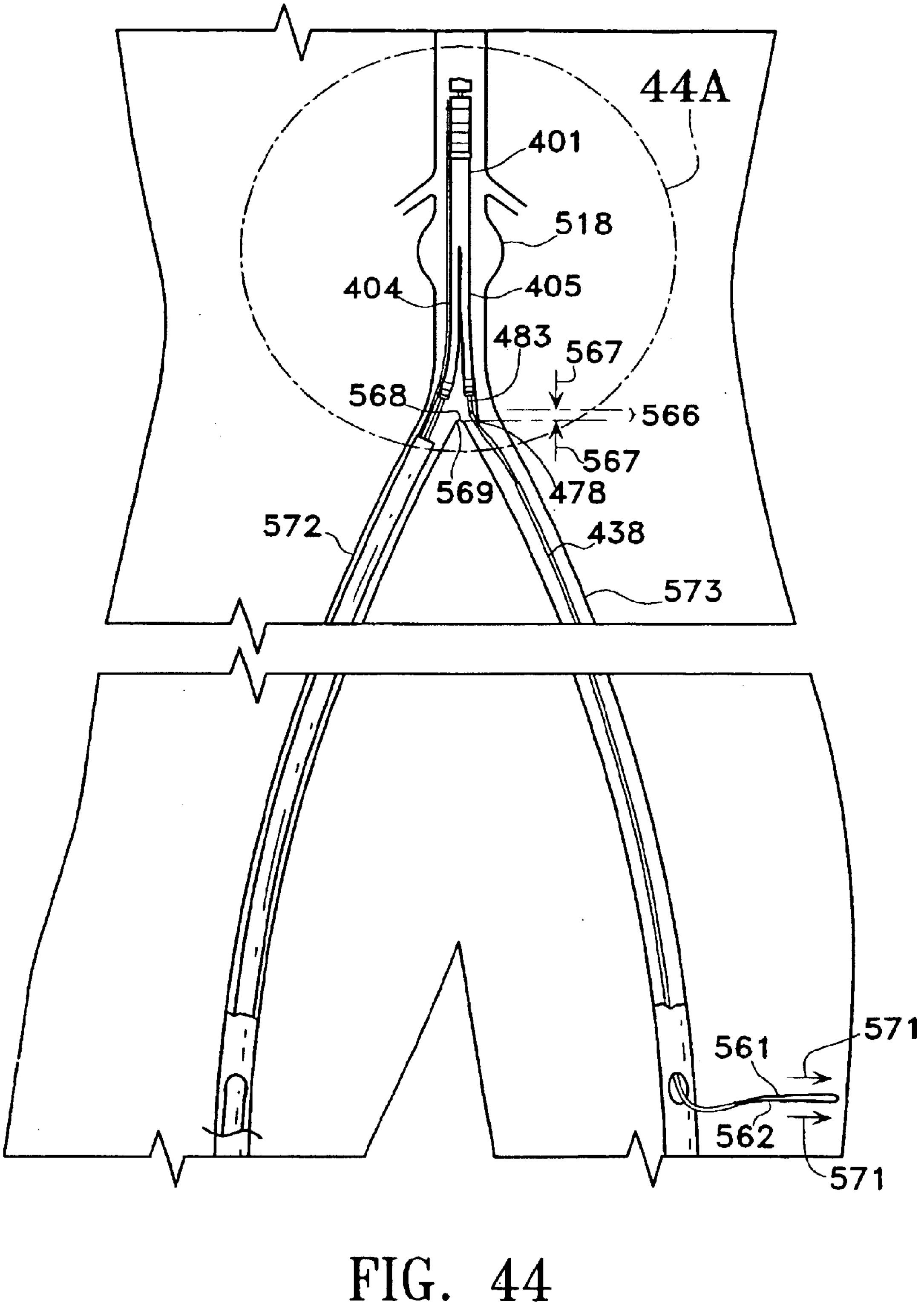
Figure 44A:
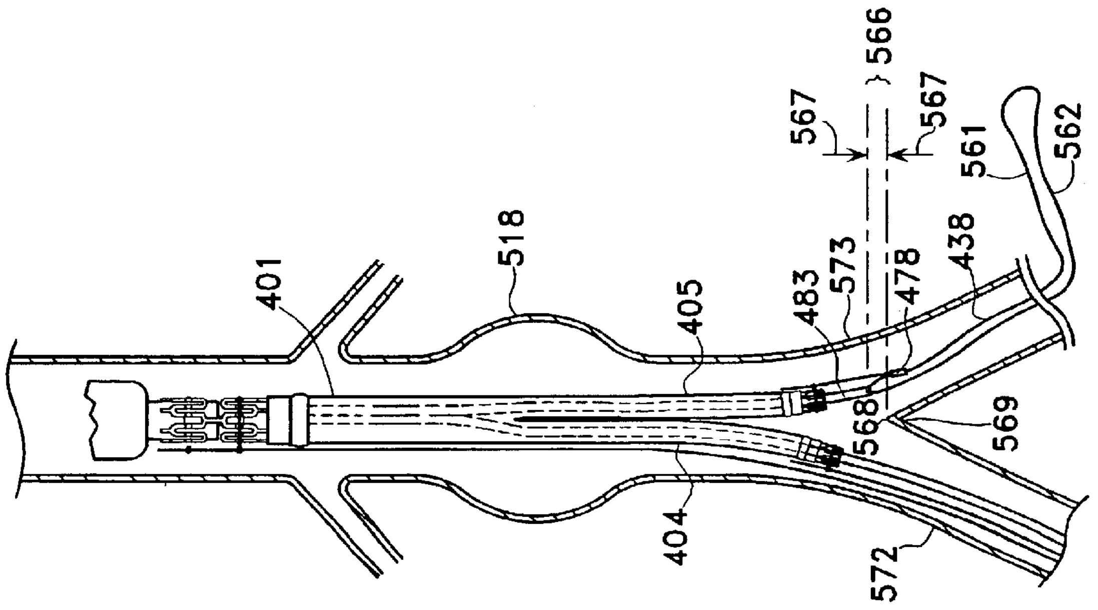

The delivery system 400 is positioned in a location suitable for initiating the deployment process, such as one in which the distal end 425 of the delivery system 400 is disposed beyond, or distal to the position in which the graft 401 will be placed, as shown in FIG. 40. This position allows the proximal end 483 of the secondary belt support member 454 to be laterally displaced without mechanical interference from the patient's vasculature. Such clearance for lateral displacement is shown in FIG. 44.

Once the distal section 426 of the elongate shaft 423 and the endovascular graft 401 are positioned, the deployment process is initiated. First, the outer tubular member 431 is proximally retracted by pulling on the proximal end 433 of the outer tubular member 431 relative to the inner tubular member 430. The inner tubular member 430 should be maintained in a stable axial position, as the position of the inner tubular member 430 determines the position of the constrained bifurcated graft 401 prior to deployment. Upon retraction of the outer tubular member 431, the constrained bifurcated graft 401 is exposed and additional slack is created in the secondary release cable 438 as shown in more detail in FIG. 41.

Alternatively, a variety of different components may be substituted for the outer tubular member 431 in some of the embodiments of the invention. For instance, a shroud, corset, mummy-wrap, or other cover may be released or actuated to expose the constrained graft 401 after the delivering system 400 is introduced into the vasculature.

Figure 28B:
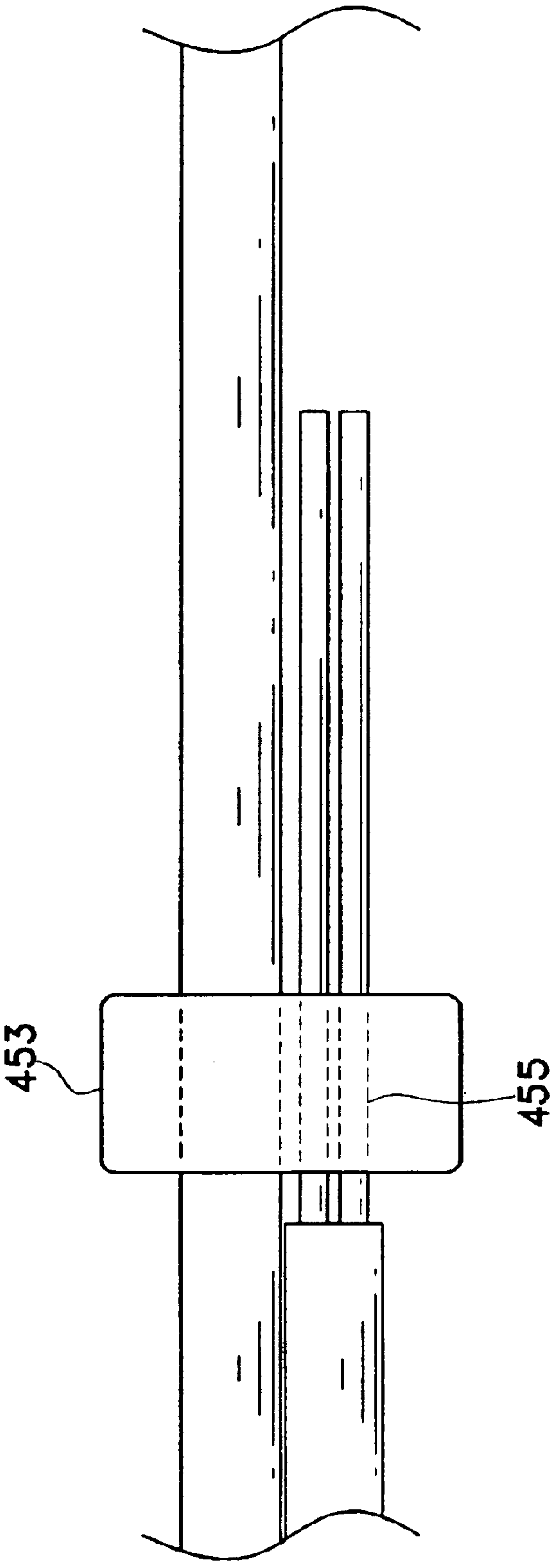
FIG. 28B is an elevational view of the alternative embodiment of the secondary belt support member of FIG. 28A.
Figure 41:
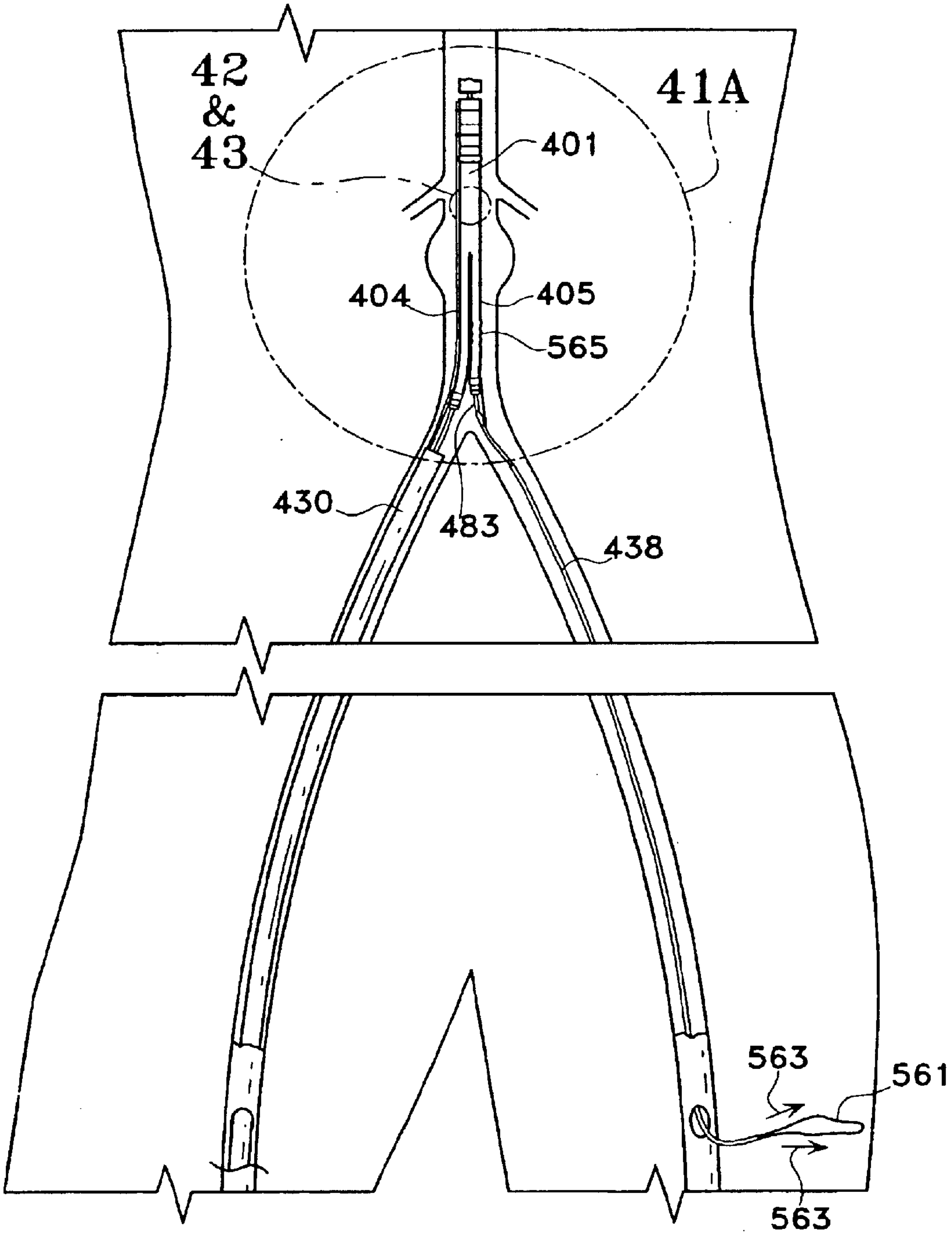
Figure 42:
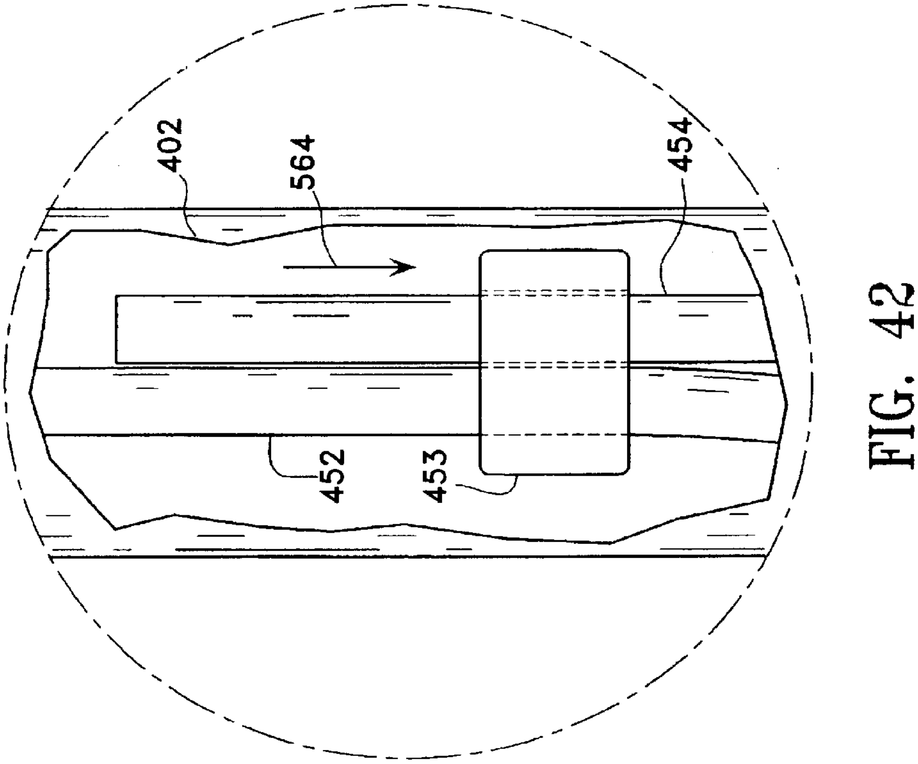
Figure 41A:
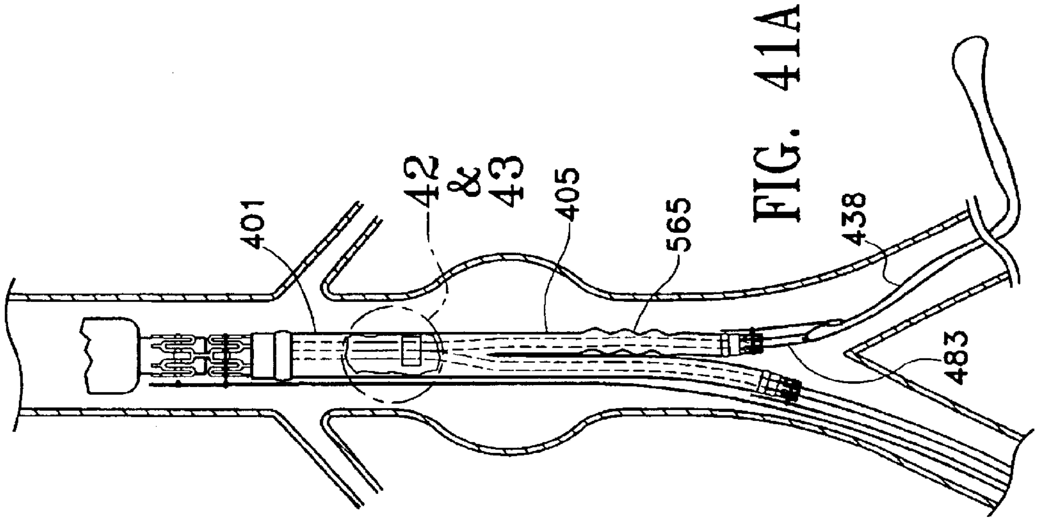
Figure 43:
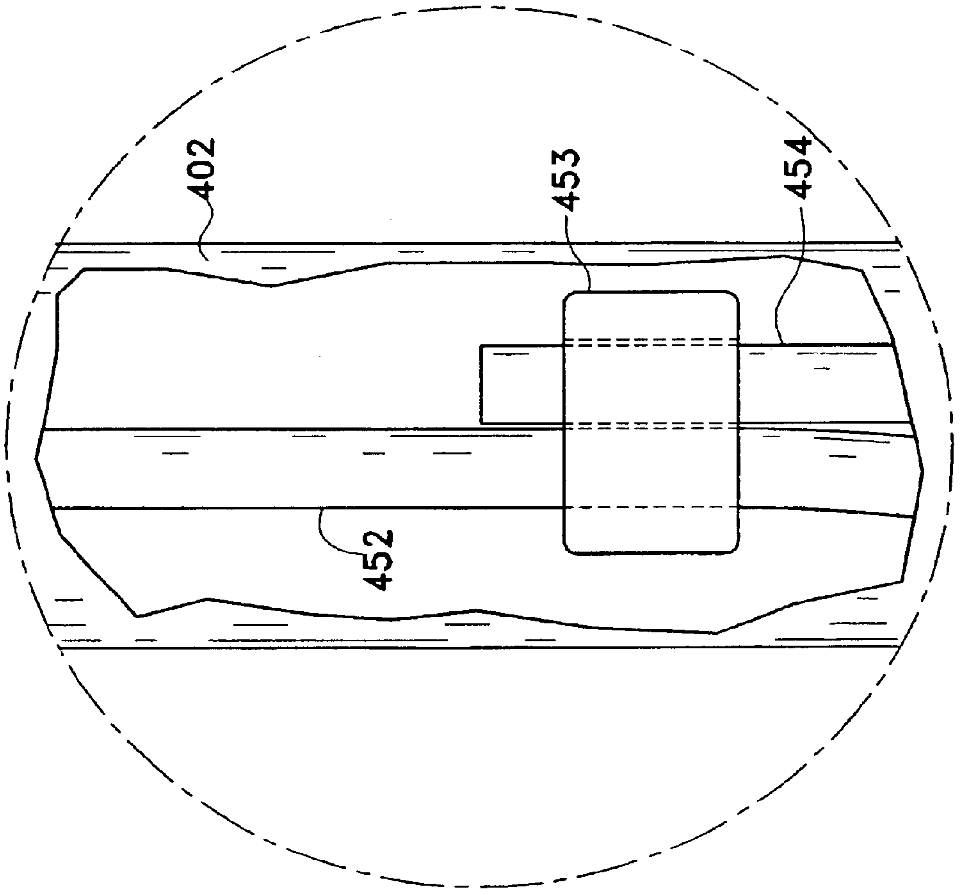

The slack in the secondary release cable 438 is taken up by applying tension to both lengths 561 and 562 of the release strand 481 as shown by the arrows 563 in FIG. 41. As tension continues to be applied to both lengths 561 and 562 of the release strand 481, the secondary belt support member 454 begins to slide within the secondary belt support member housing 453 in a proximal direction as shown by the arrow 564 in FIG. 42. The secondary belt support member 454 continues to slide proximally until all the slack is removed from an axially compressed or folded portion 565 of the contralateral leg 405 of the graft 401 shown in FIG. 41 and the primary and secondary belt support members 452 and 454 are oriented relative to the secondary belt support member housing 453 as generally shown in FIG. 43. Rotational movement of the secondary belt support member 454 relative to the secondary belt support member housing 453 is prevented by the non-circular or asymmetric cross section of the member 454 as shown in FIGS. 28–28B. This prevents the contralateral leg 405 from twisting or becoming entangled with other components of the graft 401 or delivery system 400 during deployment.

Axial compression of all or a portion of the contralateral leg 405 while the graft 401 is in a constrained state within the delivery system 400 prior to deployment allows the axial position of the two proximal self-expanding members 407 and 408 to be axially offset from each other. Alternatively, graft legs 404 and 405, having different lengths may be used to prevent overlap of the self-expanding members 407 and 408 within the delivery system 400. The cross sectional profile or area of the overlap self-expanding members 407 and 408 is generally greater than that of the adjacent polymer material portion of the legs 404 and 405 of the graft 401, so eliminating the overlap can be desirable. The self-expanding members 407 and 408 are typically made of a metal or metallic alloy and maintain a cylindrical configuration, even when in a constrained state. The polymer material of the legs 404 and 405 or main body portion 402 of the graft 401, by contrast, is relatively soft and malleable and can conform to the shape of whatever lumen in which it may be constrained. Placing both proximal self-expanding members 407 and 408 adjacent each other in a compressed state at a single axial position within the delivery system 400 would require a configuration in which two objects having an approximately circular cross section are being placed within another circular lumen. Such a configuration generates a significant amount of wasted or unused cross sectional area within that axial position of the delivery system 400 and would likely result in less flexibility and greater cross section than a delivery system 400 in which the proximal self-expanding members 407 and 408 are axially offset.

A gap 566 indicated by the arrows 567 in FIG. 44 allows the proximal end 483 of the secondary belt support member 454 and secondary release wire actuator hub 478 to move in a lateral direction without mechanical interference from the carina 568 of the iliac artery bifurcation 569. Gap 566 may vary depending on the patient's particular anatomy and the specific circumstances of the procedure.

The lateral movement of the contralateral leg 405 and secondary belt support member 454 is accomplished by application of tension on both lengths 561 and 562 of the release strand 481 as shown by the arrows 571 in FIG. 44. This movement away from the primary belt support member 452 allows the secondary belt support member 454 to transition from alignment with the right iliac artery 572 to alignment with the left iliac artery 573 as shown in FIG. 44.

Figure 45:
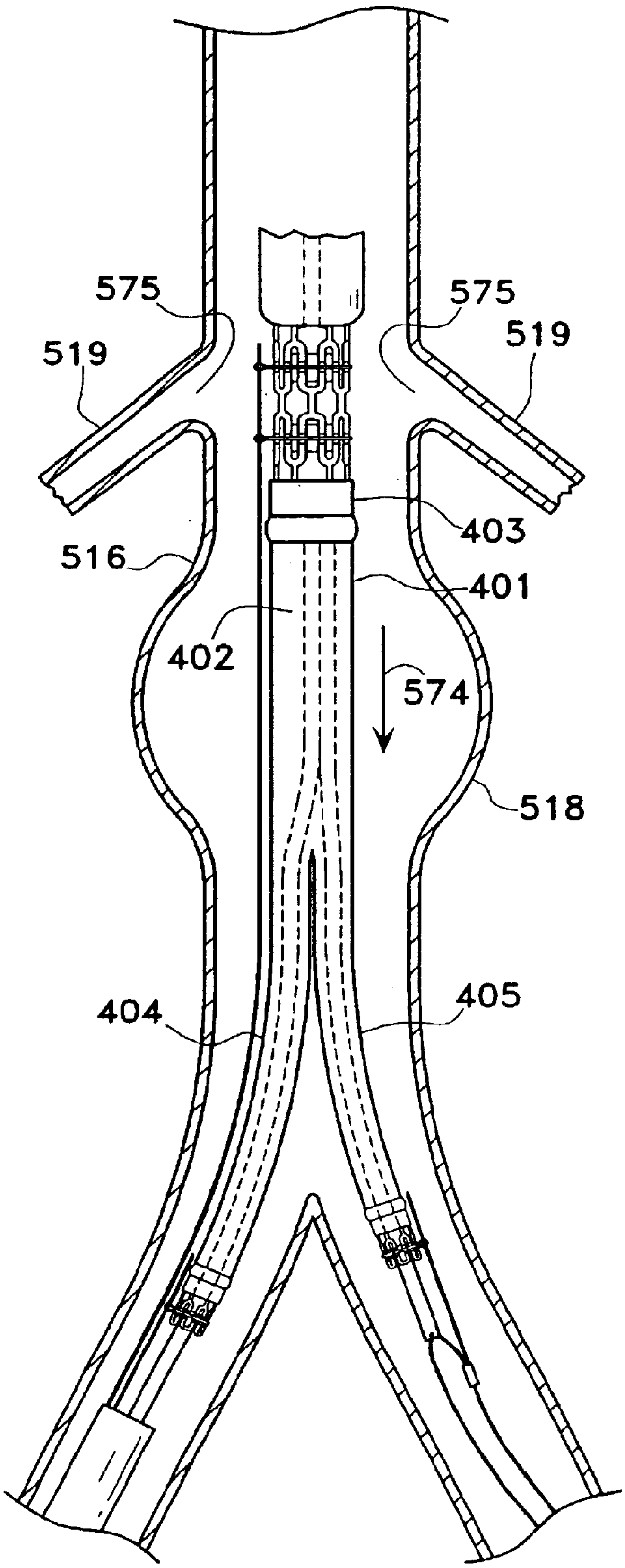

Once the ipsilateral leg 404 of the graft 401 and contralateral leg 405 of the graft 401 are aligned with the right and left iliac arteries 572 and 573, respectively, the delivery system 400 may then be retracted proximally, as shown by the arrow 574 in FIG. 45, so as to reposition the distal section 426 of the elongate shaft 423 and the bifurcated graft 401 into the desired position for deployment as shown in FIG. 45.

As discussed above with respect to placement of a tubular graft 11 embodiment of the present invention, when deploying the graft 401 in the abdominal aorta 516 it is generally desirable to ensure that the distal end 403 of the graft main body portion 402 is installed proximal to, or below, the renal arteries 519 in order to prevent their significant occlusion.

However, the distal self-expanding members 411 and 422 of the graft 401 may, depending upon the anatomy of the patient and the location of the aneurysm 518, partially or completely span the ostia 575 of one or both renal arteries 519. It can be desirable, however, to ensure that ostia 575 of the renal arteries 519 are not blocked by the distal end 403 of the graft main body portion 402. As discussed previously, a variety of imaging markers 551 and 554 may be used on either or both the delivery system 400 and the graft 401 itself to help guide the operator during the graft positioning process.

After proper positioning, the first and second distal self-expanding members 411 and 422 may then be deployed. The operator first unscrews or otherwise detaches a threaded portion 576 of the distal primary release wire handle 495 from an outer threaded portion 577 of a first side arm end cap 578 shown in FIG. 31. Next, the distal primary release wire handle 495 is proximally retracted, which in turn retracts the distal primary release wire 442 in a proximal direction, as shown by the arrow 581 in FIG. 46. As the distal end 582 of the distal primary release wire 442 passes through the end loops 472 and 473 of the first distal primary belt 458 and second distal primary belt 462, the end loops 472 and 473 are released, freeing the first distal self-expanding member 422 and second distal self-expanding member 411 to self-expand in an outward radial direction so to contact an inner surface 583 of the patient's aorta 516. The first and second distal primary belts 458 and 462 remain secured to the primary belt support member 452 and will eventually be retracted from the patient with the delivery system 400 after deployment is complete.

Figure 46:
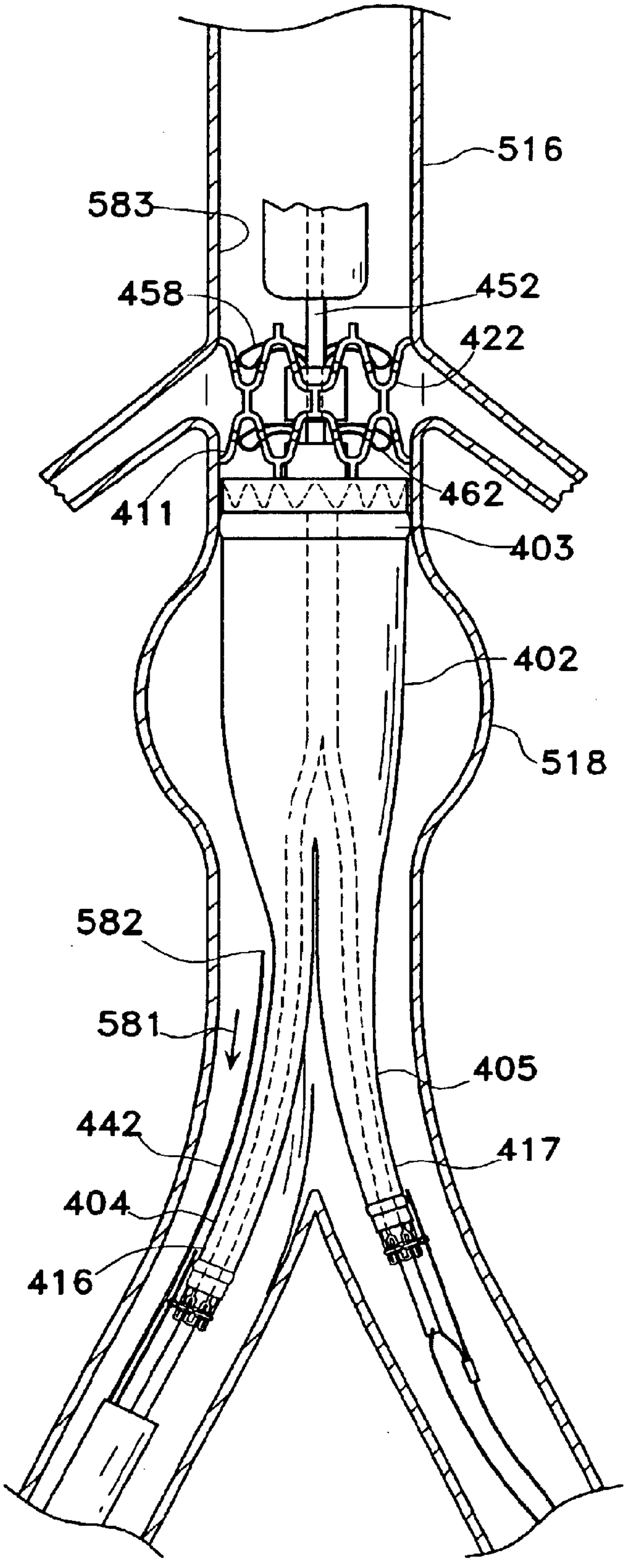

As the first and second distal self-expanding members 411 and 422 expand and contact the aorta 516, a distal end 403 of the graft main body portion 402 opens with the self-expanding members 411 and 422 and promotes opening of the graft polymer material portion from the flow of blood into the distal end 403 of the graft main body portion 402 with a "windsock" effect. As a result, once the first and second distal self-expanding members 411 and 422 are expanded to contact the aorta inner surface 583, the graft main body portion 402 and legs 404 and 405 balloon out or expand while the proximal ends 416 and 417 of the legs 404 and 405 of the graft 401 remain constricted due to the constrained configuration of the proximal self-expanding members 407 and 408 of the ipsilateral and contralateral legs 404 and 405, as shown in FIG. 46. At this point, there typically will be partial or restricted blood flow through and around the graft 401.

Figure 47:
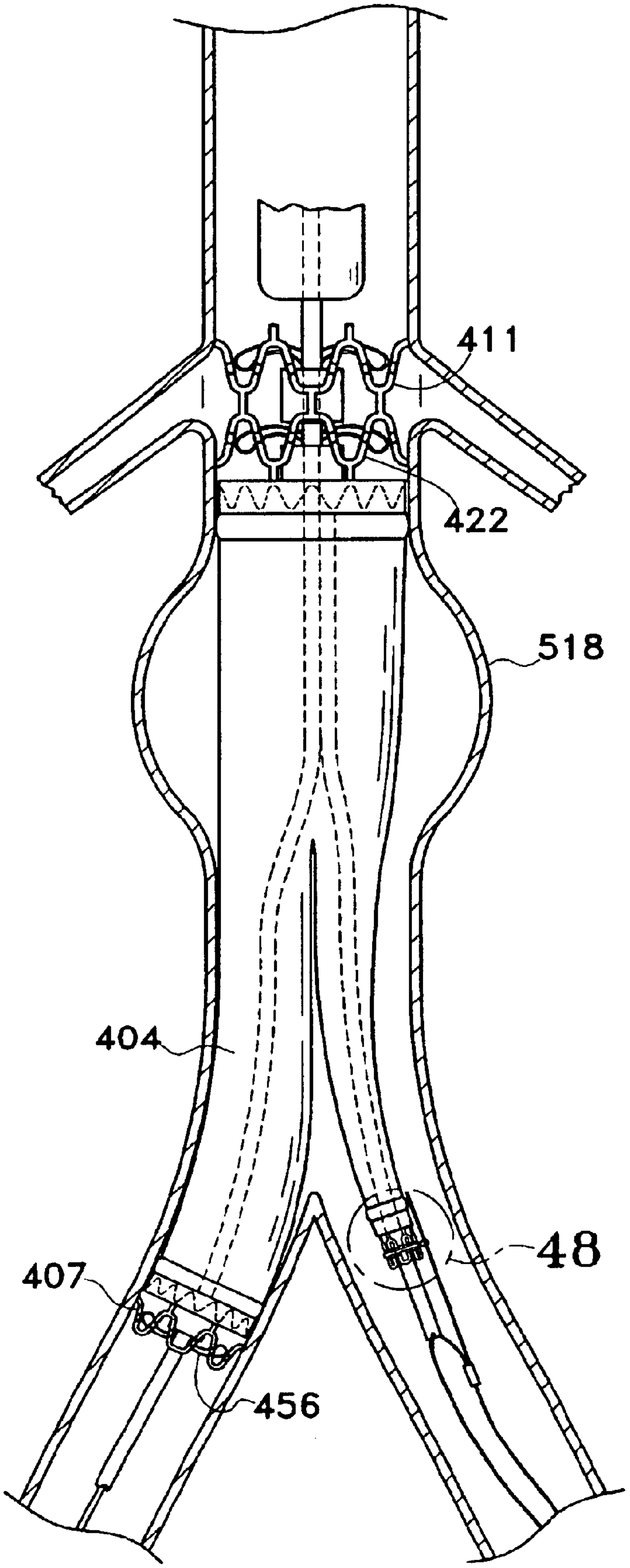

Next, the proximal self-expanding member 407 of the ipsilateral leg 404 is deployed. Deployment of the first and second distal self-expanding member 411 and 422 has exposed the proximal primary release wire handle 496, making it accessible to the operator. A threaded portion 584 of the proximal primary release wire handle 496 is unscrewed or otherwise detached from an inner threaded portion 585 of the first side arm end cap 578. The proximal primary release wire handle 496 may then be retracted proximally so as to deploy the proximal primary belt 456 and proximal self-expanding member 407 of the ipsilateral leg 404 as shown in FIG. 47.

Figure 48:
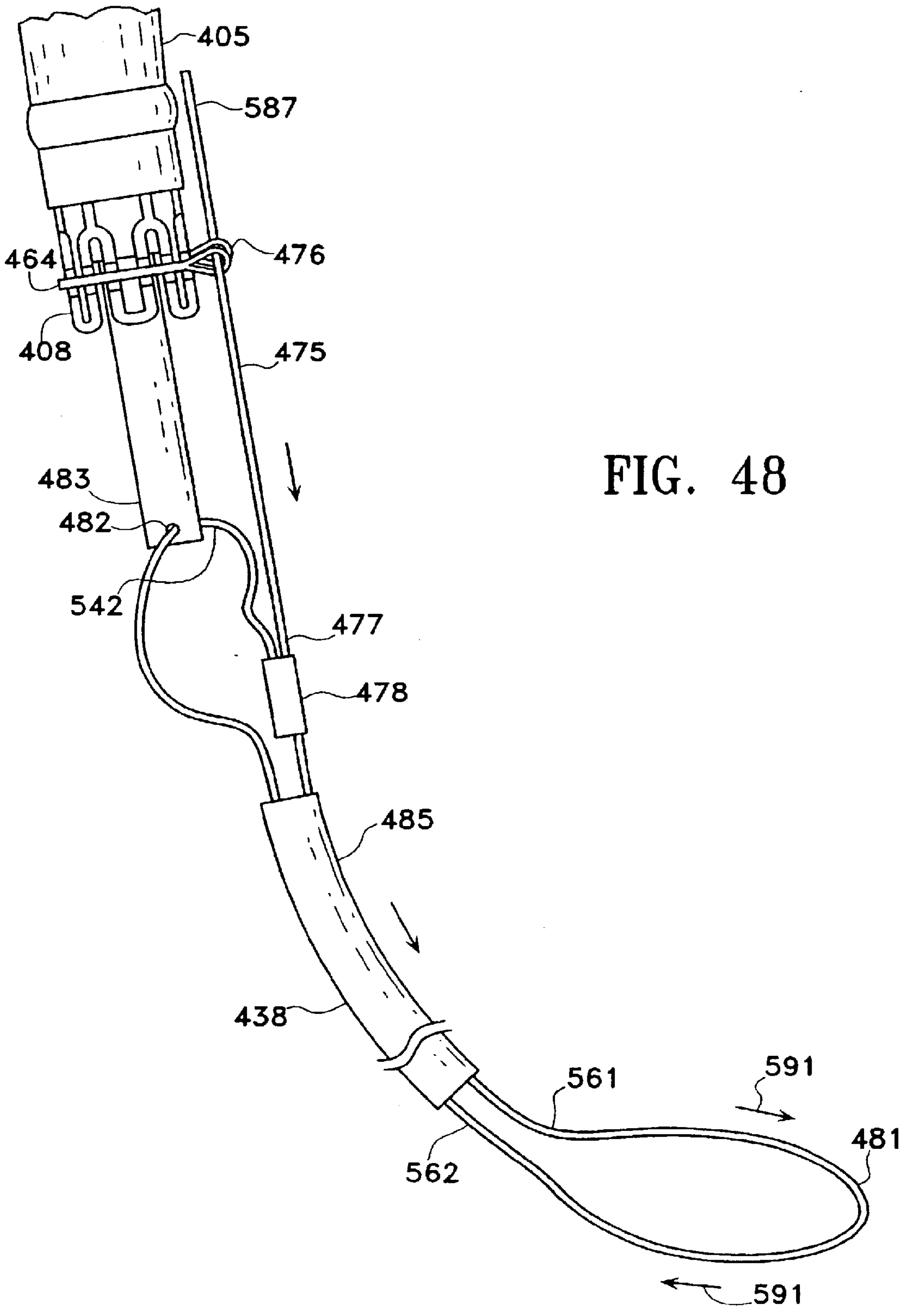

FIG. 48 depicts an enlarged view of the proximal end 483 of the secondary belt support member 454. The proximal self-expanding member 408 of the contralateral leg 405 is secured to the proximal end 417 of the contralateral leg 405. The proximal self-expanding member 408 is constrained in a radial direction by the secondary belt 464, which has end loops 476 releasably constrained by the distal end 587 of the secondary release wire 475. The proximal end 477 of the secondary release wire 475 terminates with and is secured to the actuator hub 478. The release strand is secured to the actuator hub 478 and loops through an aperture or hole 482 in the proximal end 483 of the secondary belt support member 454. As discussed above, a portion of the release strand 481 is disposed within the release strand tube 485 to form the secondary release cable 438.

When both a first length 561 and second length 562 of the release strand 481 are pulled together in a proximal direction from a proximal end 588 of the secondary release cable 438, the entire pulling force is exerted on the proximal end 483 of the secondary belt support member 454 because the looped distal end 542 of the release strand 481 pulls on the proximal end 483 of the secondary belt support member 454 without displacing the actuator hub 478.

Figure 49:
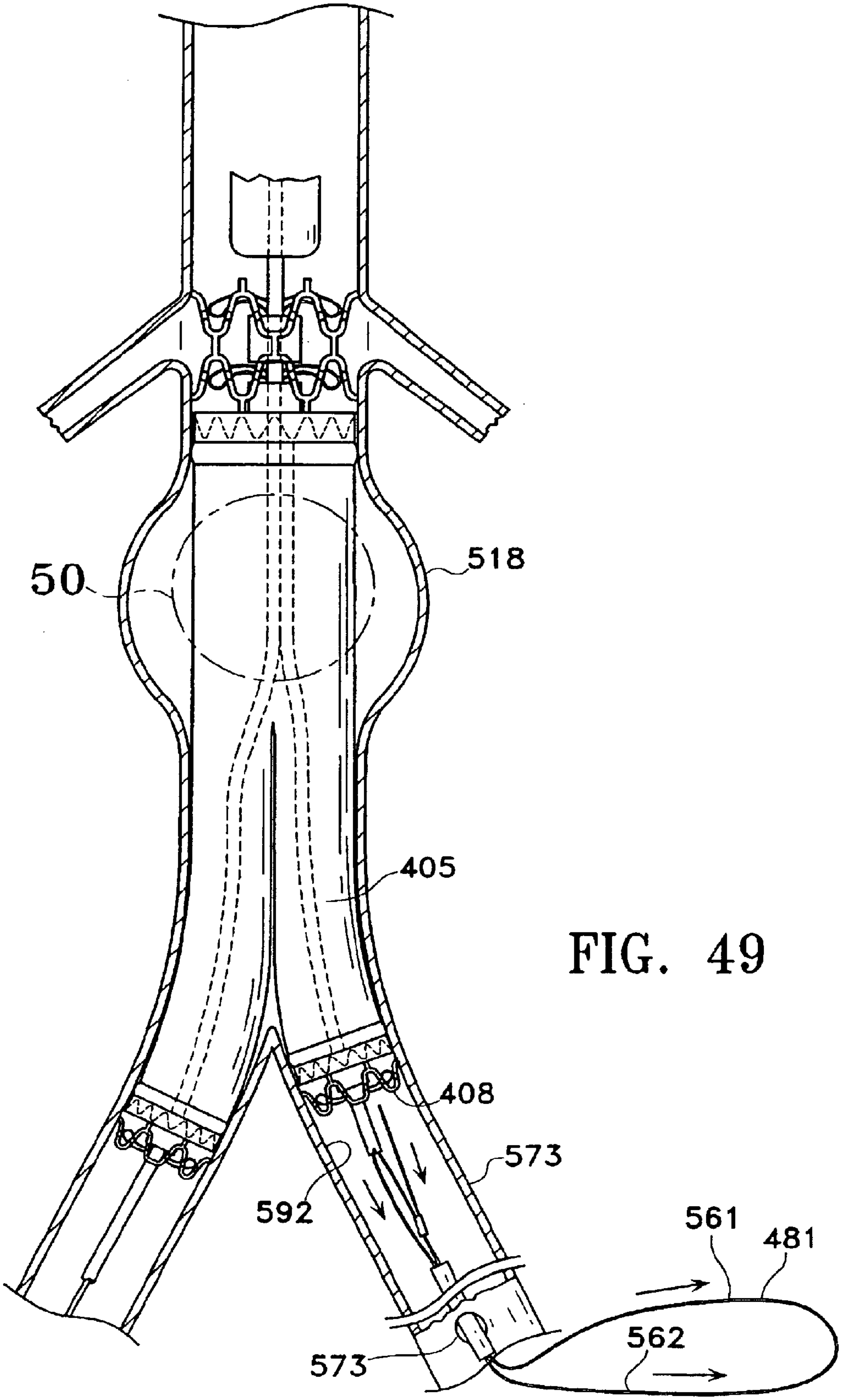
Figure 50:
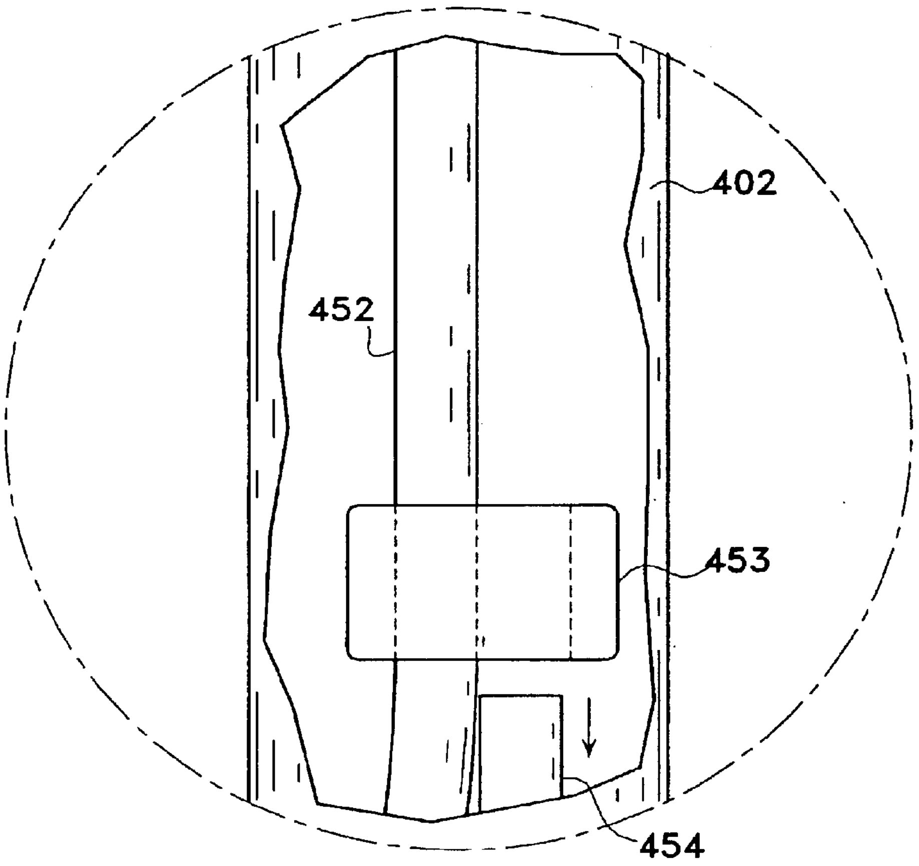

When deployment of the proximal self-expanding member 408 of the contralateral leg 405 is desired, the operator applies tension in a proximal direction only to the first length 561 of the release strand 481, which extends proximally from the actuator hub 478. The direction of such tension is indicated in FIG. 48 by the arrows 591. Upon the application of this proximal tension, the actuator hub 478 is moved proximally, as is the secondary release wire 475 which is secured to the actuator hub 478. The proximal self-expanding member 408 of the contralateral leg 405 deploys when the distal end 587 of the secondary release wire 475 passes through the end loops 468 of the secondary belt 464 so as to release the radial constraint on the proximal self-expanding member 408 imposed by the secondary belt 464. Upon release of the radial constraint, the proximal selfexpanding member 408 expands so as to contact an inside surface 592 of the left iliac artery 573 as shown in FIG. 49. Once the proximal self-expanding member 408 of the contralateral leg 405 is expanded, the operator may then apply tension to both lengths 561 and 562 of the release strand 481 to withdraw the secondary belt support member 454 from the housing 453 (as shown in FIG. 50) and remove it from the patient's vasculature through the left femoral artery access hole 537.

Figure 51:
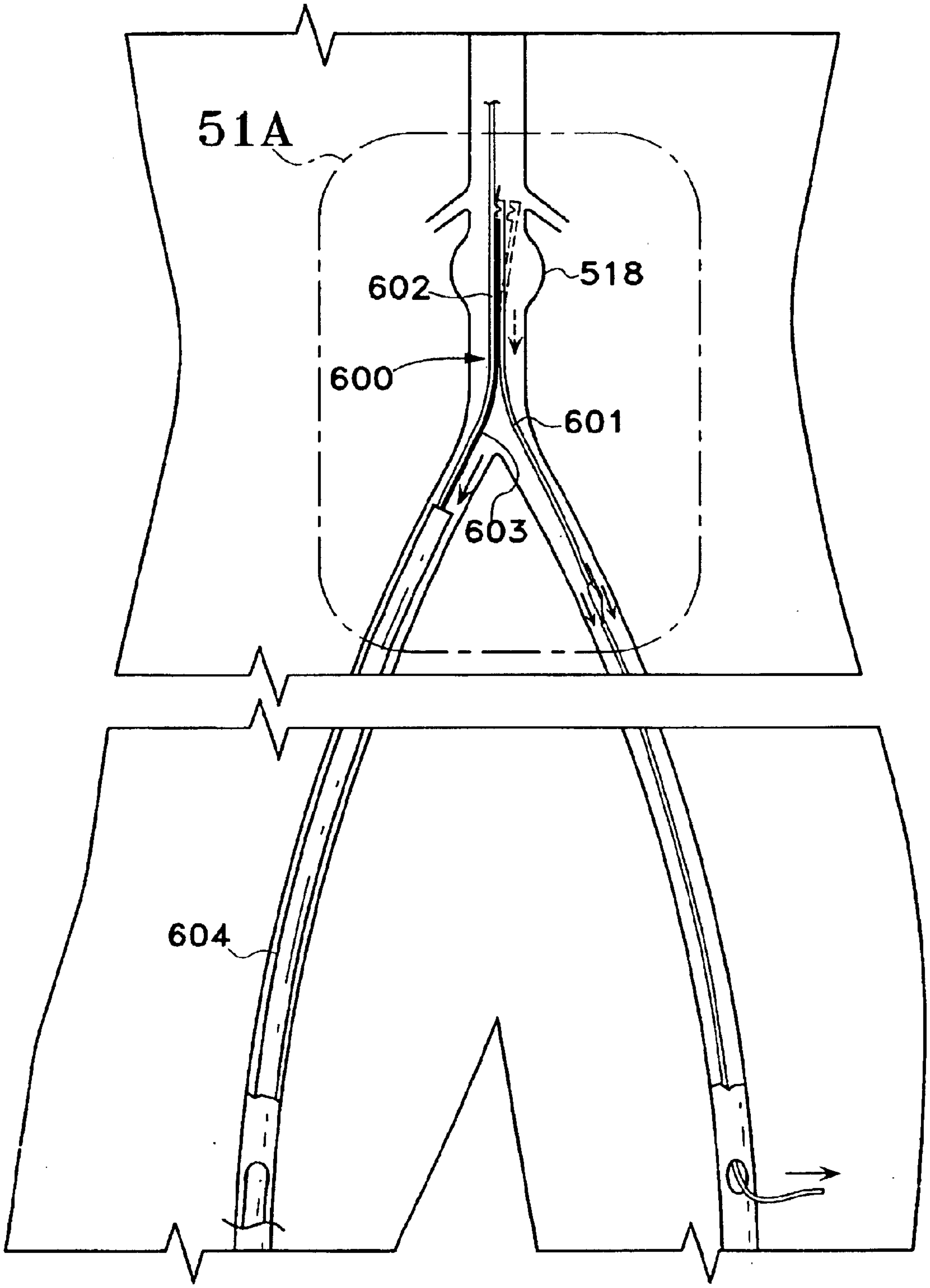
Figure 51A:
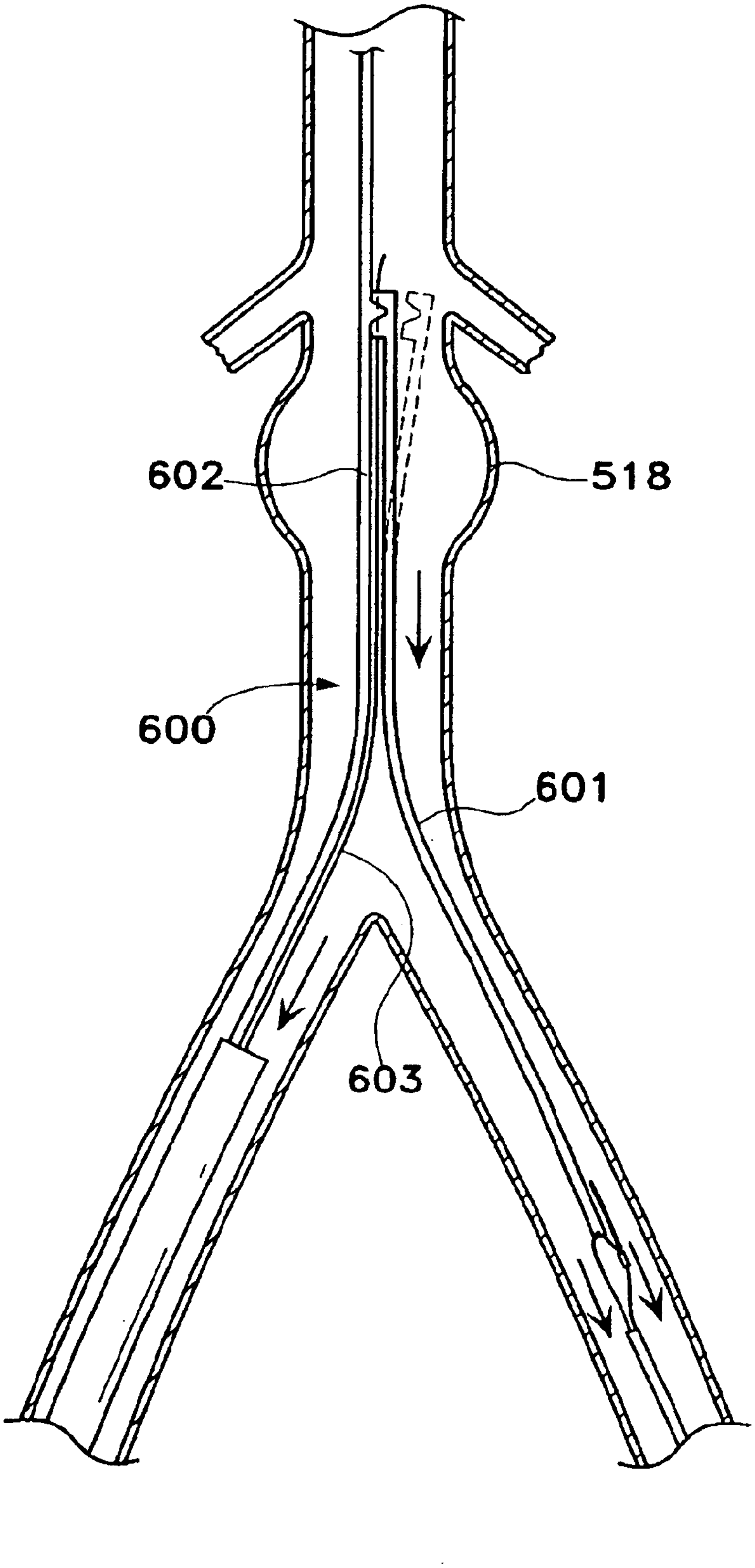

FIG. 51 depicts an alternative embodiment of a belt support member assembly 600 in which the secondary belt support member 601 is detached from the primary belt support member 602 by withdrawal of a latch wire 603. Generally, all other features of the delivery system 604 of the embodiment of FIG. 51 can be the same as the delivery systems discussed above. It should be noted, however, that the embodiment shown in FIG. 51 does not allow the secondary belt support member 601 to slide in an axial direction relative to the primary belt support member 602. As such, it may be desirable to use this embodiment to deliver and deploy a graft having legs that are not substantially equal in length. Otherwise, if proximal self-expanding members are to be axially offset, the secondary belt support member 601 would have to be detached from the primary belt support member 602 prior to deploying and releasing the secondary belt (not shown).

Figure 52:
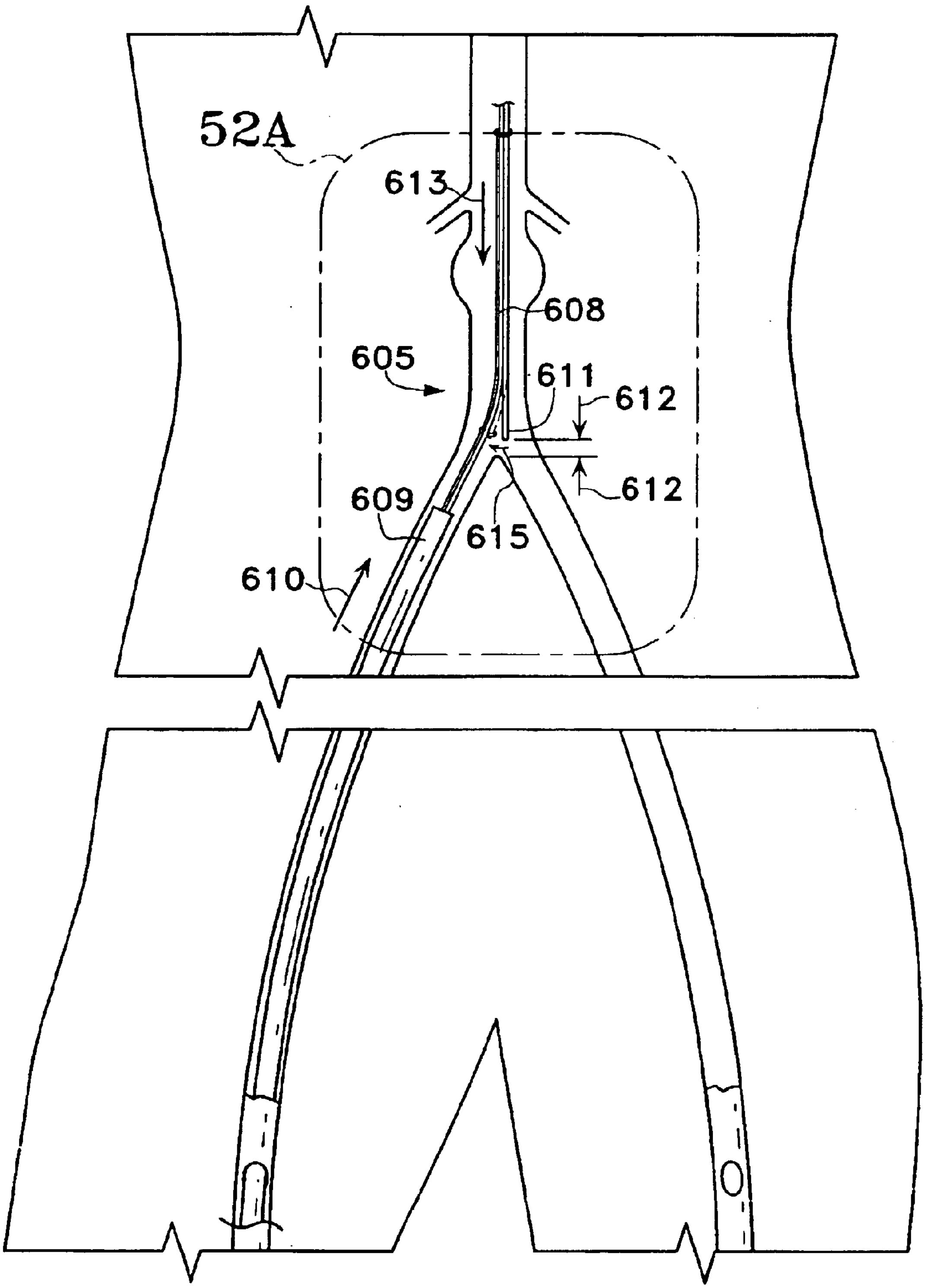
Figure 52A:
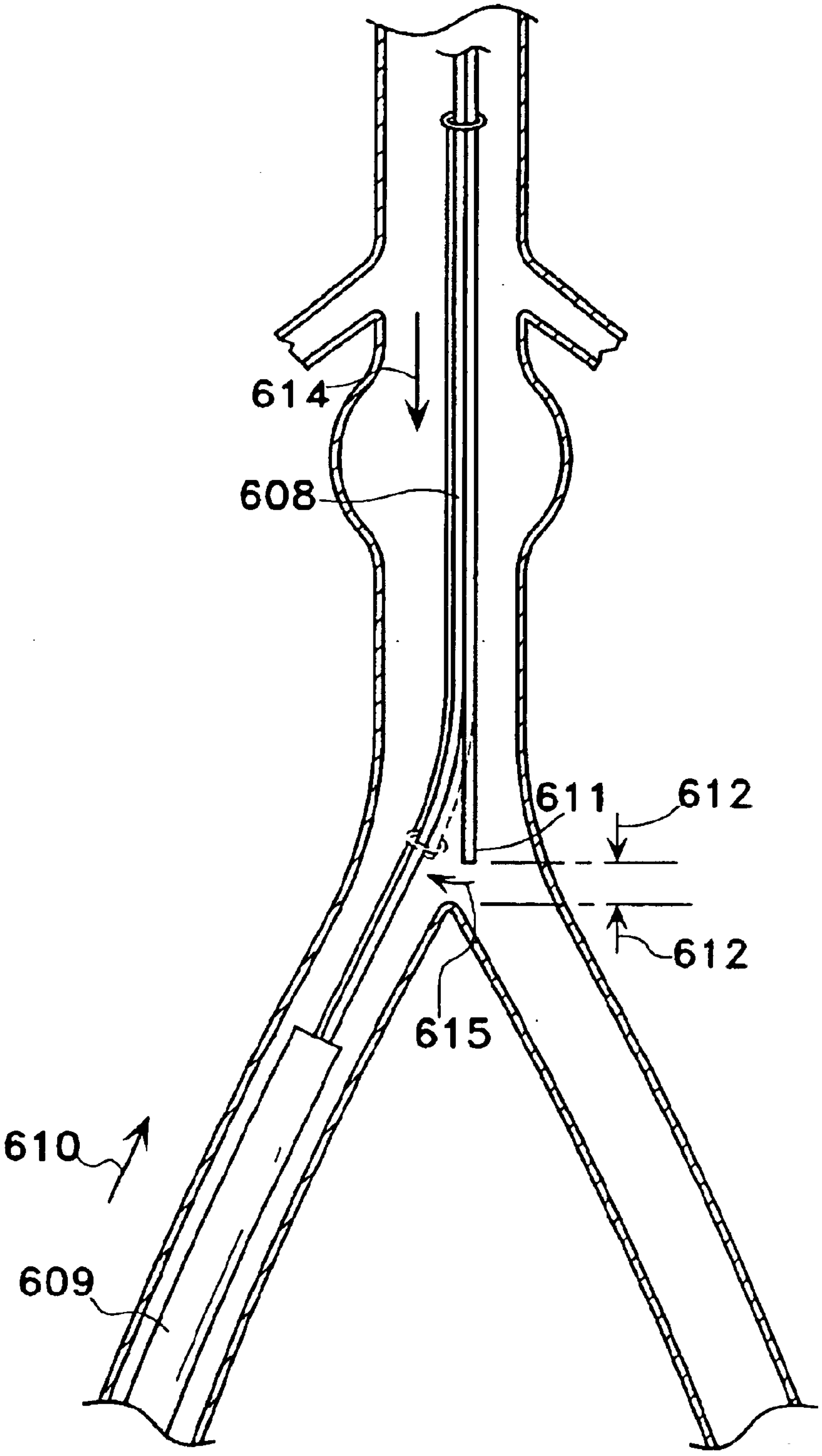

FIG. 52 shows an alternative belt support member assembly 605 wherein the secondary belt support member 607 is laterally displaced and locked into a position parallel with the primary belt support member 608 prior to removal of the delivery system 609 from the patient's vasculature. All other features of the delivery system 609 of the embodiment of FIG. 52 can be the same as the delivery systems discussed above. In use, after all self-expanding members have been deployed, the delivery system 609 is advanced distally into the patient's vasculature, as shown by the arrow 610 in FIG. 52, in order to achieve a gap between a proximal end 611 of the secondary belt support member 607 and the patient's vasculature as shown by the arrows 612 in FIG. 52. A constraining ring 613 is then retracted proximally, as indicated by the arrow 614, so as to force the secondary belt support member 607 to be laterally displaced as shown by the arrow 615, also in FIG. 52. Once the secondary belt support member 607 has been fully retracted in a lateral direction so as to be substantially parallel to the primary belt support member 608, the delivery system 609 can then be retracted from the patient's vasculature.

As previously described with respect to the tubular graft embodiment 11, thereafter, the bifurcated graft 401 may be inflated with an inflation material (not shown) via the inflation tube 444 and inflation port 421 until the inflatable channels 418 and inflatable cuffs 413, 414 and 415 have been filled to a sufficient level to meet sealing and other structural requirements necessary for the bifurcated graft main body portion 402 and the ipsilateral and contralateral legs 407 and 408 to meet clinical performance criteria.

For all the embodiments described, both tubular and bifurcated, inflation is generally accomplished by inserting or injecting, via one or more device such as a syringe or other suitable mechanism, the inflation material under a pressure- or volume-control environment.

For instance, in one embodiment of a pressure-control technique, a volume of inflation material is first injected into the delivery system 400 (which at this point may include the graft, but may also include the inflation tube 444). The particular desired volume of inflation material will depend on several factors, including, e.g., the composition and nature of the inflation and polymer graft material, the size of the graft 401 to be deployed, the vessel or lumen diameter into which the graft 401 is deployed, the configuration of the graft 401 (tubular, bifurcated, etc.), the features of the graft main body 402 and (if present) legs 407 and 408, and the conditions during the procedure (such as temperature).

Thereafter, the operator may affix a pressure control device, such as an Endoflator® or the like, to the injection port 621 of the proximal adapter 427 of the inflation tube and apply a pressure to the delivery system 400 and a graft 401 for a period of time. This serves to ensure that the fill material previously introduced enters the graft 401 and fills it to the desired pressure level.

We have found that a useful pressure-control approach involves a series of such constant pressure applications, each for a period of time. For instance, the graft 401 may first be pressurized at a level from about 5 psi to about 12 psi or higher, preferably about 9 psi, for between about 5 seconds and 5 minutes, preferably about 3 minutes or more. Optional monitoring of the fluid and the device during the fill procedure may be used to help ensure a proper fill. Such monitoring may be accomplished under fluoroscopy or other technique, for instance, if the fill material is radiopaque.

Thereafter, the fill protocol may be completed, or the pressure may be increased to between about 10 psi and about 15 psi or higher, preferably about 12 psi, for an additional period of time ranging from between about 5 seconds and 5 minutes or more, preferably about 1 minute. If the graft 401 so requires, the pressure may be increased one or more additional times in the same fashion to effect the proper fill. For instance, subsequent pressure may be applied between about 12 and 20 psi or more, preferably about 16 psi to 18 psi, for the time required to satisfy the operator that the graft 401 is sufficiently filled.

The details of particular pressure-time profiles, as well as whether a single pressure-time application or a series of such applications is used to fill embodiments of the graft 401 will depend on the factors described above with respect to the volume of fill material used; the properties and composition of the fill material tend to be of significance in optimizing the fill protocol. For example, a stepped series of pressure-time profiles as described above is useful when the fill material comprises a hardenable or curable material whose physical properties may be time-dependent and which change after being introduced into the graft 401 and its delivery system 400.

Alternatively, a volume-control method may be utilized to fill embodiments of the grafts 11 and 401, including both tubular and bifurcated. Here, a volume of fill material is again introduced into the delivery system 400 as described above. In this method, however, the volume of fill material used is precisely enough material to fill the graft 401, the inflation tube 444, and any other component in the delivery system 400 through which the fill fluid may travel on its way to the graft 401. The operator introduces the predetermined quantity of fill material, preferably with a syringe or similar mechanism, into the inflation tube 444 and graft 401. A precise amount of fill material may be measured into a syringe, for example, so that when the syringe is emptied into the delivery system 400 and graft 401, the exact desired amount of fill material has reached the graft 401. After a period of time (which period will depend on the factors previously discussed), the syringe or equivalent may be removed from the inflation tube 444 or injection port 621 of proximal adapter 427 and the procedure completed.

A pressurized cartridge of gas or other fluid may be used in lieu of a syringe to introduce the fill material into the delivery system and graft under this volume-control regime so to provide a consistent and reliable force for moving the fill material into the graft 401. This minimizes the chance that variations in the force and rate of fill material introduction via a syringe-based technique affect the fill protocol and possibly the clinical efficacy of the graft 401 itself.

For each of the pressure- and volume-control configurations, an optional pressure relief system may be included so to bleed any air or other fluid existing in the delivery system 400 prior to the introduction of the fill material (such as the inflation tube 444 or graft 401) so to avoid introducing such fluid into the patient. Such an optional system may, for example, comprise a pressure relief valve at the graft 401/inflation tube 444 interface and a pressure relief tube disposed through the delivery system 400 (e.g., adjacent the inflation tube 444) terminating at the proximal adapter 427 and vented to the atmosphere.

Figure 53:
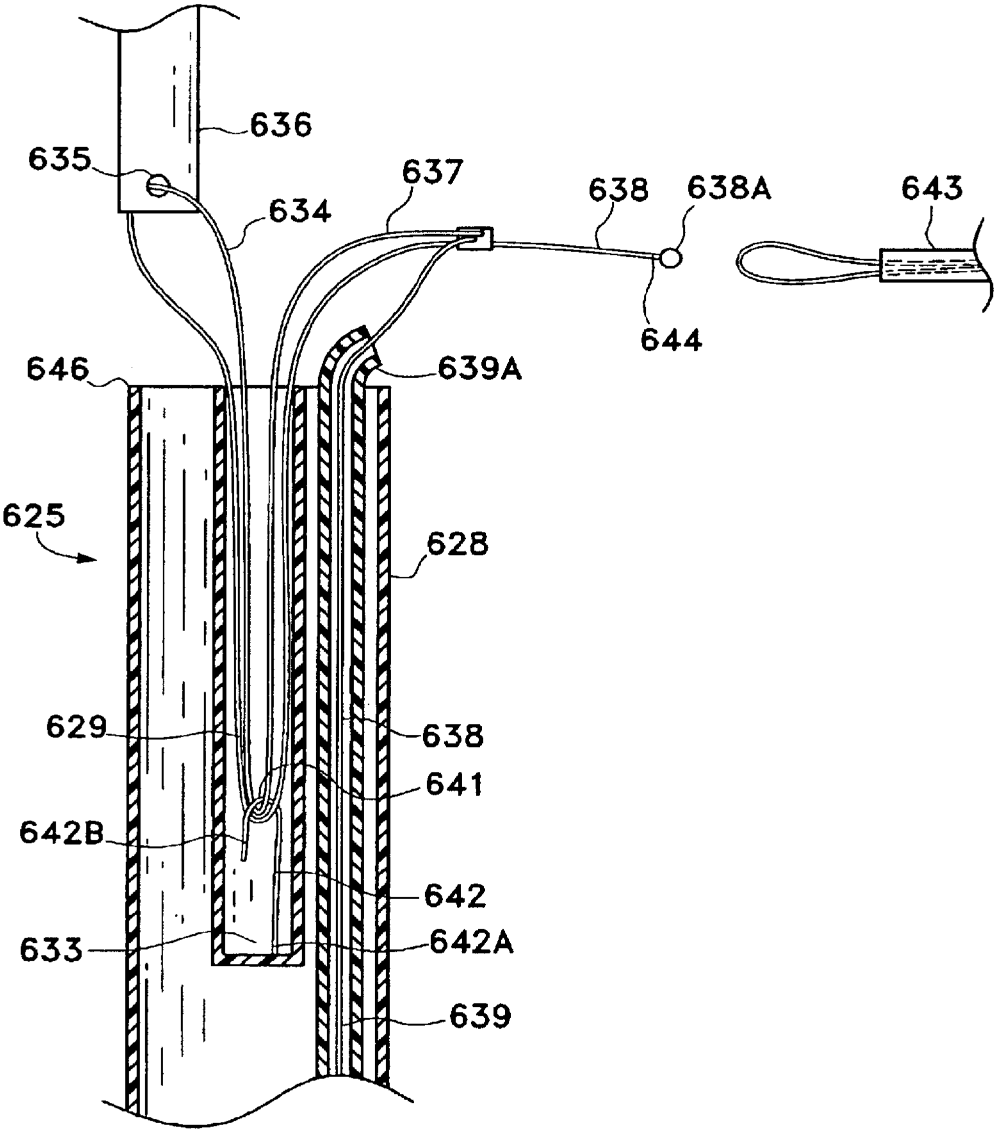
FIGS. 53–57 illustrate a number of alternative catheter distal shaft arrangements in which a well is provided to facilitate the orderly and tangle-free withdrawal of the release strand from the delivery catheter.

Turning now to FIG. 53, an embodiment of a bifurcated graft delivery system 625 and method is illustrated. This embodiment is tailored to provide for a controlled withdrawal of a secondary release cable from a lumen of an inner tubular member 628 so to help eliminate the possibility that the release cable 626 becomes entangled or otherwise twisted during deployment.

Shown in FIG. 53 is a well 633 is disposed in the inner tubular member 628. Well 633 contains a release strand 629 that is looped at its proximal end 634 outside the well 633 through an aperture 635 in the secondary belt support member 636 and that is affixed or attached at its distal end 637 to a second guidewire 638. The second guidewire 638 is shown in the embodiment of FIG. 53 as disposed in its own optional lumen 639 within the inner tubular member 628.

Within the well 633, the release strand 629 is arranged to form a "u-turn" in which it changes direction to double back on itself at juncture 641 as shown in FIG. 53. At juncture 641, a friction line 642 is looped around all or a portion of the release strand 629. This friction line 642 is fixed to the bottom of the well 633 on one end 642A and is free on another end 642B. The friction line 642 is preferably a polymeric monofilament such as polyimide, etc., but may be metallic and may be braided as necessary to achieve the desired friction characteristic needed to interact with release strand 629. Friction line 642 has a length sufficient to interact with the release strand 629 during the deployment process until the release strand 629 has been completely removed from the well 633 as will now be described in detail.

In use, the configuration of FIG. 53 works as follows. Once the left and right femoral access holes 531 and 537, discussed above, have been created, the delivery system 625 is introduced into and through the patient's vasculature. A snare catheter 643 is introduced into the left femoral artery access hole, such as the left femoral artery access hole 537 discussed above. The operator then captures the tip 644 of the second guidewire 638 with the snare 643. In the embodiment of FIG. 53, the second guidewire 638 is shown as pre-attached to the release strand 629 at the distal end 637.

A ball capture tip 638A or similar member may optionally be disposed on the tip 644 of second guidewire 638 to facilitate its capture by snare catheter 643 and prevent possible injury to the vessel intima. In addition, tip 638A may be made radiopaque so that it may be readily located by the operator during the procedure. When in the form of a ball, tip 638A may have a diameter ranging from between about 0.020 inch to about 0.120 inch, specifically, between about 0.040 inch to about 0.060 inch. Although not shown in the figures, second guidewire 638 may also have one or more additional sections branching therefrom, each having a tip or member similar to tip 644, including tip 638A, so to provide the operator with one or more alternative sites for capture with snare 643 in case tip 638A is inaccessible.

Figure 54:
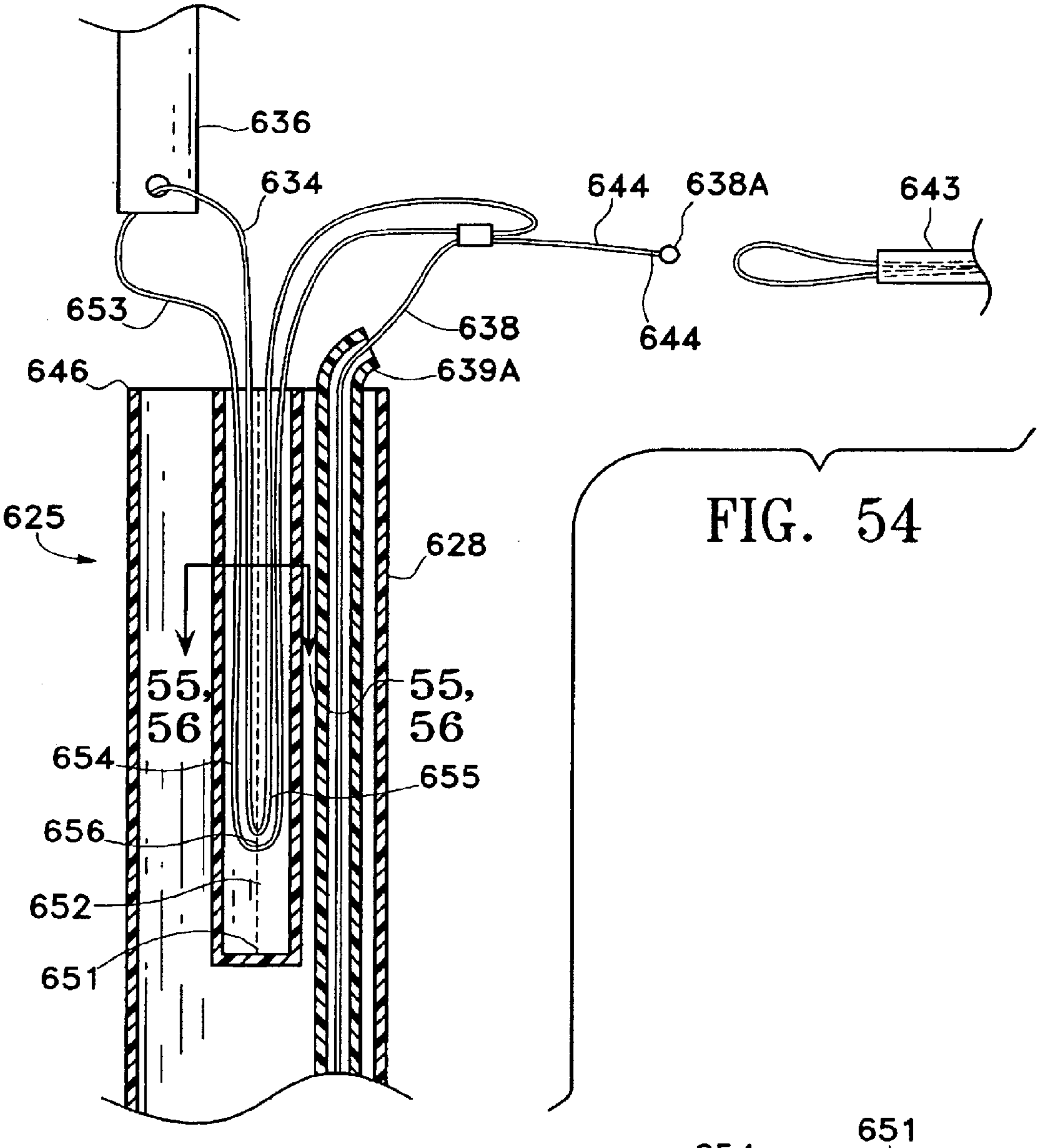

An angled extension 639A may optionally be provided on one or both of the top of optional lumen 639 and/or the top of well 633. Angled extension 639A may be made of any suitable polymeric or metallic material such as stainless steel. As seen in FIGS. 53–54, extension 639A disposed on the top of lumen 639 is generally biased towards the artery in which snare 643 is disposed at an angle of between about 20 degrees and about 120 degrees, specifically, between about 40 degrees and about 95 degrees, so to guide the release strand 629 and 653 in the proper direction and thus facilitate ease of capture by snare 643.

As the second guidewire 638 is pulled out of the inner tubular member 628 from the left femoral artery access hole 537 in the direction shown by the arrow 544 in FIG. 37, the release strand 629 feeds out of the well 633 in an orderly and linear fashion in a direction from the release strand distal end 637 to its proximal end 634. This is made possible by the forces created at the "u-turn" or juncture 641 by the physical interface with the friction line 642. The friction force (which can be tailored by the proper combination of release strand 629 and friction line 642 diameters and their materials and by properly dimensioning of the well 633, for example) provides enough resistance to counter the force applied by the operator so that the "u-turn" or juncture 641 moves in an orderly fashion in a direction from the well bottom 633 to the distal end 646 of the inner tubular member 628 until it exits out of the outer tubular member 628. At this point, any remaining friction line 642 at the juncture 641 is superfluous as it has served its purpose of facilitating an orderly withdrawal of the release strand 629. The operator continues to pull on the second guidewire 638 as previously described so that the release strand 629 extends through the left femoral artery access port 537. We have found the embodiment of FIG. 53 to be useful in achieving an orderly and tangle-free deployment.

Figure 55:
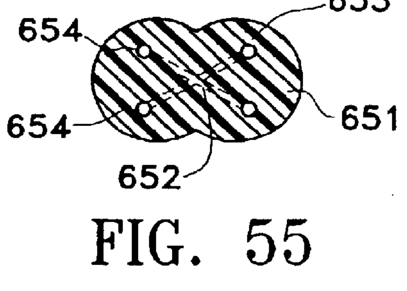
Figure 56:
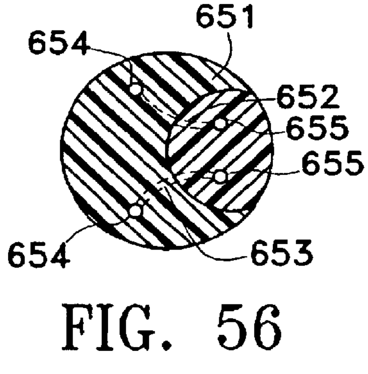

Alternatively, any number of other arrangements in which the release strand 629 may be fed out of the outer tubular member 628 in an orderly manner is within the scope of the present invention. For instance, the well 651 shown in FIGS. 54–56 is, for instance, an extruded polymeric part having a unique cross-sectional configuration that eliminates the need for the friction line 642 in the embodiment shown in FIG. 53. Here, a narrowing constraint or gap 652 runs the length of the well interior 651, forming a physical barrier between first and second opposing portions 654 and 655 of the release strand 653, shown in FIGS. 54–56. The constraint or gap 652 is sized to allow the passage therethrough of the release strand juncture or "u-turn" 656. As the operator pulls the release strand 653 out of the well 651, the constraint or gap 652 prevents the opposing portions 654 and 655 of the release strand 653 from crossing into the other side of the well 651. Said another way, the constraint or gap 652 keeps the juncture or "u-turn" 656 within its vicinity to facilitate an orderly withdrawal of the release strand 653 from the well 651. In this embodiment, the release strand 653 can have a diameter of between about 0.004 and 0.010 inch; specifically between about 0.006 and 0.007 inch. The gap or constraint 652 should be between about 0.003 and about 0.009 inch; preferably between about 0.005 and about 0.006 inch.

Figure 57:
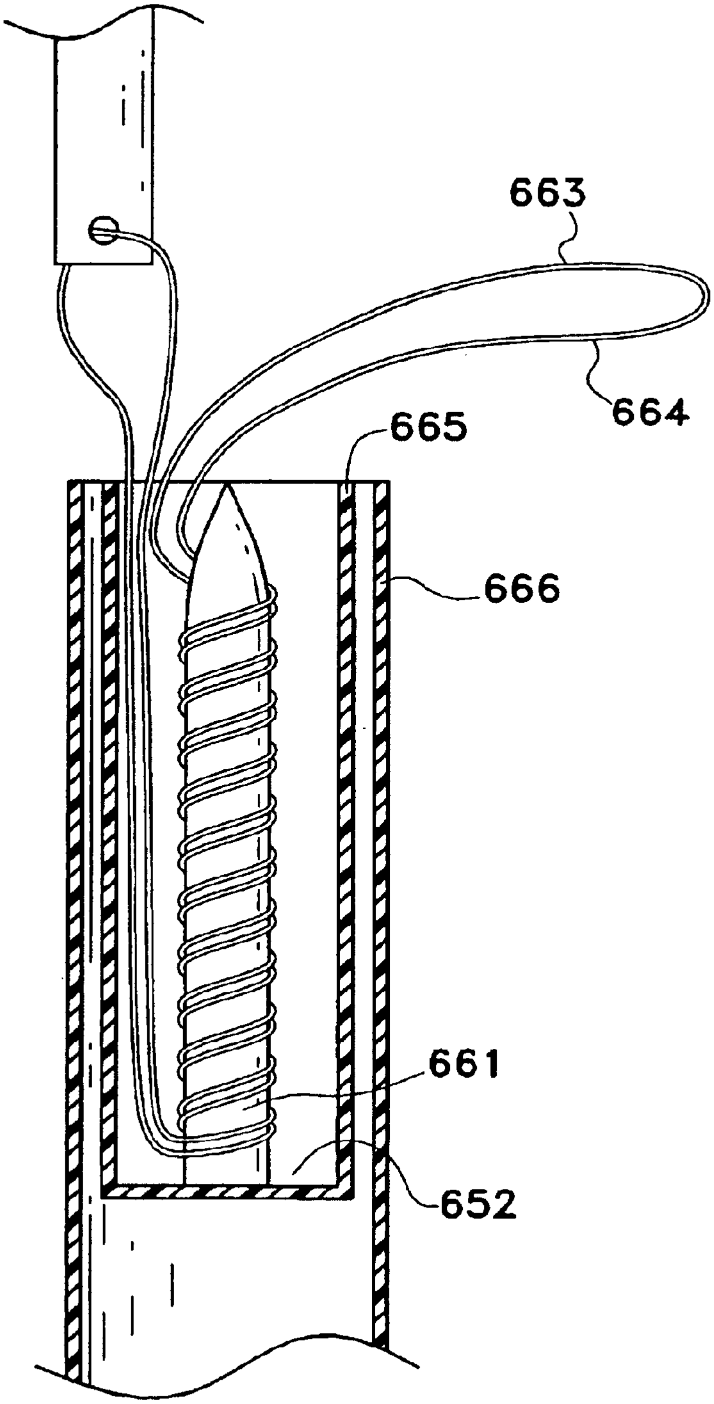

Yet another variation of this embodiment, shown in FIG. 57, includes a post 661 disposed in a well 652 around which the release strand 663 is wound such that as the operator pulls the distal portion 664 of the release strand 663 out of the distal end 665 of the well 652, the release strand 663 unwinds in an orderly fashion from the post 661. The post 661 may be optionally configured to spin on its longitudinal axis, similar to that of a fishing reel spinner, to facilitate the exit of the release strand 663.

Other variations, such as a block and tackle arrangement (not shown), are envisioned in which the release strand 663 is looped through a grommet or similar feature. The grommet provides the necessary friction to prevent the entire release strand 663 from pulling out of the well 652 in one mass as soon as the operator applies a force on a distal end thereof. Any arrangement in which a frictional or similar force is utilized to allow for the orderly dispensation of the release strand 663 from the shaft or post 661 is within the scope of the embodiment contemplated.

While particular forms of the invention have been illustrated and described, it will be apparent that various modifications can be made without departing from the spirit and scope of the invention. Accordingly, it is not intended that the invention be so limited.

We claim the following:

1. A delivery system for a bifurcated intracorporeal device comprising:

an elongate shaft having a proximal section and a distal section with the distal section comprising:

an elongate primary belt support member that is configured to be disposed within at least a portion of the bifurcated intracorporeal device;

at least one primary belt secured to the primary belt support member configured to be circumferentially disposed about the bifurcated intracorporeal device so to at least partially constrain the device;

a primary release member configured to engage and releasably secure the primary belt in a constraining configuration;

at least one elongate secondary belt support member disposed adjacent the elongate primary belt support member;

at least one secondary belt secured to the secondary belt support member and configured to be circumferentially disposed about the bifurcated intracorporeal device so to at least partially constrain the device; and a secondary release member configured to engage and releasably secure the secondary belt in a constraining configuration.

2. The delivery system of claim 1 wherein the primary belt support member is an elongate tubular member and the bifurcated intracorporeal device is a bifurcated endovascular graft in a constrained state.

3. The delivery system of claim 1 wherein the primary belt and the secondary belt each comprises a length of wire having a first end and a second end, with each of said first and second wire ends secured to the primary belt support members and secondary belt support member, respectively.

4. The delivery system of claim 3 wherein the wire comprises nickel titanium.

5. The delivery system of claim 1 wherein one or both of the primary belt and the secondary belt comprises first and second opposed ends and wherein the first opposed end has a different cross-sectional area than the second opposed end.

6. The delivery system of claim 5 wherein each of the first and second opposed ends forms an end loop.

7. The delivery system of claim 1 wherein the release members comprise release wires moveably disposed within opposed looped ends of the respective belts.

8. The delivery system of claim 1 wherein the belts in the constraining configuration form a planes that are substantially orthogonal to a longitudinal axis of the elongate shaft.

9. The delivery system of claim 1 wherein at least two belts are configured to be releasable by a single release member.

10. The delivery system of claim 1 comprising a plurality of primary release members wherein the proximal ends of at least two of the primary release members are color-coded.

11. The delivery system of claim 1 wherein the at least one primary belt comprises a plurality of primary belts and wherein the primary release member comprises a plurality of primary release members that releasably secure the plurality of primary belts, wherein proximal ends of the primary release members are in a linear spatial configuration at a proximal end of the delivery system that corresponds to a desired deployment sequence for the plurality of belts.

12. The delivery system of claim 11 wherein the plurality of primary release members comprise a distal primary release wire handle and a proximal primary release wire handle disposed in a nested configuration.

13. The delivery system of claim 1 wherein the primary release member comprises a branched release wire.

14. The delivery system of claim 1 further comprising a secondary belt support member housing secured to the primary belt support member wherein the secondary belt support member is configured to move axially within the housing and the housing and secondary belt support member are configured to prevent relative rotational movement therebetween.

15. A delivery system for a bifurcated graft comprising:

an elongate shaft having a proximal section and a distal section with the distal section comprising:

a portion having disposed thereon the bifurcated graft, the graft having a main body portion, an ipsilateral leg and a contralateral leg;

an elongate primary belt support member disposed adjacent the main body portion and the ipsilateral leg;

at least one primary belt secured to the primary belt support member and releasably disposed about a circumference of the bifurcated graft and which constrains at least a portion of the graft;

a primary release member which releasably secures the primary belt in the constraining configuration;

at least one secondary belt support member disposed adjacent the contralateral leg;

at least one secondary belt secured to the secondary belt support member and circumferentially disposed about the bifurcated graft and which constrains at least a portion of the graft; and a secondary release member which releasably secures the secondary belt in the constraining configuration.

16. The delivery system of claim 15 additionally comprising a first proximal self-expanding member secured to a proximal end of the contralateral leg and a second proximal self-expanding member secured to a proximal end of the ipsilateral leg, and wherein the legs have a different length and the first and second proximal self-expanding members are axially offset from each other when the graft is in a constrained state within the delivery system.

17. The delivery system of claim 15 additionally comprising a first proximal self-expanding member secured to a proximal end of the contralateral leg and a second proximal self-expanding member secured to a proximal end of the ipsilateral leg and wherein the legs have substantially the same length and one of the legs is axially compressed or folded such that the first and second proximal self-expanding members are axially offset from each other when the graft is in a restrained state within the delivery system.

18. The delivery system of claim 15 wherein the primary belt constrains a distal self-expanding member disposed at a distal end of the bifurcated graft main body portion.

19. The delivery system of claim 18 wherein the distal self-expanding member is a tubular stent.

20. The delivery system of claim 19 wherein the stent comprises a circumferential groove configured to accept at least a portion of the primary belt.

21. The delivery system of claim 15 wherein the primary belt and the secondary belt each comprises at least one length of wire having a first end and a second end and configured in a loop with each of said first and second wire ends secured to the primary belt support member and the secondary belt support member, respectively.

22. The delivery system of claim 21 wherein the wire comprises nickel titanium.

23. The delivery system of claim 15 wherein the primary belt and secondary belt comprise at least one length of wire having opposed end loops having differing diameters.

24. The delivery system of claim 15 wherein the release members comprise release wires moveably disposed within opposed looped ends of their respective belts.

25. The delivery system of claim 15 wherein the belts in the constraining configuration form planes that are substantially orthogonal to a longitudinal axis of the elongate shaft.

26. The delivery system of claim 15 wherein at least two primary belts are configured to be releasable by the same release member.

27. The delivery system of claim 15 wherein the primary belt support member comprises a guidewire tube.

28. The delivery system of claim 15 wherein the distal section further comprises an outer protective sheath disposed about the bifurcated graft while the bifurcated graft is in a constrained state.

29. A delivery system for a bifurcated graft having a main body portion, an ipsilateral leg, contralateral leg and a plurality of self-expanding members secured to the graft, comprising:

an elongate shaft having a proximal section and a distal section with the distal section of the elongate shaft comprising:

a portion configured to have disposed thereon the bifurcated graft;

a guidewire tube disposed within the main body portion and ipsilateral leg of the bifurcated graft;

a plurality of primary belts secured to the guidewire tube, the plurality of belts being adjacent the self-expanding members of the graft, the belts being circumferentially disposed about adjacent self-expanding members in a configuration that at least partially constrains the respective self-expanding members;

a primary release wire that engages and releasably secures at least one of the primary belts in a constraining configuration;

a secondary belt support member disposed within the contralateral leg of the bifurcated graft;

a secondary belt secured to the secondary belt support member adjacent self-expanding members of the graft, the belt being circumferentially disposed about an adjacent self-expanding member in a configuration that at least partially constrains the adjacent self-expanding member; and a secondary release wire that engages and releasably secures the secondary belt in a constraining configuration.

30. A delivery system for a bifurcated intracorporeal device comprising:

an elongate shaft means having a proximal section and a distal section with the distal section comprising:

an elongate primary constraint support means;

at least one primary constraint means secured to the primary constraint support means configured to be releasably disposed about a circumference of the bifurcated intracorporeal device so to at least partially constrain the device;

a primary release means configured to engage and releasably secure the primary constraint means in a constraining configuration;

at least one elongate secondary constraint support member disposed adjacent the elongate primary constraint support means;

at least one secondary constraint means secured to the secondary constraint support means configured to be circumferentially disposed about a bifurcated intracorporeal device so to at least partially constrain the device; and a secondary release means configured to engage and releasably secure the secondary constraint means in a constraining configuration.

31. The delivery system of claim 30 wherein the primary constraint support means is an elongate tubular means and the bifurcated intracorporeal device is a bifurcated graft in a constrained state.

32. The delivery system of claim 30 wherein one or both of the primary constraint means and the secondary constraint means comprises first and second opposed ends and wherein the first opposed end has a different cross-sectional area than the second opposed end.

33. The delivery system of claim 30 wherein the constraint means in the constraining configuration form planes that are substantially orthogonal to a longitudinal axis of the elongate shaft means.

34. The delivery system of claim 30 wherein at least two of the constraint means are configured to be releasable by a single release means.

35. The delivery system of claim 30 comprising a plurality of primary release means wherein the proximal ends of at least two of the primary release means are color-coded.

36. The delivery system of claim 30 wherein the at least one primary release means comprises a plurality of primary release means and the at least one primary constraint means comprises a plurality of constraint means, wherein proximal ends of the plurality of primary release means are in a linear spatial configuration that corresponds to a desired deployment sequence for the plurality of constraint means.

37. A delivery system for a bifurcated graft comprising:

an elongate shaft means having a proximal section and a distal section with the distal section comprising:

a portion having disposed thereon the bifurcated graft, the graft having a main body portion, an ipsilateral leg and a contralateral leg;

an elongate primary constraint support means disposed within the main body portion and ipsilateral leg;

at least one primary constraint means secured to the primary constraint support means and circumferentially disposed about the bifurcated graft and which constrains at least a portion of the graft;

a primary release means which releasably secures the primary constraint means in the constraining configuration;

at least one secondary constraint support means disposed adjacent the contralateral leg;

at least one secondary constraint means secured to the secondary constraint support means and circumferentially disposed about the bifurcated graft and which constrains at least a portion of the graft; and a secondary release means which releasably secures the secondary constraint means in the constraining configuration.

38. The delivery system of claim 37 wherein the primary constraint means constrains a distal self-expanding member disposed at a distal end of the bifurcated graft main body portion.

39. The delivery system of claim 37 wherein the constraint means in the constraining configuration form planes that are substantially orthogonal to a longitudinal axis of the elongate shaft means.

40. A delivery system for a bifurcated graft having a main body portion, an ipsilateral leg, contralateral leg and a plurality of self-expanding members secured to the graft, comprising:

an elongate shaft means having a proximal section and a distal section with the distal section of the elongate shaft comprising:

a portion configured to have disposed thereon the bifurcated graft;

a guidewire tube means disposed within the main body portion and ipsilateral leg of the bifurcated graft;

a plurality of primary constraint means secured to the guidewire tube means and adjacent respective self-expanding members of the graft, the primary constraint means being circumferentially disposed about the adjacent self-expanding members in a configuration that at least partially constrains the respective self-expanding members;

a primary release means that engages and releasably secures at least one of the primary constraint means in a constraining configuration;

a secondary constraint support means disposed within the contralateral leg of the bifurcated graft;

a secondary constraint means secured to the secondary constraint support means adjacent respective self-expanding members of the graft, the secondary constraint means being circumferentially disposed about the adjacent self-expanding members in a configuration that at least partially constrains the adjacent self-expanding members; and a secondary release means that engages and releasably secures the secondary constraint means in a constraining configuration.

41. A delivery system for a bifurcated intracorporeal device comprising:

an elongate shaft having a proximal section and a distal section with the distal section comprising:

an elongate primary belt support member;

at least one primary belt secured to the primary belt support member configured to be circumferentially disposed about the bifurcated intracorporeal device so to at least partially constrain the device;

a primary release member configured to engage and releasably secure the primary belt in a constraining configuration;

at least one elongate secondary belt support member disposed adjacent the elongate primary belt support member;

at least one secondary belt secured to the secondary belt support member configured to be circumferentially disposed about the bifurcated intracorporeal device so to at least partially constrain the device; and a secondary release member configured to engage and releasably secure the secondary belt in a constraining configuration, wherein the primary belt and the secondary belt each comprises a length of wire having a first end and a second end with each of said first and second wire ends secured to the primary belt support member and secondary belt support member, respectively.

42. The delivery system of claim 41 wherein one or both of the primary belt and the secondary belt comprises first and second opposed ends.

43. The delivery system of claim 42 wherein each of the first and second opposed ends forms an end loop.

44. The delivery system of claim 41 wherein the wire comprises nickel titanium.

45. The delivery system of claim 41 wherein the release members comprise release wires moveably disposed within opposed looped ends of the respective belts.

46. The delivery system of claim 41 wherein the belts in the constraining configuration form planes that are substantially orthogonal to a longitudinal axis of the elongate shaft.

47. The delivery system of claim 41 wherein at least two belts are configured to be releasable by a single release member.

48. The delivery system of claim 41 comprising a plurality of primary release members wherein the proximal ends of at least two of the primary release members are color-coded.

49. The delivery system of claim 41 wherein proximal ends of the primary and secondary release members are in a linear spatial configuration at a proximal end of the delivery system that corresponds to a desired deployment sequence for the primary belt(s) and secondary belt(s).

50. The delivery system of claim 49 wherein the primary and secondary release members comprise release wire handles that are disposed in a nested configuration.

51. The delivery system of claim 41 wherein the at least one primary belt and the at least one secondary belt are configured to be circumferentially disposed about self expanding members on the bifurcated intracorporeal device.

52. A delivery system for a bifurcated graft comprising:

an elongate shaft having a proximal section and a distal section with the distal section comprising:

a portion having disposed thereon the bifurcated graft, the graft having a main body portion, an ipsilateral leg and a contralateral leg, a self-expanding tubular stent disposed at a distal end of the bifurcated graft main body portion;

an elongate primary belt support member disposed adjacent the main body portion and ipsilateral leg;

at least one primary belt secured to the primary belt support member and circumferentially disposed about the self-expanding tubular stent;

a primary release member which releasably secures the primary belt in the constraining configuration;

at least one secondary belt support member disposed adjacent the contralateral leg;

at least one secondary belt secured to the secondary belt support member and circumferentially disposed about the bifurcated graft and which constrains at least a portion of the graft; and a secondary release member which releasably secures the secondary belt in the constraining configuration.

53. The delivery system of claim 52 wherein one or both of the primary belt and the secondary belt comprises first and second opposed ends.

54. The delivery system of claim 53 wherein each of the first and second opposed ends forms an end loop.

55. The delivery system of claim 52 wherein the release members comprise nickel titanium.

56. The delivery system of claim 52 wherein the release members comprise release wires moveably disposed within opposed looped ends of the respective belts.

57. The delivery system of claim 52 wherein the belts in the constraining configuration form planes that are substantially orthogonal to a longitudinal axis of the elongate shaft.

58. The delivery system of claim 52 wherein at least two belts are configured to be releasable by a single release member.

59. The delivery system of claim 52 comprising a plurality of primary release members wherein the proximal ends of at least two of the primary release members are color-coded.

60. The delivery system of claim 52 wherein the at least one primary belt comprises a plurality of primary belts and wherein the primary release member comprises a plurality of primary release members that releasably secure the plurality of primary belts, wherein proximal ends of the primary release members are in a linear spatial configuration at a proximal end of the delivery system that corresponds to a desired deployment sequence for the plurality of belts.

61. The delivery system of claim 60 wherein the plurality of primary release members comprise a distal primary release wire handle and a proximal primary release wire handle disposed in a nested configuration.

62. The delivery system of claim 52 additionally comprising a first proximal self-expending member secured to a proximal end of the contralateral leg and a second proximal self-expanding member secured to a proximal end of the ipsilateral leg, and wherein the legs have a different length and the first and second proximal self-expanding members are axially offset from each other when the graft is in a constrained state within the delivery system.

63. The delivery system of claim 52 additionally comprising a first proximal self-expanding member secured to a proximal end of the contralateral leg and a second proximal self-expanding member secured to a proximal end of the ipsilateral leg, and wherein the legs have substantially the same length and one of the legs is axially compressed or folded such that the first and second proximal self-expanding members are axially offset from each other when the graft is in a constrained state within the delivery system.

64. The delivery system of claim 52 wherein the stent comprises a circumferential groove configured to accept at least a portion of the primary belt.

65. The delivery system of claim 52 wherein the bifurcated graft is inflatable, wherein the delivery system further comprises an inflation lumen that is releasably coupleable to the bifurcated graft.

66. A delivery system for a bifurcated graft comprising:

an elongate shaft having a proximal section and a distal section with the distal section comprising:

a portion having disposed thereon the bifurcated graft, the graft having a main body portion, an ipsilateral leg and a contralateral leg;

an elongate primary belt support member disposed adjacent the main body portion and ipsilateral leg;

at least one primary belt secured to the primary belt support member and circumferentially disposed about the bifurcated graft and which constrains at least a portion of the graft;

a primary release member which releasably secures the primary belt in the constraining configuration;

at least one secondary belt support member disposed adjacent the contralateral leg;

at least one secondary belt secured to the secondary belt support member and circumferentially disposed about the bifurcated graft and which constrains at least a portion of the graft; and a secondary release member which releasably secures the secondary belt in the constraining configuration, wherein the primary belt and the secondary belt comprise at least one length of wire having a first end and a second end and configured in a loop with each of said first and second wire ends secured to the primary belt support member and secondary belt support member, respectively.

67. The delivery system of claim 66 wherein the length of wires have opposed end loops having differing diameters.

68. The delivery system of claim 66 wherein the wire comprises nickel titanium.

69. The delivery system of claim 66 wherein the release members comprise release wires moveably disposed within opposed looped ends of their respective belts.

70. The delivery system of claim 66 wherein the belts in the constraining configuration form planes that are substantially orthogonal to a longitudinal axis of the elongate shaft.

71. The delivery system of claim 66 wherein at least two primary belts are configured to be releasable by the same release member.

72. The delivery system of claim 66 wherein the primary belt support member comprises a guidewire tube.

73. The delivery system of claim 72 wherein the distal section further comprises an outer protective sheath disposed about the endovascular graft while the graft is in a constrained state.

74. The delivery system of claim 66 wherein proximal ends of the primary and secondary release members are in a linear spatial configuration at a proximal end of the delivery system that corresponds to a desired deployment sequence for the primary belt(s) and secondary belt(s).

75. The delivery system of claim 74 wherein the primary and secondary release members comprise release wire handles that are disposed in a nested configuration.

* * * * *